United States Patent [19]
Urfer et al.

[11] Patent Number: 5,981,480
[45] Date of Patent: Nov. 9, 1999

[54] PANTROPIC NEUROTROPHIC FACTORS

[75] Inventors: Roman Urfer, Pacifica; Leonard G. Presta, San Francisco; John W. Winslow, El Granada, all of Calif.

[73] Assignee: Genentech, Inc., South San Francisco, Calif.

[21] Appl. No.: 08/441,513

[22] Filed: May 15, 1995

Related U.S. Application Data

[63] Continuation of application No. 08/253,937, Jun. 3, 1994, abandoned.

[51] Int. Cl.$^6$ .......................... C07K 14/475; A61K 38/18
[52] U.S. Cl. .............................. 514/12; 530/350; 530/399
[58] Field of Search .................................. 435/69.1, 69.7; 530/350, 399; 514/2, 12

[56] References Cited

U.S. PATENT DOCUMENTS 5,169,764  12/1992  Shooter et al. .

FOREIGN PATENT DOCUMENTS

| WO 92/02620 | 2/1992 | WIPO . |
| WO 93/18066 | 9/1993 | WIPO . |
| WO 93/25684 | 12/1993 | WIPO . |
| WO 94/12539 | 6/1994 | WIPO . |

OTHER PUBLICATIONS

Rudinger, J. In *Peptide Hormones* ed. Parsons J.A., University Park Press, Baltimore, pp. 1–7, 1976.

Jungbluth et al., "Purification and Characterisation of a brain–derived Neurotrophic Factor/Neurotrophin–3 (BDNF/NT–3) Heterodimer" *European Journal of Biochemistry* 221:677–685 (1994).

Urfer et al., "The Binding Epitopes of Neurotrophin–3 to its Receptors trkC and gp75 and the Design of a Multifuntional Human Neurotrophin" *The EMBO Journal* 13(24):5896–5909 (1994).

Barde et al., "Purification of a new neurotrophic factor from mammalian brain" *EMBO Journal* 1(5):549–553 (1982).

Barde, Y. A., "Trophic Factors and Neuronal Survival" *Neuron.* 2:1525–1534 (1989).

Berkemeier et al., "Neurotrophin–5: A Novel Neurotrophic Factor That Activates trk and trkB" *Neuron* 7:857–866 (Nov. 1991).

Bothwell, M., "Keeping Track of Neurotrophin Receptors" *Cell* 65:915–918 (Jun. 14, 1991).

Burton et al., "Activity and Biospecificity of Proteolized Forms and Dimeric Combinations of Recombinant Human and Murine Nerve Growth Factor" *J. Neurochem.* 59(5):1937–1945 (1992).

Camerini et al., "The T Cell Activation Antigen CD27 is a Member of the Nerve Growth Factor/Tumor Necrosis Factor Receptor Gene Family" *J. Immunol.* 147(9):3165–3169 (Nov. 1, 1991).

Chao, M. V., "Neurotrophin Receptors: A Window into Neuronal Differentiation" *Neuron* 9:583–593 (Oct. 1992).

Connolly et al., "Pit Formation and Rapid Changes in Surface Morphology of Sympathetic Neurons in Response to Nerve Growth Factor" *Journal of Cell Biology* 90:176–180 (Jul. 1981).

Cordon–Cardo et al., "The trk Tyrosine Protein Kinase Mediates the Mitogenic Properties of Nerve Growth Factor and Neurotrophin–3" *Cell* 66:173–183 (Jul. 12, 1991).

Davies et al., "Neurotrophin–4/5 Is a Mammalian–specific Survival Factor for Distinct Populations of Sensory Neurons" *J. Neuroscience* 13(11):4961–4967 (Nov. 1993).

Davies et al., "The Response of Chick Sensory Neurons to Brain–Derived Neurotrophic Factor" *Neuroscience* 6(7):1897–1904 (Jul. 1986).

Davies, A. M., "Role of neurotrophic factors in development" *Trends in Genetics* pp. 139–143 (1988).

Ernfors et al., "Molecular cloning and neurotrophic activities of a protein with structural similarities to nerve growth factor: Developmental and topographical expression in the brain" *Proc. Natl. Acad. Sci. USA* 87:5454–5458 (Jul. 1990).

Halegoua et al., "Nerve Growth Factor Mediates Phosphorylation of Specific Proteins" *Cell* 22:571–581 (Nov. 1980).

Hallbook et al., "Evolutionary Studies of the Nerve Growth Factor Family Reveal a Novel Member Abundantly Expressed in Xenopus Ovary" *Neuron* 6:845–858 (May 1991).

Hefti, Franz, "Nerve Growth Factor Promotes Survival of Septal Cholinergic Neurons After Fimbrial Transections" *J. of Neuroscience* 6(8):2155–2162 (Aug. 1986).

Hohn et al., "Identification and characterization of a novel member of the nerve growth factor/brain–derived neurotrophic factor family" *Nature* 344:339–341 (Mar. 22, 1990).

Hory–Lee et al., "Neurotrophin 3 supports the survival of developing muscle sensory neurons in culture" *Proc. Natl. Acad. Sci. USA* 90:2613–2617 (Apr. 1993).

Ibanez et al., "Chimeric molecules with multiple neurotrophic activities reveal structural elements determining the specificities of NGF and BDNF" *BMBO Journal* 10(8):2105–2110 (1991).

Ibanez et al., "Disruption of the Low Affinity Receptor–Binding Site in NGF Allows Neuronal Survival and Differentiation by Binding to the trk Gene Product" *Cell* 69:329–341 (Apr. 17, 1992).

Ibanez et al., "An extended surface of binding to Trk tyrosine kinase receptors in NGF and BDNF allows the engineering of a multifunctional pan–neurotrophin" *EMBO Journal* 12(6):2281–2293 (1993).

Ip et al., "Mammalian neurotrophin–4: Structure, chromosomal localization, tissue distribution, and receptor specificity" *Proc. Natl. Acad. Sci. USA* 89:3060–3064 (Apr. 1992).

Ip et al., "Similarities and Differences in the Way Neurotrophins Interact with the Trk Receptors in Neuronal and Nonneuronal Cells" *Neuron* 10:137–149 (Feb. 1993).

Johnson et al., "Expression and Structure of the Human NGF Receptor" *Cell* 47:545–554 (Nov. 21, 1986).

Jones et al., "Molecular cloning of a human gene that is a member of the nerve growth factor family" *Proc. Natl. Acad. Sci. USA* 87:8060–8064 (1990).

Kahle et al., "The Amino Terminus of Nerve Growth Factor Is Involved in the Interaction with the Receptor Tyrosine Kinase $p140^{trkA}$" *Journal of Biological Chemistry* 267(32):22707–22710 (Nov. 15, 1992).

Kaisho et al., "Cloning and expression of a cDNA encoding a novel human neurotrophic factor" *FEBS Letters* 266(1, 2):187–191 (Jun. 1990).

Kalcheim et al., "Neurotrophin 3 is a mitogen for cultured neural crest cells" *Proc. Natl. Acad. USA* 89:1661–1665 (Mar. 1992).

Kaplan et al., "The trk Proto–Oncogene Product: A Signal Transducing Receptor for Nerve Growth Factor" *Science* 252:554–558 (Apr. 26, 1991).

Kaplan et al., "Tyrosine phosphorylation and tyrosine kinase activity of the trk proto–oncogene product induced by NGF" *Nature* 350:158–160 (Mar. 14, 1991).

Klein et al., "The trk Proto–Oncogene Encodes a Receptor for Nerve Growth Factor" *Cell* 65:189–197 (Apr. 5, 1991).

Klein et al., "The trkB Tyrosine Protein Kinase Is a Receptor for Brain–Derived Neurotrophic Factor and Neurotrophin–3" *Cell* 66:395–402 (Jul. 26, 1991).

Klein et al., "The trkB Tyrosine Protein Kinase Is a Receptor for Neurotrophin–4" *Neuron* 8:947–956 (May 1992).

Klein et al., "trkB, a novel tyrosine protein kinase receptor expressed during mouse neural development" *EMBO Journal* 8(12):3701–3709 (1989).

Korsching, Sigrun, "The role of nerve growth factor in the CNS" *TINS* pp. 570–573 (Nov./Dec. 1986).

Lamballe et al., "trkC, a New Member of the trk Family of Tyrosine Protein Kinases, Is a Receptor for Neurotrophin–3" *Cell* 66:967–979 (Sep. 6, 1991).

Leibrock et al., "Molecular cloning and expression of brain–derived neurotrophic factor" *Nature* 341:149–152 (Sep. 14, 1989).

Levi–Montalcini et al., "Nerve Growth Factor" *Physiol. Rev.* 48(3):535–569 (Jul. 1968).

Loetscher et al., "Molecular Cloning and Expression of the Human 55 kd Tumor Necrosis Factor Receptor" *Cell* 61:351–359 (Apr. 20, 1990).

Maisonpierre et al., "Neurotrophin–3: A Neurotrophic Factor Related to NGF and BDNF" *Science* 247:1446–1451 (Mar. 23, 1990).

Maisonpierre et al., "NT–3, BDNF, and NGF in the Developing Rat Nervous System: Parallel as well as Reciprocal Patterns of Expression" *Neuron* 5:501–509 (Oct. 1990).

Mallett et al., "Characterization of the MRC OX40 antigen of activated CD4 positive T lymphocytes—a molecule related to nerve growth factor receptor" *EMBO Journal* 9(4):1063–1068 (1990).

Martin–Zanca et al., "Molecular and Biochemical Characterization of the Human trk Proto–Oncogene" *Molecular & Cellular Biology* 9(1):24–33 (Jan. 1989).

Radeke et al., "Gene transfer and molecular cloning of the rat nerve growth factor receptor" *Nature* 325:593–597 (Feb. 12, 1987).

Reidhaar–Olson et al., "Combinatorial Cassette Mutagenesis as a Probe of the Informational Content of Protein Sequences" *Science* 241:53–57 (Jul. 1, 1988).

Rosenthal et al., "Primary Structure and Biological Activity of a Novel Human Neurotrophic Factor" *Neuron* 4:767–773 (May 1990).

Schall et al., "Molecular Cloning and Expression of a Receptor for Human Tumor Necrosis Factor" *Cell* 61:361–370 (Apr. 20, 1990).

Shelton et al., "Expression of the β–nerve growth factor gene correlates with the density of sympathetic innervation in effector organs" *Proc. Natl. Acad. Sci. USA* 81:7951–7955 (Dec. 1984).

Shelton et al., "Studies on the expression of the β nerve growth factor (NGF) gene in the central nervous system: Level and regional distribution of NGF mRNA suggest that NGF functions as a trophic factor for several distinct populations of neurons" *Proc. Natl. Acad. Sci. USA* 83:2714–2718 (Apr. 1986).

Skaper et al., "Maintenance by Nerve Growth Factor of the Intracellular Sodium Environment in Spinal Sensory and Sympathetic Ganglionic Cells" *Brain Research* 197:379–389 (1980).

Smith et al., "A Receptor for Tumor Necrosis Factor Defines an Unusual Family of Cellular and Viral Proteins" *Science* 248:1019–1023 (May 25, 1990).

Snider et al., "Neurotrophic Molecules" *Am. Neurological Assn.* 26(4):489–506 (Oct. 1989).

Soppet et al., "The Neurotrophic Factors Brain–Derived Neurotrophic Factor and Neurotrophin–3 Are Ligands for the trkB Tyrosine Kinase Receptor" *Cell* 65:895–903 (May 31, 1991).

Squinto et al., "trkB Encodes a Functional Receptor for Brain–Derived Neurotrophic Factor and Neurotrophin–3 but Not Nerve Growth Factor" *Cell* 65:885–893 (May 31, 1991).

Stamenkovic et al., "A B–lymphocyte activation molecule related to the nerve growth factor receptor and induced by cytokines in carcinomas" *EMBO Journal* 8(5):1403–1410 (1989).

Suter et al., "NGF/BDNF Chimeric Proteins: Analysis of Neurotrophin Specificity by Homolog–scanning Mutagenesis" *J. Neurosci.* 12(1):306–318 (Jan. 1992).

Thoenen et al., "The Physiological Function of Nerve Growth Factor in the Central Nervous System: Comparison With the Periphery" *Rev. Physiol. Biochem. Pharmacol.* 109:146–178 (1987).

Tiercy et al., "Early Changes in the Synthesis of Nuclear and Cytoplasmic Proteins Are Induced by Nerve Growth Factor in Differentiating Rat PC12 Cells" *Journal of Cell Biology* 103(6):2367–2378 (Dec. 1986).

Tsoulfas et al., "The Rat trkC Locus Encodes Multiple Neurogenic Receptors That Exhibit Differential Response to Neurotrophin–3 in PC12 Cells" *Neuron* 10:975–990 (May 1993).

Vallette et al., "Construction of mutant and chimeric genes using the polymerase chain reaction" *Nucl. Acids Res.* 17(2):723–733 (1989).

Wong 35 al., "Human GM–CSF: Molecular Cloning of the Complementary DNA and Purification of the Natural and Recombinant Proteins" *Science* 228:810–815 (May 17, 1985).

Yang et al., "Human IL–3 (Multi–CSF): Identification by Expression Cloning of a Novel Hematopoietic Growth Factor Related to Murine IL–3" *Cell* 47:3–10 (Oct. 10, 1986).

Yu et al., "Increased Phosphorylation of Specific Nuclear Proteins in Superior Cervical Ganglia and PC12 Cells in Response to Nerve Growth Factor" *Journal of Biological Chemistry* 255(21):10481–10492 (Nov. 10, 1980).

*Primary Examiner*—Paula K. Hutzell
*Assistant Examiner*—Stephen Gucker
*Attorney, Agent, or Firm*—Timothy E. Torchia; Sean A. Johnston

[57] ABSTRACT

Pantropic neurotrophic factors which have multiple neurotrophic specificities are provided. The pantropic neurotrophic factors of the present invention are useful in the treatment of neuronal disorders. Nucleic acids and expression vectors encoding the pantropic neurotrophins are also provided.

4 Claims, 38 Drawing Sheets

FIG. 8

NGF/NT3 Homologue-scanning mutagenesis

| Region | Mutant | Amino Acid Residues Changed |
|---|---|---|
| N-terminus | 6 | S1Y, S2A, S3E, P5K, I6S, F7S |
| Beta sheet A (C1) | 20 | V18E, V20L, G23T |
| Beta-turn 1' (V1) | 10 | K32R, K34H, E35Q |
| Beta-turn 1 (V1) | 19 | T26S, T27S, T29I, K32R, K34H, E35Q |
| Beta-turn 2 (V2) | 12 | V42I, N43K, I44T, N45G, V48P, F49V |
| Beta-turn 2' (V2) | 13 | N43K, I44T, N45G |
| Beta-turn 3 (V3) | 7 | R59K, D60E, P61A, N62R, D65K, S66N |
| Beta-turn 3' (V3) | 14 | R59K, D60E, D65K, S66N |
| Beta-turn 3/4 (C3/V4) | 22 | S73D, Y79Q, T81K |
| Beta sheet C (V4) | 16 | T81K, T83S, H84Q, F86Y, K88R |
| Beta-turn 5 (V5) | 8 | M92S, D93E, G94N, +N94/95, Q96L, A97V, A98G |
| Beta-turn 3+5 (V3,V5) | 9 | R59K, D60E, P61A, N62R, D65K, S66N, M92S, D93E, G94N, +N94/95, Q96L, A97V, A98G |
| C-terminus | 23 | +A116, V117I, R118G, A120T |

FIG. 18C-1

Alanine replacement mutagenesis or truncation

| Region | # | Mutation |
|---|---|---|
| N-terminus | D9 | deletion S1-R9 |
| N-terminus | D5 | deletion S1-P5 |
| N-terminus | 1 | H4A |
| N-terminus | 2 | H4D |
| N-terminus | 3 | R9A |
| N-terminus | 4 | H4A, H8A, R9A |
| N-terminus (BDNF) | 5 | S1H, S3D, H4P, P5A, I6(-), F7(-), H8R |
| N-terminus | 32 | P5A |
| N-terminus | 31 | H8A |
| Beta sheet A (C1) | 37 | E11A |
| Beta sheet A (C1) | 58 | F12A |
| Beta sheet A (C1) | 41 | S13M |
| Beta sheet A (C1) | 29 | D16A |
| Beta-turn 1 (V1) | 38 | D24A |
| Beta-turn 1 (V1) | 50 | K25Q |
| Beta-turn 1 (V1) | 39 | T26K |
| Beta-turn 1 (V1) | 40 | T27E |
| Beta-turn 1 (V1) | 49 | D30N |
| Beta-turn 1 (V1) | 60 | I31A |
| Beta-turn 1 (V1) | 21 | K32A, K34A, E35A |
| Beta-turn 2 (V2) | 53 | L39E |
| Beta-turn 2 (V2) | 51 | E41A |
| Beta-turn 2 (V2) | 33 | N46K |
| Beta-turn 2 (V2) | 52 | S47A |
| Beta-turn 2 (V2) | 34 | K50A |
| Beta sheet B (C2) | 27 | Y52A |
| Beta sheet B (C2) | 28 | Y52F |
| Beta sheet B (C2) | 35 | E55A |
| Beta sheet B (C2) | 36 | K57A |
| Beta-turn 3 (V3) | 45 | R59A |
| Beta-turn 3/4 (C3) | 30 | R69A |
| Beta-turn 3/4 (C3) | 57 | D72A |
| Beta-turn 3/4 (C3) | 42 | K74A |
| Beta-turn 3/4 (C3) | 43 | H75A |
| Beta-turn 3/4 (C3) | 44 | N77A |
| Beta sheet C (V4) | 46 | Y79A+T81K |
| Beta sheet C (V4) | 47 | H84A+K88A |
| Beta sheet C (V4) | 61 | H84M |
| Beta sheet C (V4) | 62 | K88M |
| Beta sheet C (V4) | 55 | L90E |
| Beta-turn 4 (V5) | 56 | A97E |
| Beta sheet D (C4) | 25 | R103A |
| Beta sheet D (C4) | 26 | R103K |
| Beta sheet D (C4) | 48 | D105A |
| Beta sheet D (C4) | 63 | D105N |
| C-terminus | 65 | L112A+S113A |
| C-terminus | 24 | R115A, K116A, R119A |
| C-terminus | 64 | K115A |

FIG. 18C-2

NT3-NH2/NGF

NT3 (1-6)  NGF

NGF-NH2/NT3

NGF (1-7)  NT3

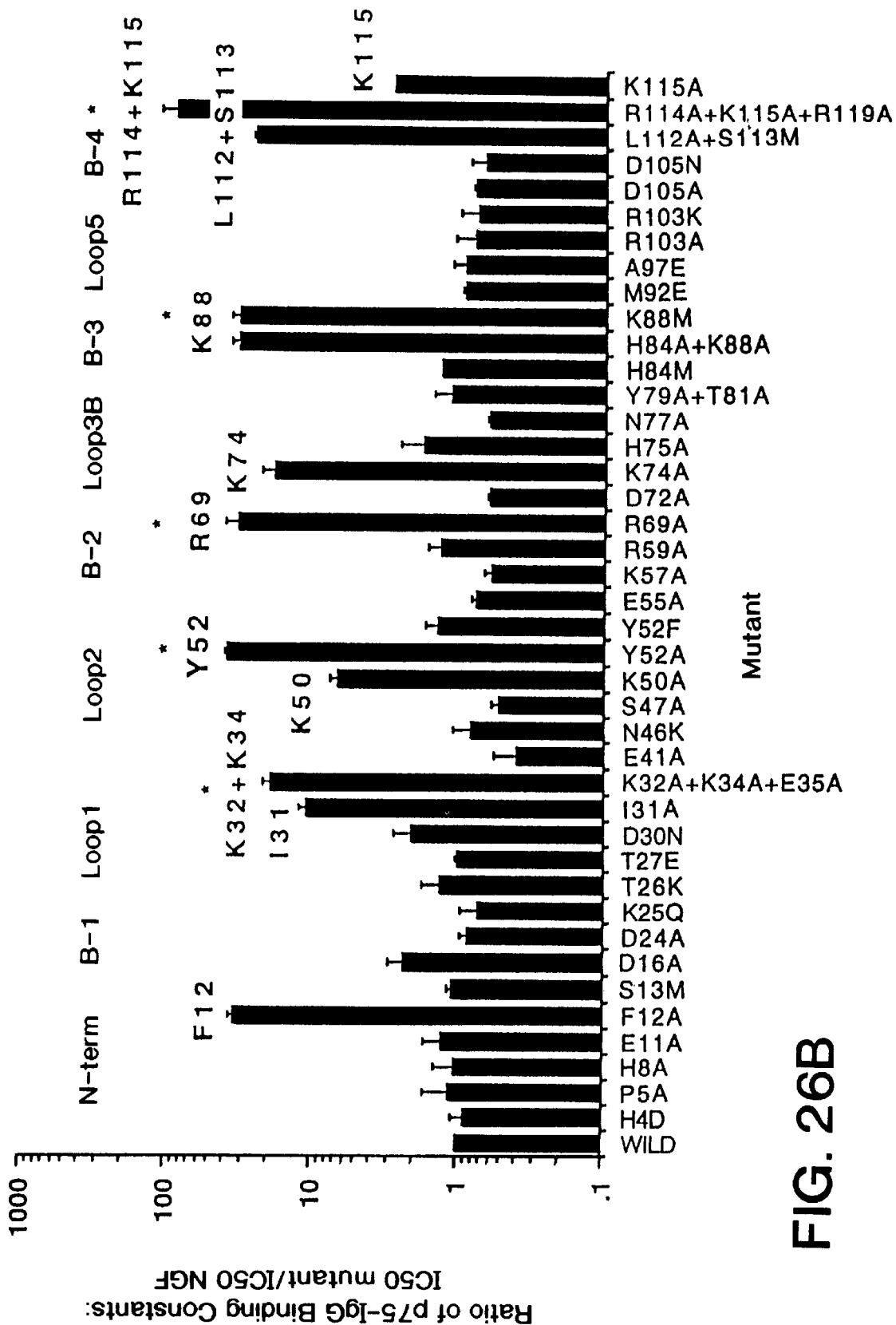

PANTROPIC NEUROTROPHIC FACTORS

This is a continuation of application Ser. No. 08/253,937 filed on Jun. 3, 1994, abandoned, which application is incorporated herein by reference and to which application priority is claimed under 35 USC §120.

FIELD OF THE INVENTION

This application relates to proteins which are involved in the growth, regulation or maintenance of nervous tissue, particularly neurons. In particular, it relates to pantropic neurotrophic factors which have multiple neurotrophic specificities (MNTS variants).

BACKGROUND OF THE INVENTION

The survival and maintenance of differentiated function of vertebrate neurons is influenced by the availability of specific proteins referred to as neurotrophins. Developing neurons depend for survival on the supply of these factors from their target fields and the limited production of neurotrophins results in death of superfluous neurons (for reviews, see (1); (2)). The various neurotrophins differ functionally in their ability to support survival of distinct neuronal populations in the central and the peripheral nerve system (3), (4); (5), (80).

The neurotrophin family is a highly homologous family which includes NT3 (6), (7); (5); (8); (9); (10), nerve growth factor (NGF) (11); (12), brain-derived neurotrophic factor (BDNF) (13); (14)) and neurotrophin 4/5 (NT4/5) ((15), (16), (17).

Studies suggest that neurotrophins transduce intracellular signalling at least in part through the ligand-dependent activation of a class of tyrosine kinase-containing receptors of $M_r$=140–145,000 known as the trks (18); (19) (21); (20) (22); (23); (24); (25); (26). Thus, the signal transduction pathway of neurotrophins is initiated by this high-affinity binding to and activation of specific tyrosine kinase receptors and subsequent receptor autophosphorylation (19); (27). Although there is some degree of cross-receptor interaction between the neurotrophins and the different trks, the predominant specificity appears to be NGF/trkA, BDNF/trkB, and NT3/trkC while NT4/5 appears to interact primarily with trkB as efficiently as BDNF (27); (19) (21); (25); (22); (28); (18); (28a). While trkC responds exclusively to NT3 (25); (26), trkA and trkB can respond in vitro under certain circumstances to multiple neurotrophins (6); (23). However, the neuronal environment does restrict trkA and trkB in their ability to respond to non-preferred neurotrophic ligands (29). In addition to the trk family of receptors, the neurotrophins can also bind to a different class of receptor termed the p75 low affinity NGF receptor (p75; (30); (31)) which has an unknown mechanism of transmembrane signalling but is structurally related to a receptor gene family which includes the tumor necrosis factor receptor (TNFR), CD40, OX40, and CD27 (32); (33); (34), (35); (36); (37)). The role of the gp75 in the formation of high-affinity binding sites and in the signal transduction pathway of neurotrophins is as yet unclear (for reviews see (38); (39)).

An examination of the primary amino acid sequence of the neurotrophins reveals seven regions of 7–10 residues each which account for 85% of the sequence divergence among the family members.

Nerve growth factor (NGF) is a 120 amino acid polypeptide homodimeric protein that has prominent effects on developing sensory and sympathetic neurons of the peripheral nervous system. NGF acts via specific cell surface receptors on responsive neurons to support neuronal survival, promote neurite outgrowth, and enhance neurochemical differentiation. NGF actions are accompanied by alterations in neuronal membranes (40), (41), in the state of phosphorylation of neuronal proteins (42), (43), and in the abundance of certain mRNAs and proteins likely to play a role in neuronal differentiation and function (see, for example (44)).

Forebrain cholinergic neurons also respond to NGF and may require NGF for trophic support. (45). Indeed, the distribution and ontogenesis of NGF and its receptor in the central nervous system (CNS) suggest that NGF acts as target-derived neurotrophic factor for basal forebrain cholinergic neurons (46), (81).

Little is known about the NGF amino acid residues necessary for the interaction with the trkA-tyrosine kinase receptor. Significant losses of biological activity and receptor binding were observed with purified homodimers of human and mouse NGF, representing homogenous truncated forms modified at the amino and carboxy termini. (47); (48); (49). The 109 amino acid species (10–118)hNGF, resulting from the loss of the first 9 residues of the N-terminus and the last two residues from the C-terminus of purified recombinant human NGF, is 300-fold less efficient in displacing mouse [$^{125}$I]NGF from the human trkA receptor compared to (1–118)HNGF (49). It is 50- to 100-fold less active in dorsal root ganglion and sympathetic ganglion survival compared to (1–118)hNGF (48). The (1–118)HNGF has considerably lower trkA tyrosine kinase autophosphorylation activity (49).

NT3 transcription has been detected in a wide array of peripheral tissues (e. g. kidney, liver, skin) as well as in the central nerve system (e. g. cerebellum, hippocampus) (5); (7), (82). During development, NT3 mRNA transcription is most prominent in regions of the central nervous system in which proliferation, migration and differentiation of neurons are ongoing (50). Supporting evidence for a role in neuronal development includes the promoting effect of NT3 on neural crest cells (51) and the stimulation of the proliferation of oligodendrocyte precursor cells in vivo (79). NT3 also supports in vitro the survival of sensory neurons from the nodose ganglion (NG) (7); (5), (83) and a population of muscle sensory neurons from dorsal root ganglion (DRG) (52). In addition to these in vitro studies, a recent report showed that NT3 prevents in vivo the degeneration of adult central noradrenergic neurons of the locus coerulus in a model that resembles the pattern of cell loss found in Alzheimer's disease. Currently, there are no published reports concerning the amino acid residues necessary for trkC binding.

There has been some limited attempts to create chimeric or pan-neurotrophic factors. (See (53); (56); (54), (55)).

SUMMARY OF THE INVENTION

It is an object of the invention to provide pantropic neurotrophins and to produce useful quantities of these pantropic neurotrophins using recombinant DNA techniques.

It is a further object of the invention to provide recombinant nucleic acids encoding pantropic neurotrophins, and expression vectors and host cells containing the nucleic acid encoding the pantropic neurotrophins.

An additional object of the invention is to provide methods for producing the pantropic neurotrophins, and for treating neuronal disorders of a patient.

In accordance with the foregoing objects, the present invention provides recombinant pantropic neurotrophins, and isolated or recombinant nucleic acids which encode the neurotrophins of the present invention. Also provided are expression vectors which comprise DNA encoding a pantropic neurotrophin operably linked to transcriptional and translational regulatory DNA, and host cells which contain the nucleic acids.

An additional aspect of the present invention provides methods for producing pantropic neurotrophins which comprises culturing a host cell transformed with an expression vector and causing expression of the nucleic acid encoding the pantropic neurotrophin to produce a recombinant neurotrophin.

Additionally provided are methods of treating a neural disorder comprising administering the pantropic neurotrophins of the present invention to a patient.

Additional objects and features of the invention will be apparent to those skilled in the art from the following detailed description and appended claims when taken in conjunction with the figures.

The response of medium from mock transfected cells was subtracted from each data point and was 23%, 23% and 29% for the 200 pg/ml, 1000 pg/ml and 5000 pg/ml experiment, respectively. (D) Response of PC12/trkC cells induced by conditioned medium containing either NT-3 or R68A mutant. Percentage of cells with neurites induced by different doses of neurotrophins. The sum of cells with and without neurites was constant for NT3 and R68A for all doses. (E) Survival of neurons from DRG. Response induced by NT-3, R68A or R114A/K115A expressed as number of surviving cells. Results are the mean value of triplicate determinations ±SD. The response induced by mock-transfected conditioned medium was subtracted from data points and was 20±4 surviving cells.

Figure 3A:
Figure 3B:
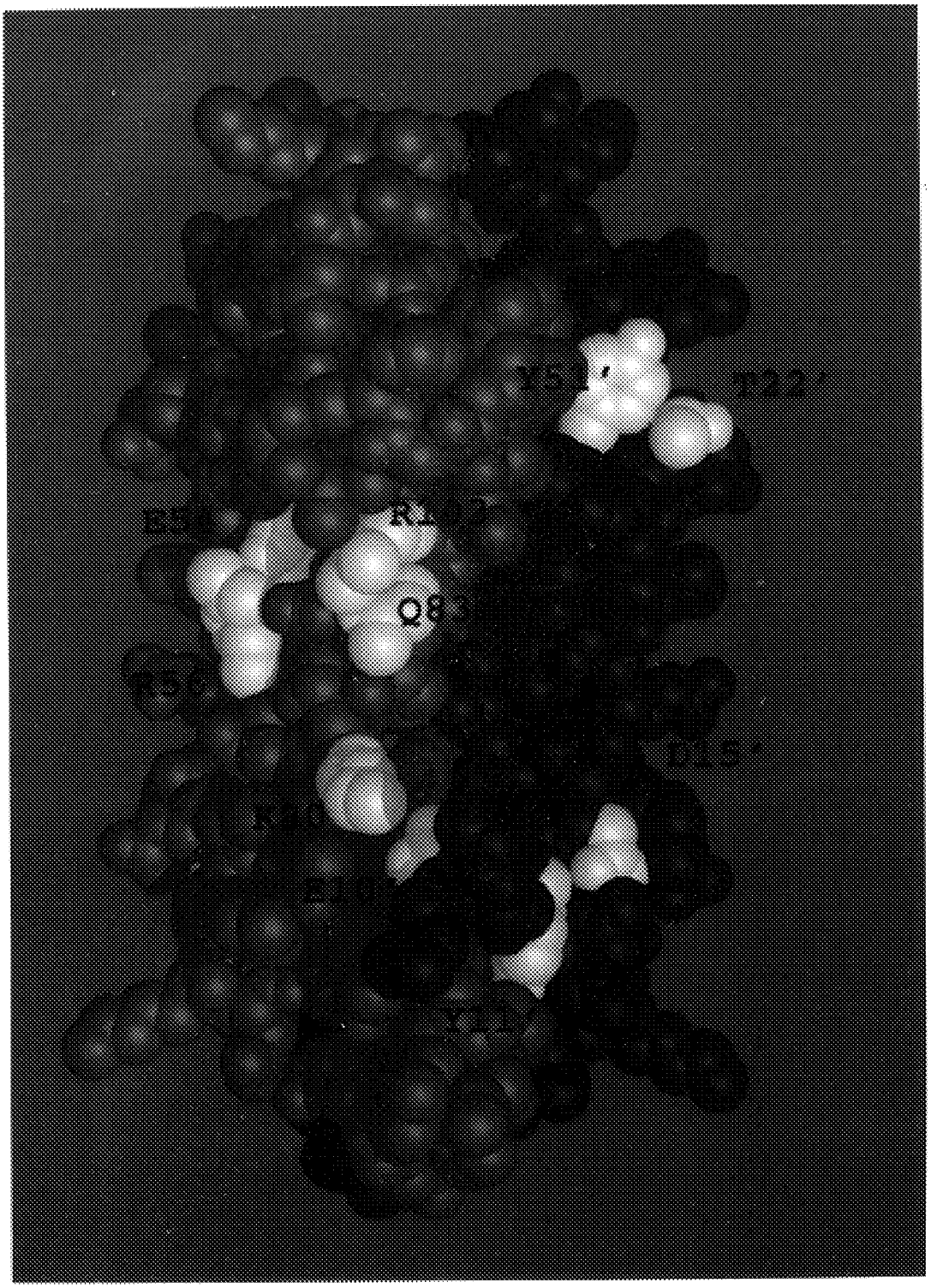
Figure 3C:
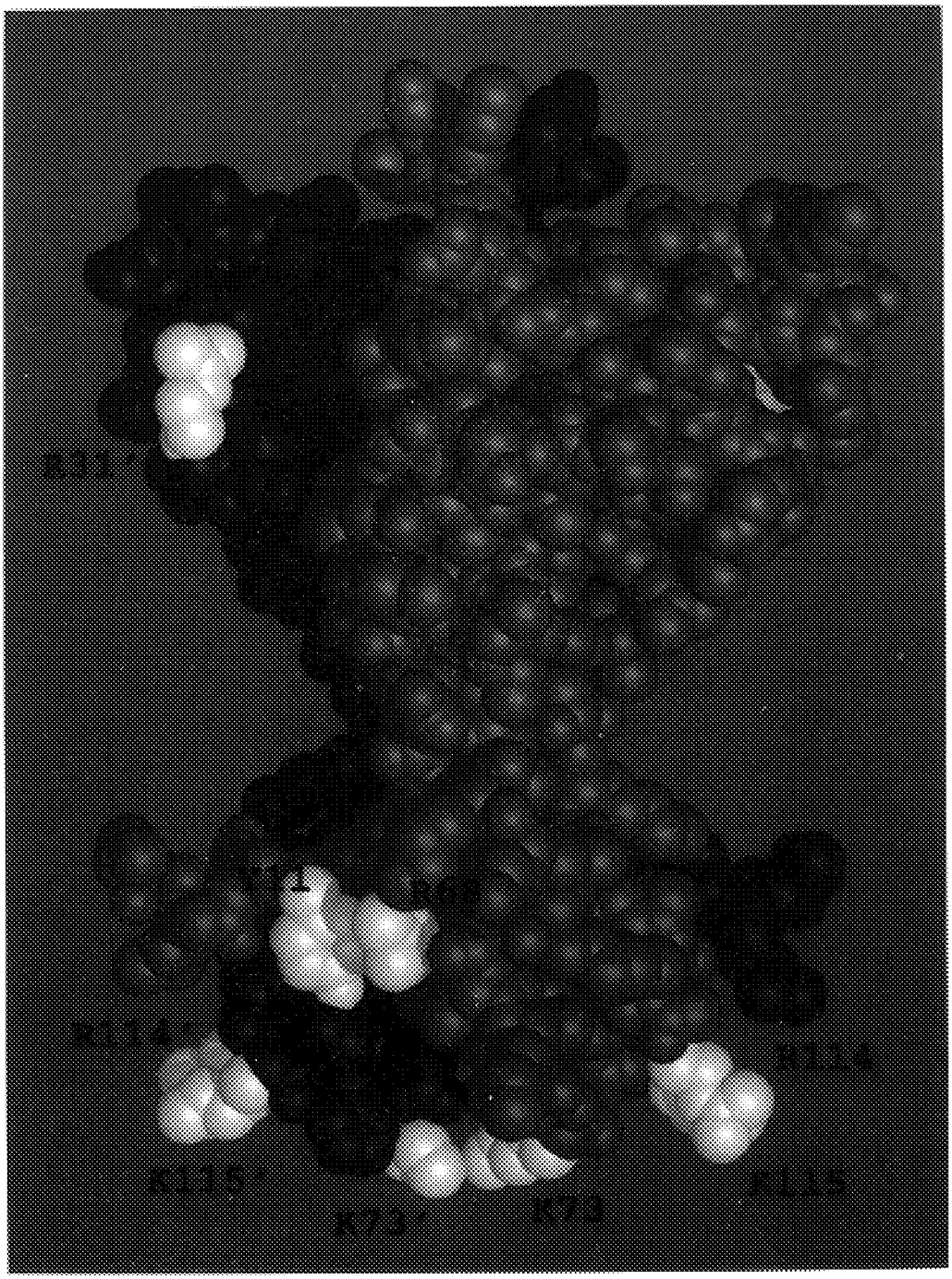
Figure 4A:
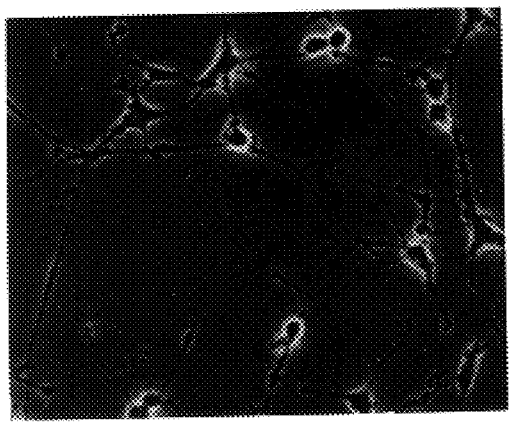
Figure 4B:
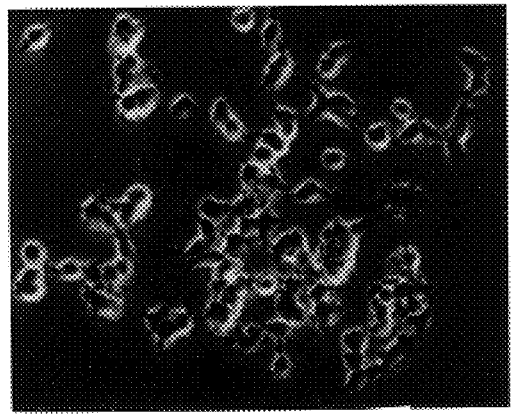
Figure 4C:
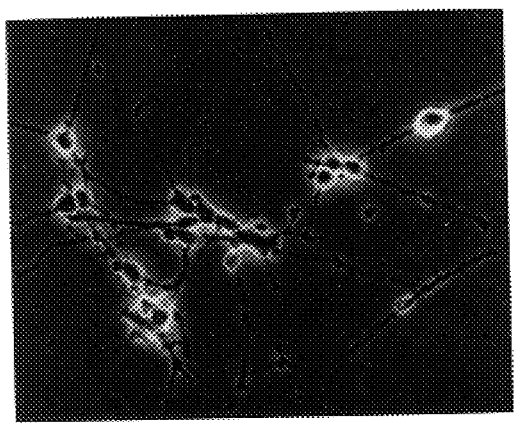
Figure 4D:
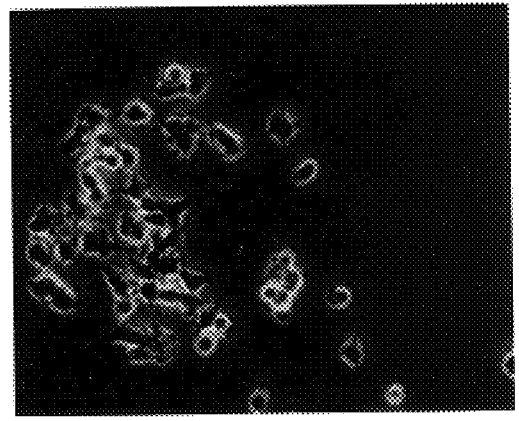
Figure 4E:
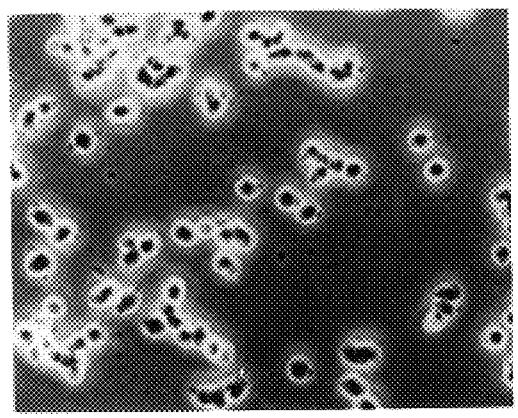
Figure 4F:
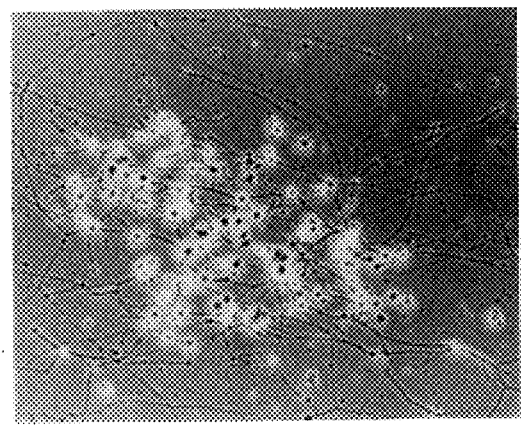
Figure 4G:
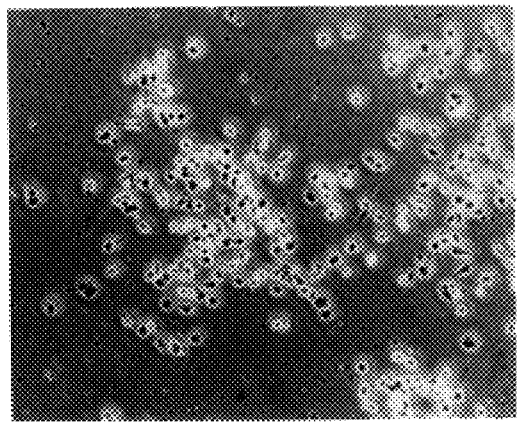
Figure 4H:
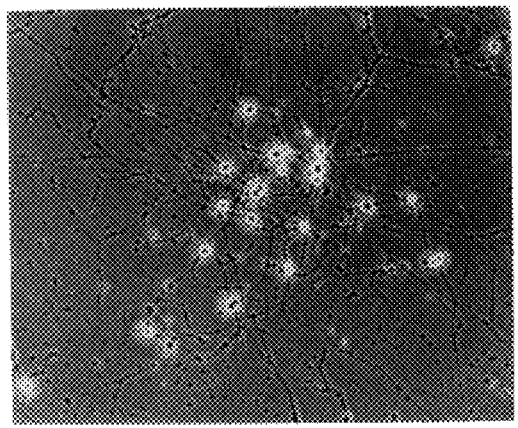
Figure 4I:
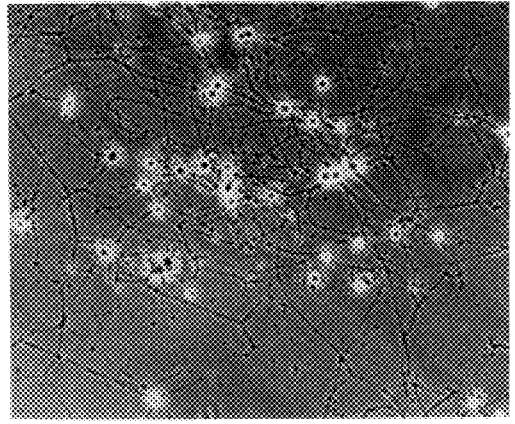
Figure 4J:
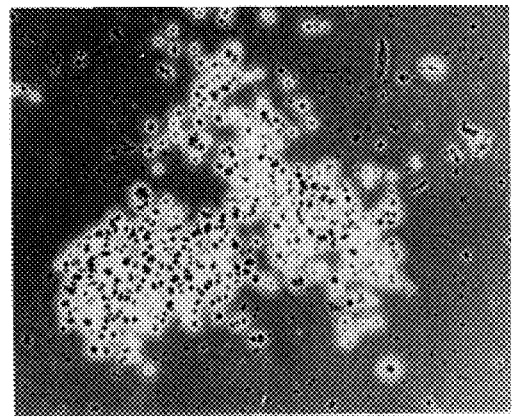
Figure 5A:
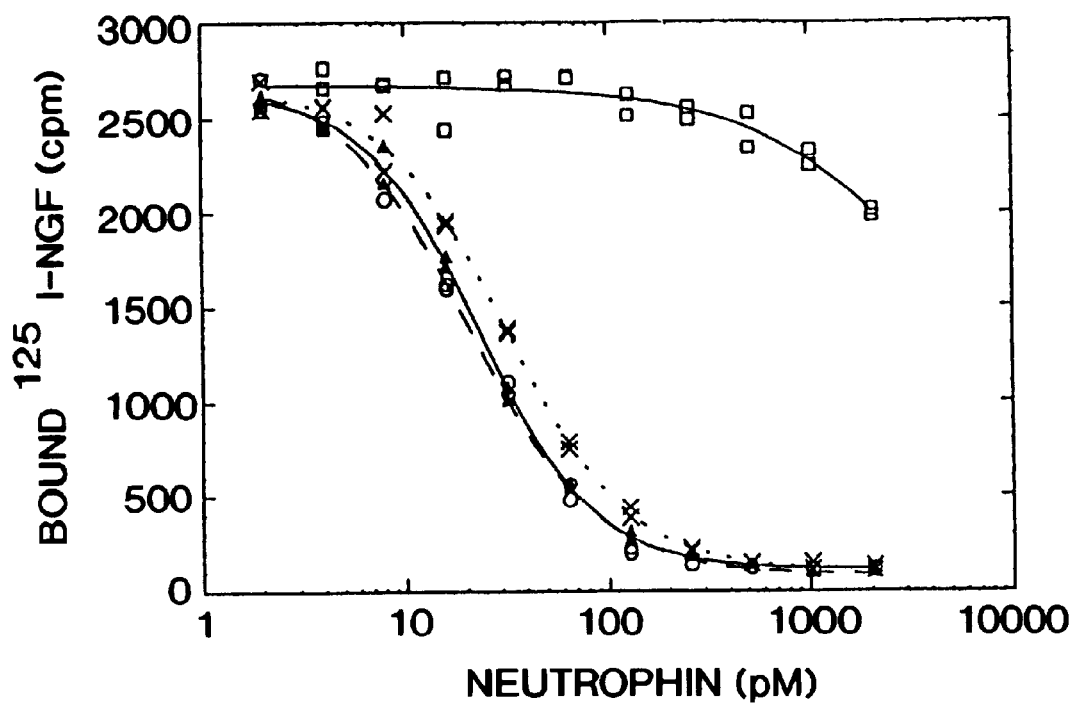
Figure 5B:
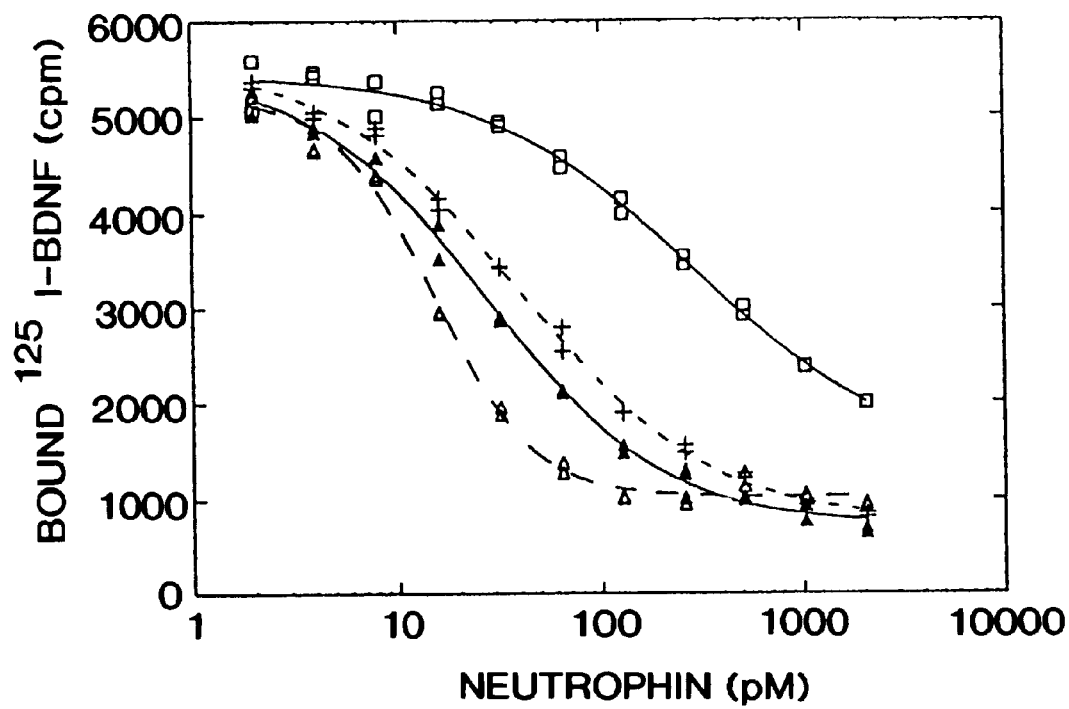
Figure 5C:
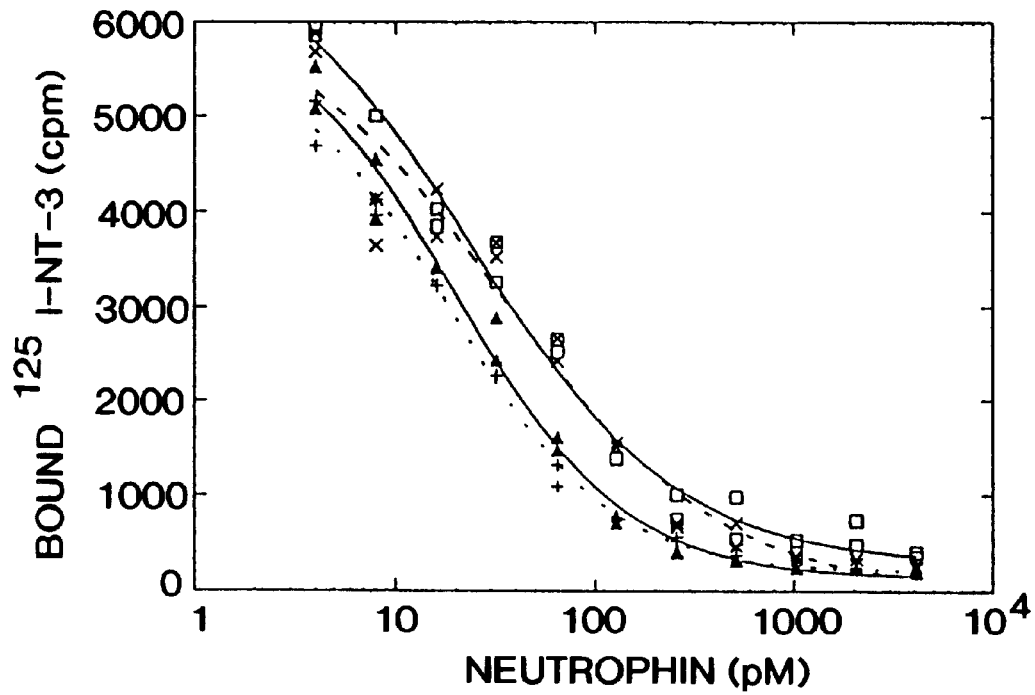
Figure 5D:
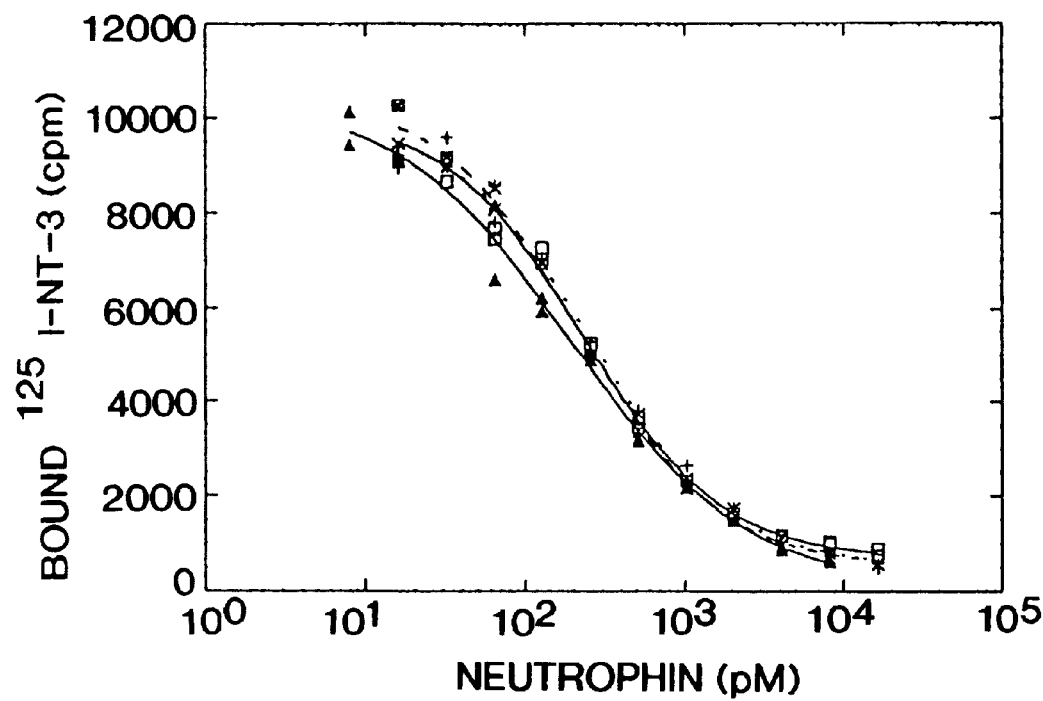

FIGS. 3A, 3B and 3C depict the binding epitopes of NT3 to its receptors trkC and gp75. The NT3 model is shown with binding determinants from monomer A and B are shown in light and dark grey, respectively. (A) Epitope for trkC receptor. (B) Side view of trkC epitope. Positions of D15 and Y51 relative to trkC binding determinants. (C) Epitope for gp75 receptor.

FIGS. 4A, 4B, 4C, 4D, 4E, 4F, 4G, 4H, 4I, and 4J depict the screening of NT3 mutants for improved BDNF and NGF like activities. PC12 cells or the PC12 cell line expressing trkB were plated on collagen-coated dishes. The PC12/trkB cell line was treated with PC12 medium supplemented either with BDNF (A), NT3 (B), mutant D15A (C) or supernatant of mock transfected 293 cells (E). The PC12 cells were treated with PC12 medium supplemented either with NGF (F), NT3 (G), S1 (H), D15A (D), MNTS-1 (I) or supernatant of mock transfected 293 cells (J). Representative fields were photographed three days after treatment.

FIGS. 5A, 5B, 5C and 5D depicts that MNTS-1 binds with high affinity to human trkA, trkB and trkC. Displacement curves using receptor immunoadhesins were determined in the presence of a constant amount of labeled neurotrophin (50 pM for trkA, trkB and trkC; 100 pM for gp75) and increasing amounts of unlabeled competitor; (○) HNGF, (Δ) HBDNF, (□) NT-3, (▲) MNTS-1, (×) S1, (+) D15A. (A) Displacement of $^{125}$I-NGF from human trkA. (B) Displacement of $^{125}$I-BDNF from human trkB. (C) Displacement of $^{125}$I-NT-3 from human trkC (D) Displacement of $^{125}$I-NT-3 from human gp75.

Figure 6A:
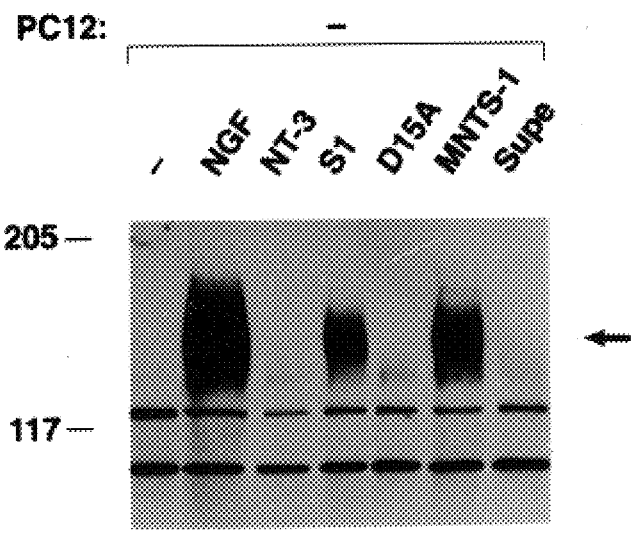
Figure 6B:
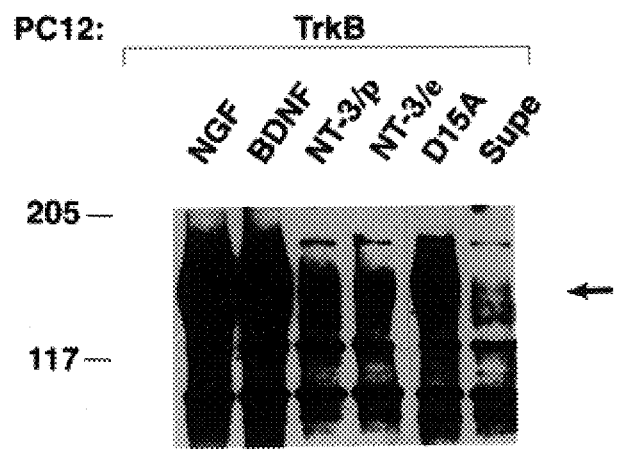
Figure 6C:
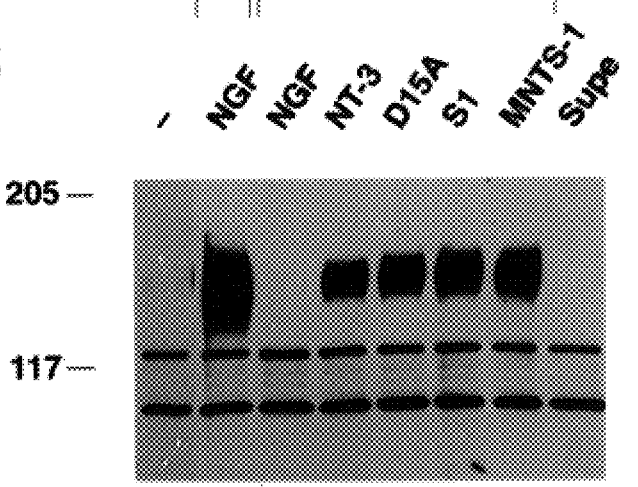

FIGS. 6A, 6B and 6C depicts the autophosphorylation of trkA, trkB and trkC induced by MNTS-1. The PC12 variant cells were exposed to neurotrophic factors and mutants at 25 ng/ml for 5 min. at 37° C. and assayed as described in Experimental Procedures. (A) Response of PC12 cells upon addition of no factor, NGF, NT-3, S1, D15A, MNTS-1 and supernatant of mock transfected 293 cells. (B) Response of PC12/trkB cells upon addition of no factor, NGF, BDNF, NT-3 purified, NT-3 expressed, D15A and supernatant of mock transfected 293 cells. (C) Response of PC12/trkC cells upon addition of no factor, NGF, NT-3, D15A, S1, MNTS-1 and supernatant of mock transfected 293 cells. Numbers below neurotrophic factors indicate type of antiserum used for immunoprecipitation,443 is a pan-trk antiserum, 656 is a trkC specific antiserum.

Figure 7:
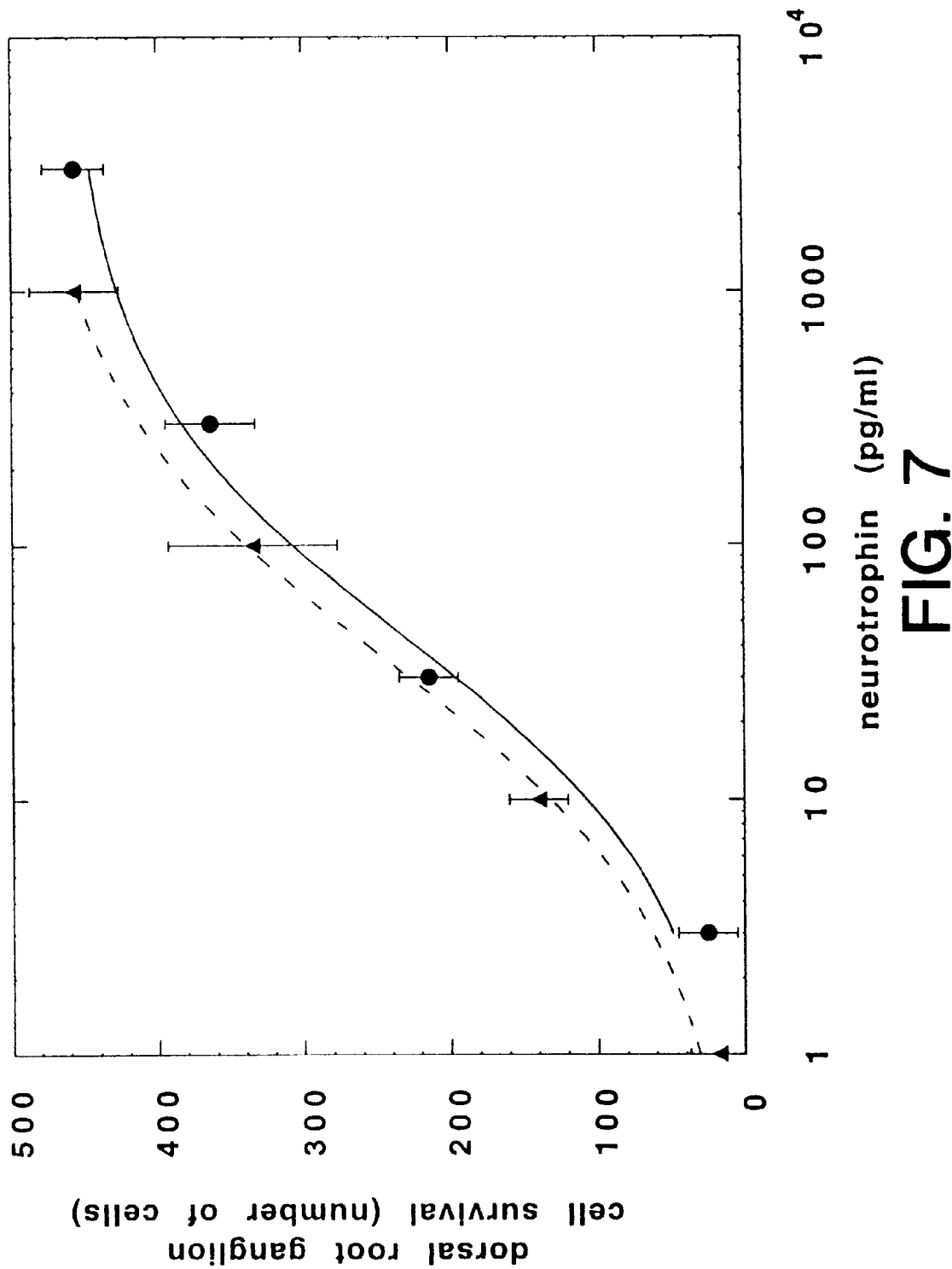

FIG. 7 depicts that MNTS-1 is as potent as cocktail of NT-3/BDNF/NGF on survival of DRG neurons. Dose dependency of survival of neurons from DRG. Number of cells supported by cocktail of NT3/BDNF/NGF (1:1:1) (●) and MNTS (▲). Results are expressed as mean of triplicate determinations ±SD. Data was fit to a four-parameter equation for MNTS-1 (dashed line) and cocktail (solid line). The calculated EC-50 values for MNTS-1 and cocktail were 36 pg/ml and 44 pg/ml, respectively.

Figure 8:
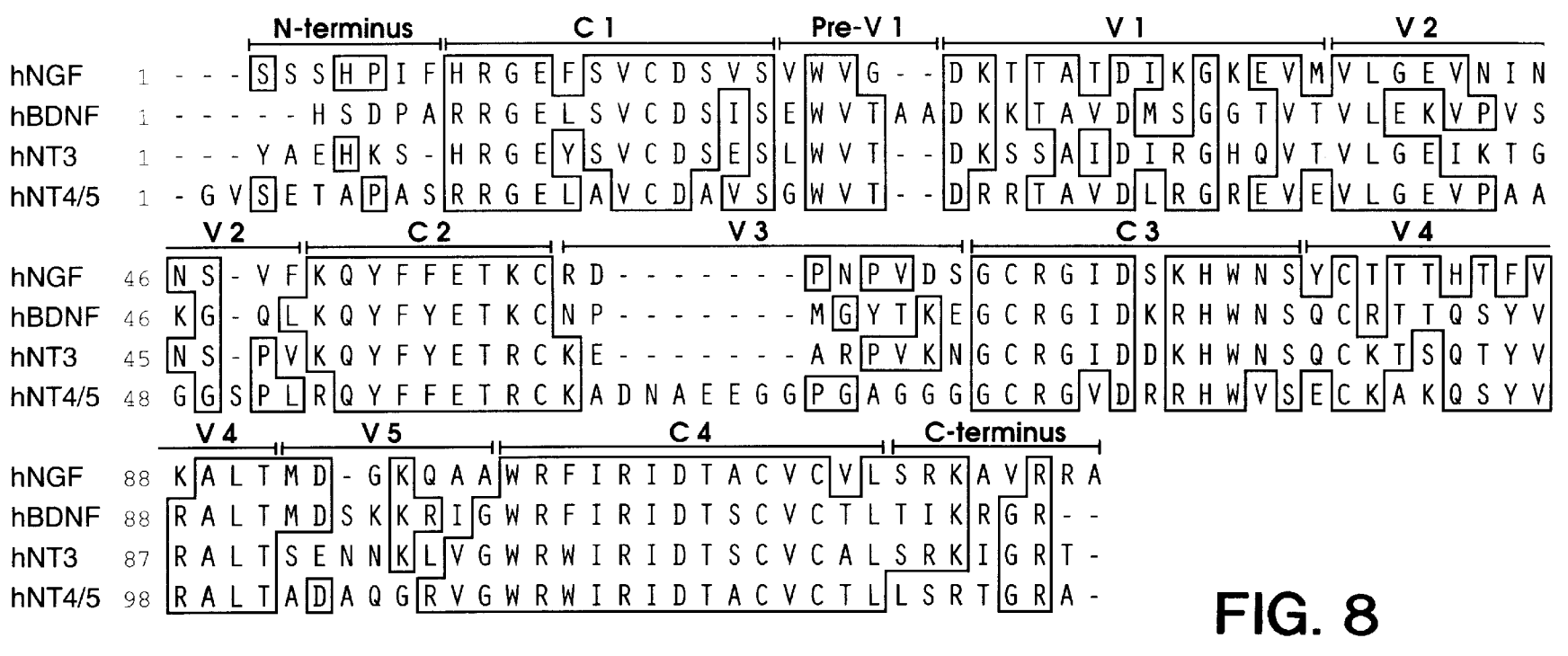

FIG. 8 depicts the homology, variable regions and constant regions of the various neurotrophins. NGF (SEQ ID NO:3), BDNF (SEQ ID NO:4), NT3 (SEQ ID NO:2) and NT4/5 (SEQ ID NO:5) are shown, with the variable regions boxed.

Figure 9A:
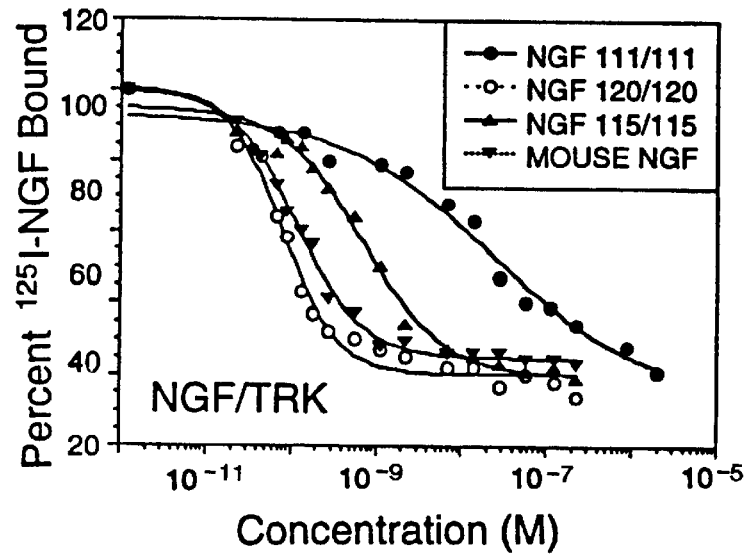
Figure 9B:
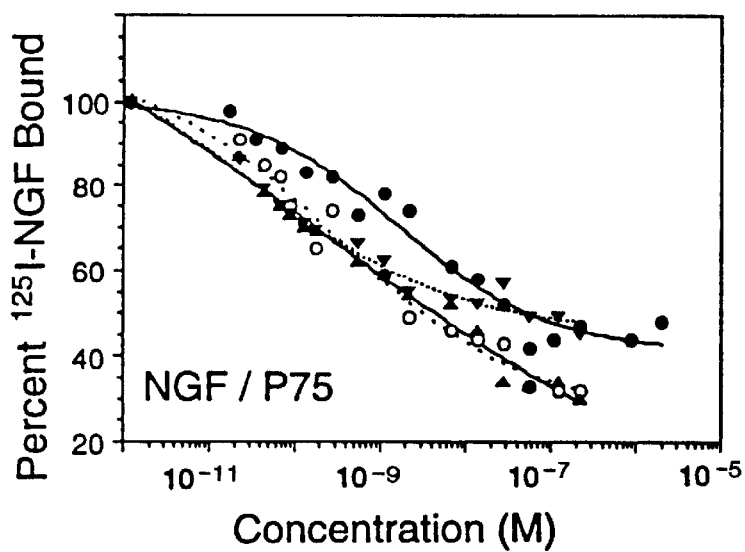
Figure 9C:
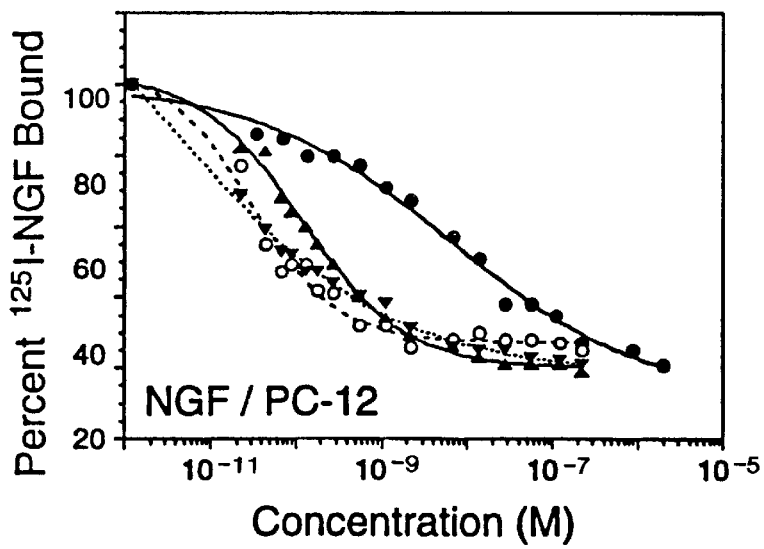

FIGS. 9A, 9B and 9C depict the competition displacement of [$^{125}$I]hNGF from either trkA, p75, or trkA+p75 receptors by increasing concentration of purified N-terminally-modified forms of hNGF. Upper (9A), middle (9B), and lower (9C) panels represent displacement from MH3T3, A875 melanoma, and PC12 pheochromocytoma cells expressing trkA, p75, and trkA+p75 receptors, respectively. The competing ligands are as indicated: (●—●) 111/111= homodimers of (10–118)hNGF; (○—○)118—118= homodimers of (1–118)hNGF; (▲—▲) 115—115= homodimers of (6–118)hNGF;(▼—▼) mouse NGF= homodimers of (1–118)mNGF. Receptor binding was performed at 4° C. and analyzed as described in the examples. The data presented represents the total binding (specific and non-specific) and is representative of at least three separate binding experiments for each cell line. The $IC_{50}$ for this experiment is given in Table 5.

Figure 10A:
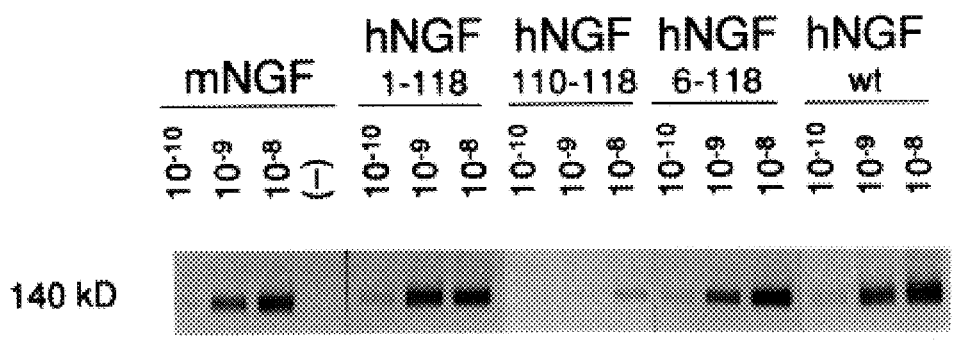
Figure 10B:
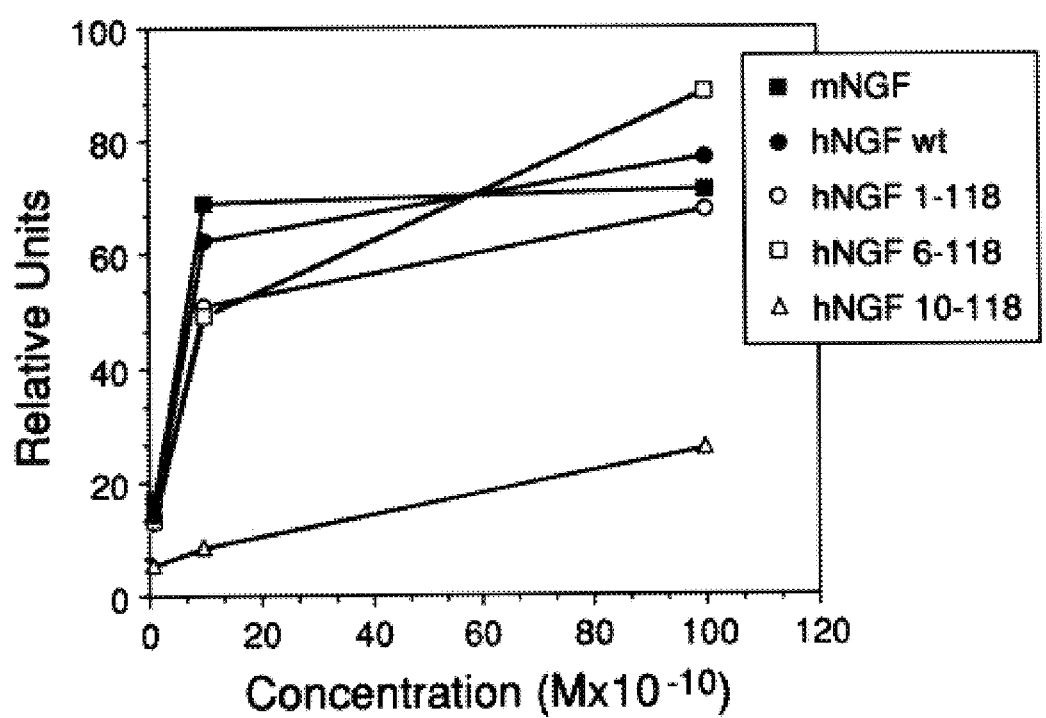

FIGS. 10A and 10B depicts the autophosphorylation of trkA induced by N-terminally truncated forms of hNGF. Upper panel (10A) shows the intensity of the autophosphorylation of the $p140^{trkA}$ band as a function of molar concentration of hNGF variant while the lower panel (10B)

represents quantitation of the optical density of each band determined by reflective densitometry. The autophosphorylated p140$^{trkA}$ band was identified by anti-trkA immunoblotting on nitrocellulose following immunoprecipitation with antiphosphotyrosine. The data presented are representative of two independent experiments.

Figure 11A:
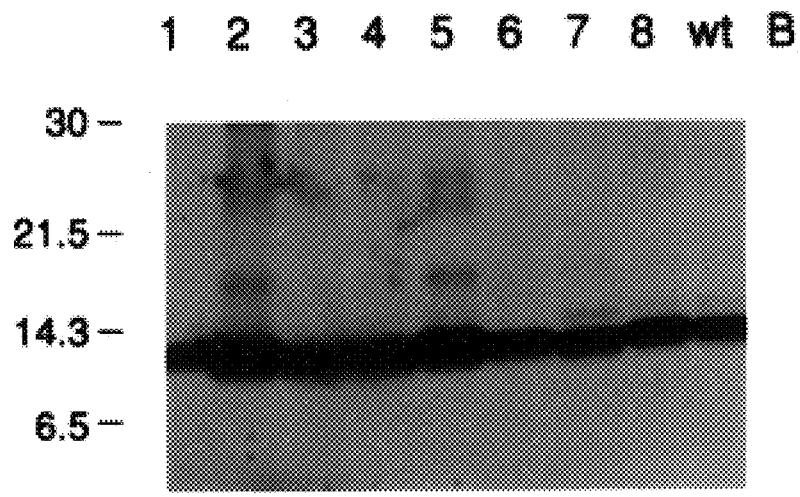
Figure 11B:
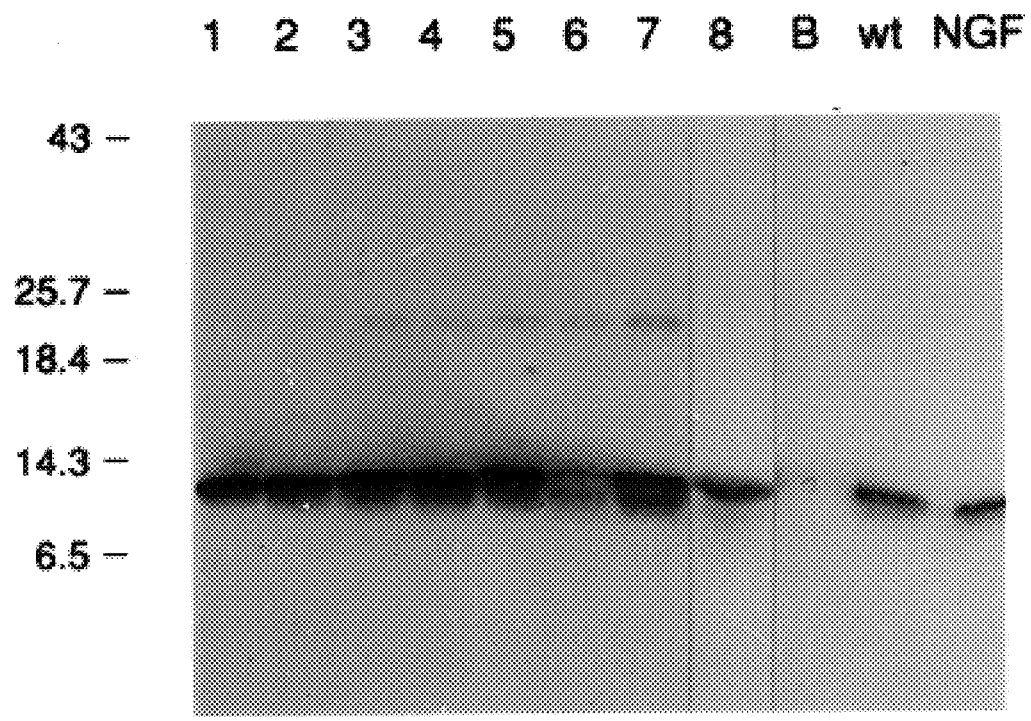
Figure 12A:
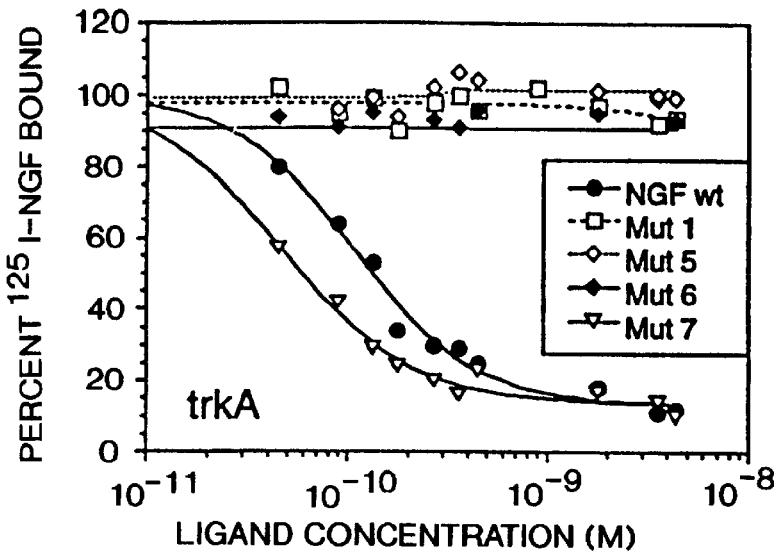
Figure 12B:
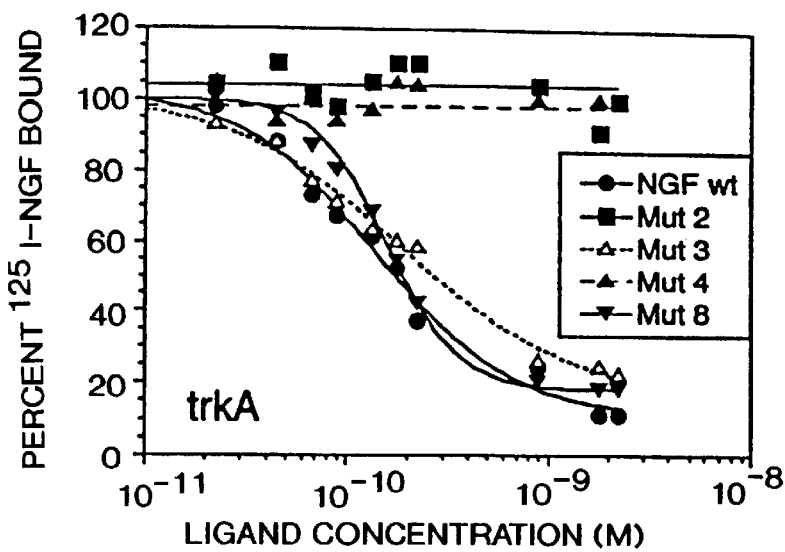
Figure 12C:
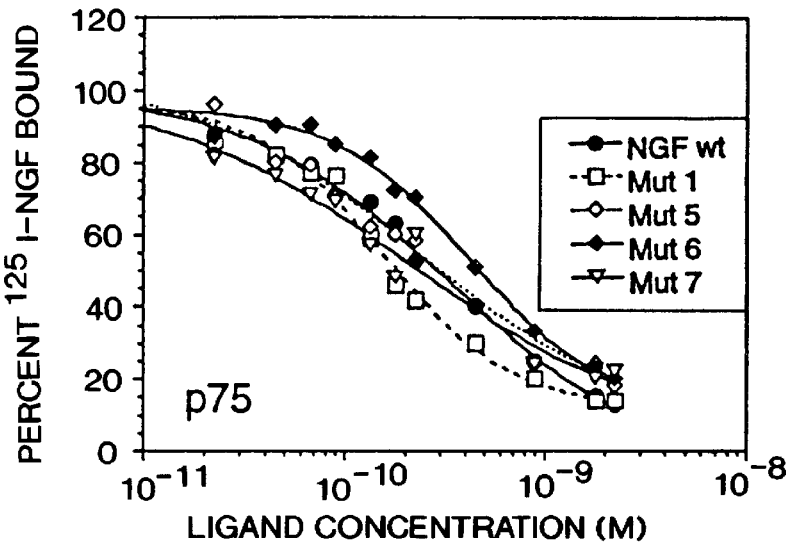
Figure 12D:
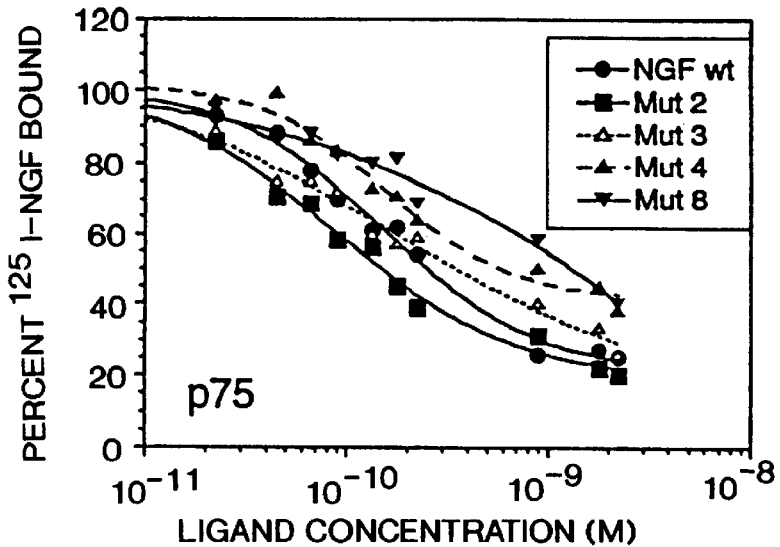
Figure 12E:
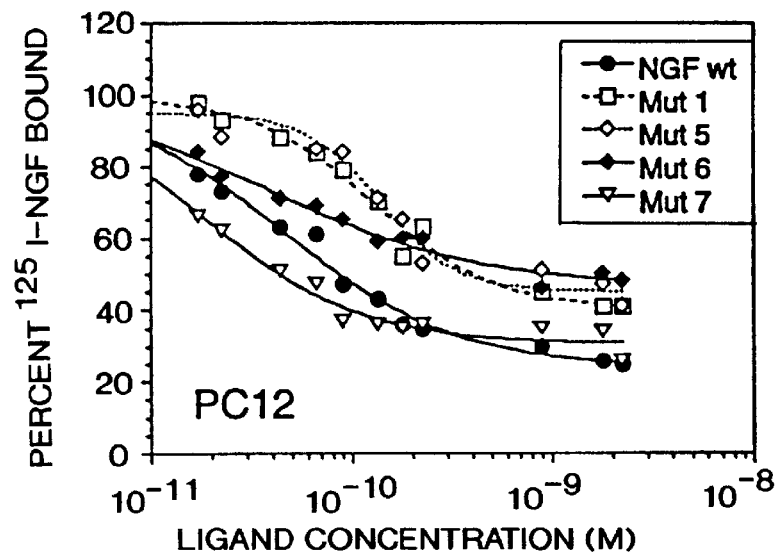
Figure 12F:
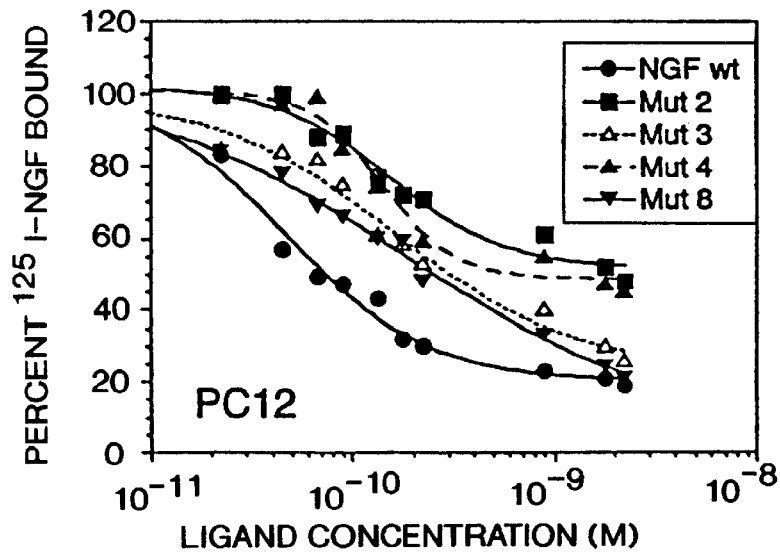

FIGS. 11A and 11B depicts the expression and protein analysis of hNGF mutants. Panel A represents an autoradiograph of metabolic labelled mutants 1–8 (See Table 1 for description) separated by SDS-PAGE. Mutants were transiently expressed in human 293 cells and labelled with $^{35}$S-methionine and cysteine. Conditioned media was immunoprecipitated with a purified rabbit anti-hNGF polyclonal antibody, and the precipitates analyzed by SDS-PAGE as described in the examples. The lanes labelled wt or B represents transfection of cells with wild type (1–120)hNGF expressing vector or AdVA vector alone, respectively. Panel B represents Western immunoblot analysis of approximately 0.1 μg of non-labelled mutant or wild type hNGF. These samples are taken from conditioned media following transfection in parallel to the metabolic-labelled cells described above. Immunoblotting was performed with the same anti-hNGF polyclonal antibody described in panel A. The results can be contrasted with the variable detection of the mutants immunoblotted in parallel in the same experiment and reacted with a specific hNGF monoclonal antibody as shown in FIG. 18. The lane labelled NGF represents the signal from 0.1 μg of purified (1–120)hNGF. The left axis of both panels indicates the relative mobility of the molecular mass markers in kD.

FIGS. 12A, 12B, 12C, 12D, 12E and 12F depict the competition displacement of [$^{125}$I]hNGF from cells expressing trkA (top panels, 12A and B), p75 (middle panels, 12C and 12D), and p75+trkA (bottom panels, 12E and 12F) by increasing concentrations of hNGF mutants. For clarity the data is divided into two panels for each cell line. For comparisons of relative binding affinity, four mutants and the hNGF wild type control were tested in each cell line in one experiment. Each of the two panels is representative of at least two separate binding experiments from one transfection and one binding experiment from an additional transfection. The binding experiments were performed at 4° C. as described in the examples. Total binding is presented as in FIG. 12. The IC$_{50}$ relative to wild type hNGF is presented in Table 5.

Figure 13A:
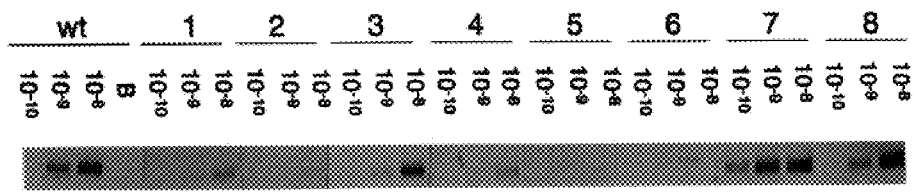
Figure 13B:
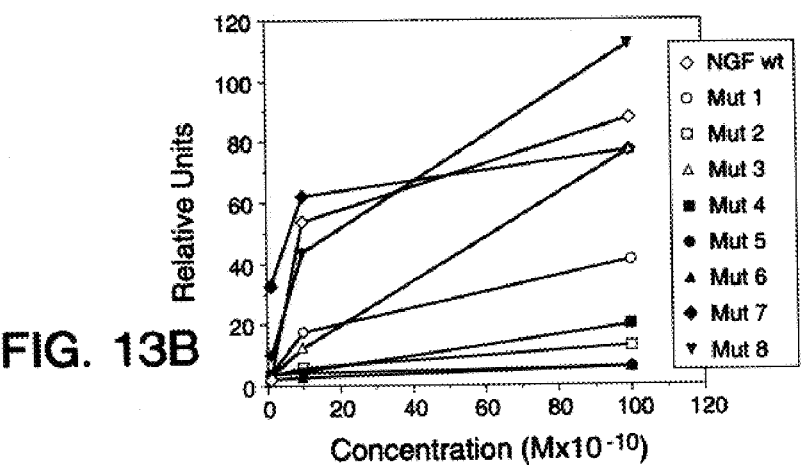

FIGS. 13A and 13B depict the autophosphorylation of trkA elicited by hNGF mutants. The top panel (13A) represents an autoradiograph of p140$^{trkA}$ following stimulation of trkA-expressing cells by the indicated concentrations of mutant or wild type hNGF. Levels of trkA autophosphorylation were determined as in FIG. 10. The bottom panel (13B) is the densitometric quantitation of the above autoradiograph. The data presented is representative of at least two experiments comparing the trkA autophosphorylation elicited by all of the mutants within one experiment, and is consistent with data from other experiments comparing 3–4 mutants per experiment with hNGF.

Figure 14:
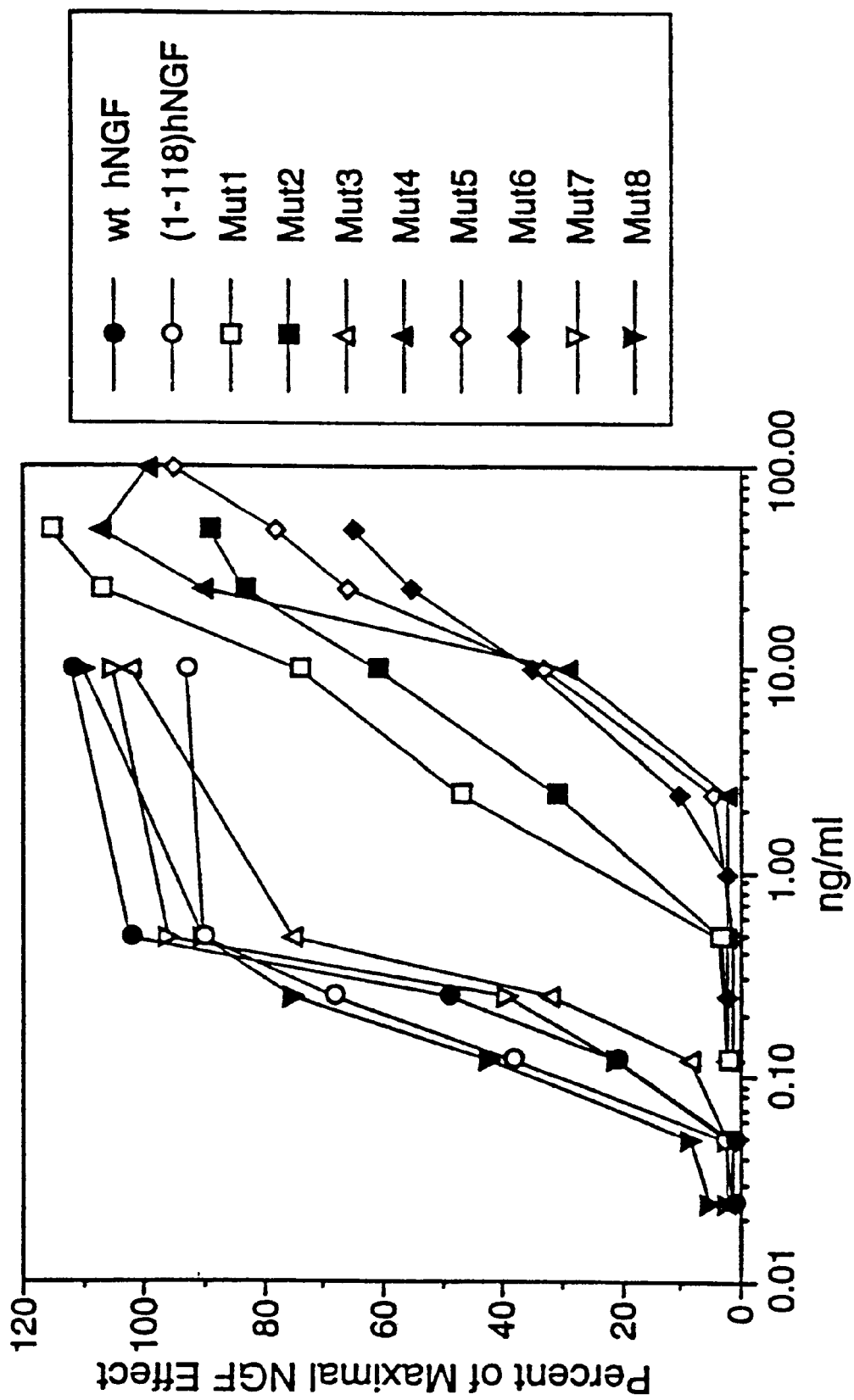
Figure 15A:
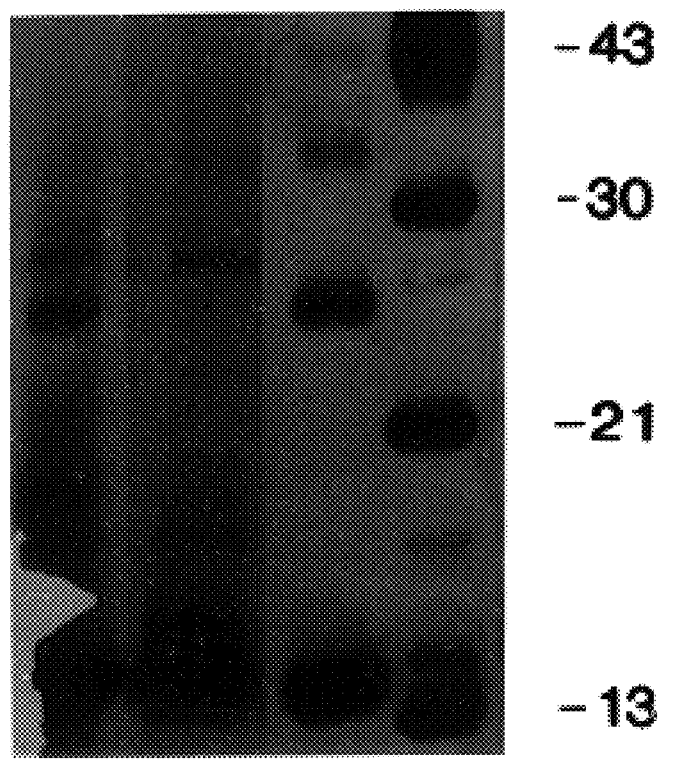
Figure 15C:
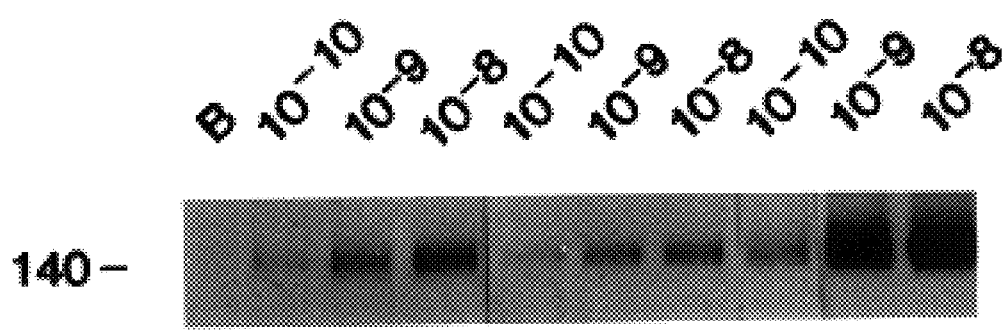
Figure 15B:
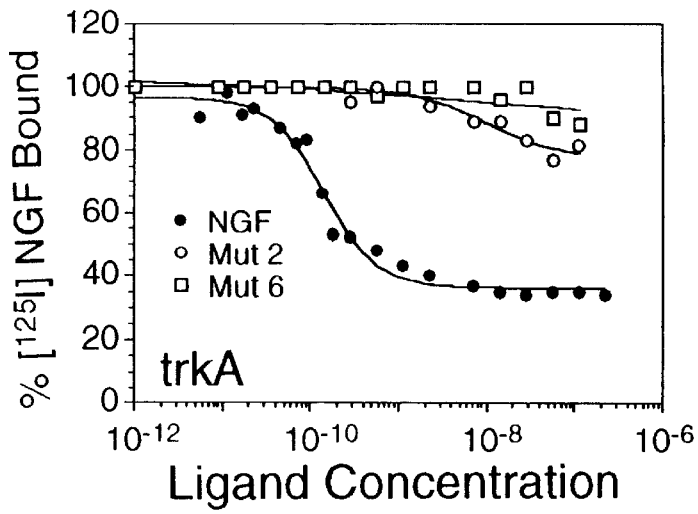
Figure 15D:
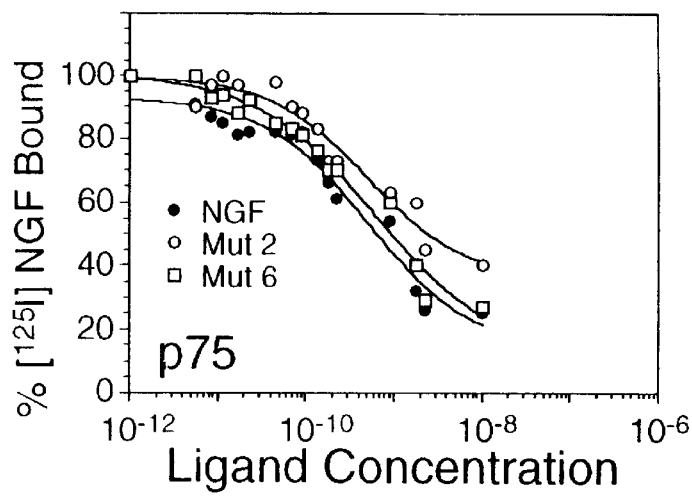
Figure 15E:
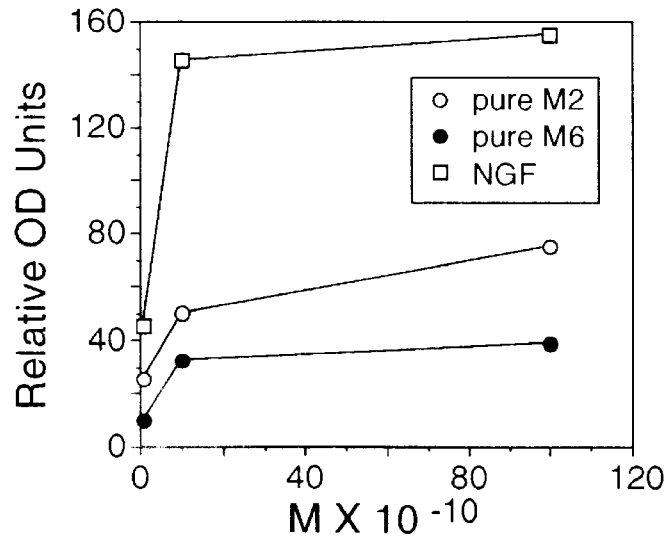

FIG. 14 depicts the biological activity of hNGF mutants determined by PC12 cell neurite outgrowth. PC12 cells were grown in the presence of the indicated concentrations of mutant or wild type hNGF for 48 hrs. The percentage of the total cells within a given microscope field extending neurites is presented normalized to the maximal response elicited by (1–118)hNGF as described in the examples. The values presented are the average of at least two determinations per mutant.

FIGS. 15A, 15B, 15C, 15D, and 15E depict the characterization of purified N-terminal region mutants. A. Silver stain of SDS-PAGE (15% acrylamide) of 1 μg of purified H4D mutant 2 (lane 1), purified hNT3/hNGF N-terminal chimeric mutant 6 (lane 2), partially purified (1–120)hNGF (lane 3-N), and molecular mass markers in kD (lane 4-M). Details of the purification and analysis presented in the Materials and Methods section. B. Competition displacement of [$^{125}$I]hNGF by purified H4D mutant 2, hNT3/hNGF N-terminal chimeric mutant 6, and purified (1–120)hNGF. Top panel (15B) represents binding to NIH3T3 cells expressing trkA, bottom panel (15D) shows binding to A875 cells (p75). C. Top panel (15C) represents concentration dependence (M) of p140$^{trkA}$ autophosphorylation detected by antiphosphotyrosine immunoblot as in FIGS. 10 and 13. Bottom panel (15E) presents densitometric quantitation of the immunoblot data.

Figure 16A:
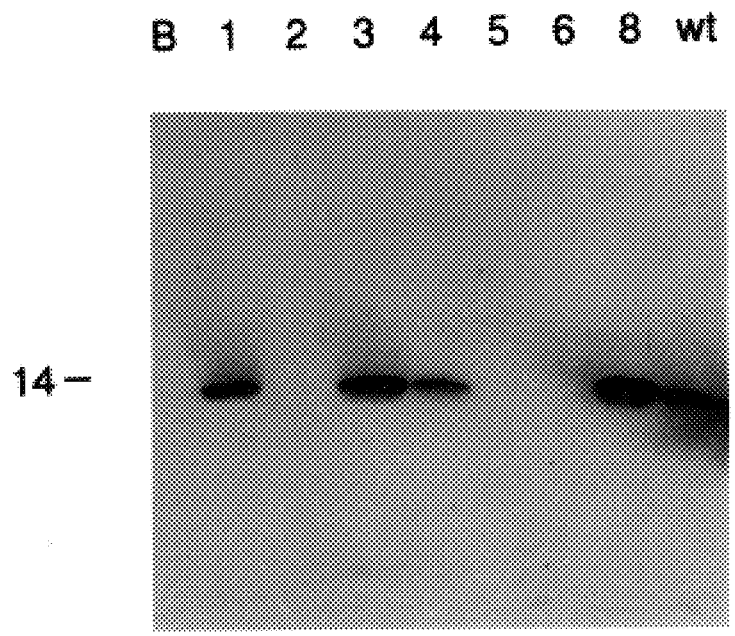
Figure 16B:
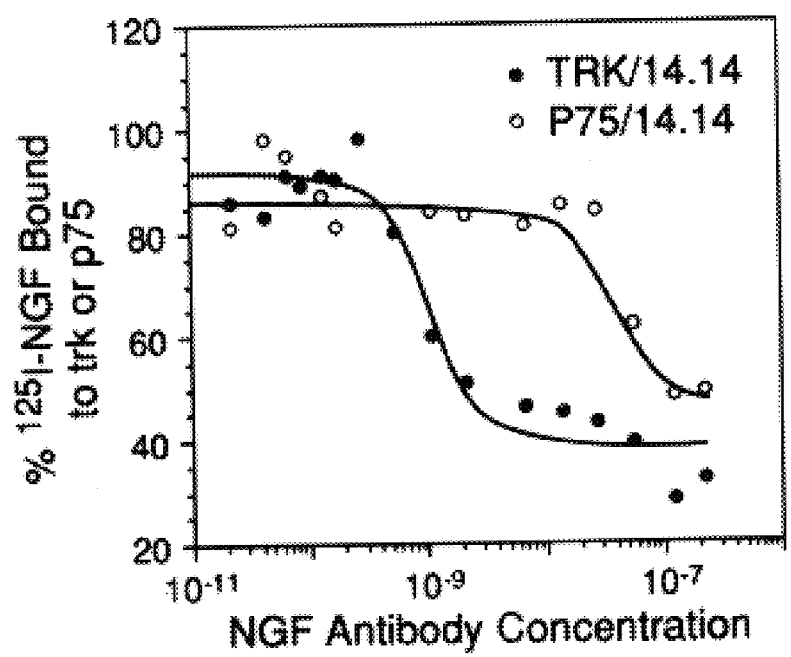

FIGS. 16A and B depict the monoclonal antibody interaction with the N-terminal region of hNGF. A. Immunoblot of 0.1 μg of mutants 1–6 and 8 (mutant 7 omitted because of low concentration), hNGF (wt) and control transfected conditioned media (B). Conditioned media was applied to SDS-PAGE, immunoblotted onto nitrocellulose, and reacted with anti-hNGF monoclonal antibody 14.14. The relative mobility of the mutants is shown as 14 kD. B. Competition displacement of 25 pM[$^{125}$I]hNGF from either trkA-expressing or p75-expressing cells by increasing concentrations of the same monoclonal antibody used in panel A.

Figure 17:
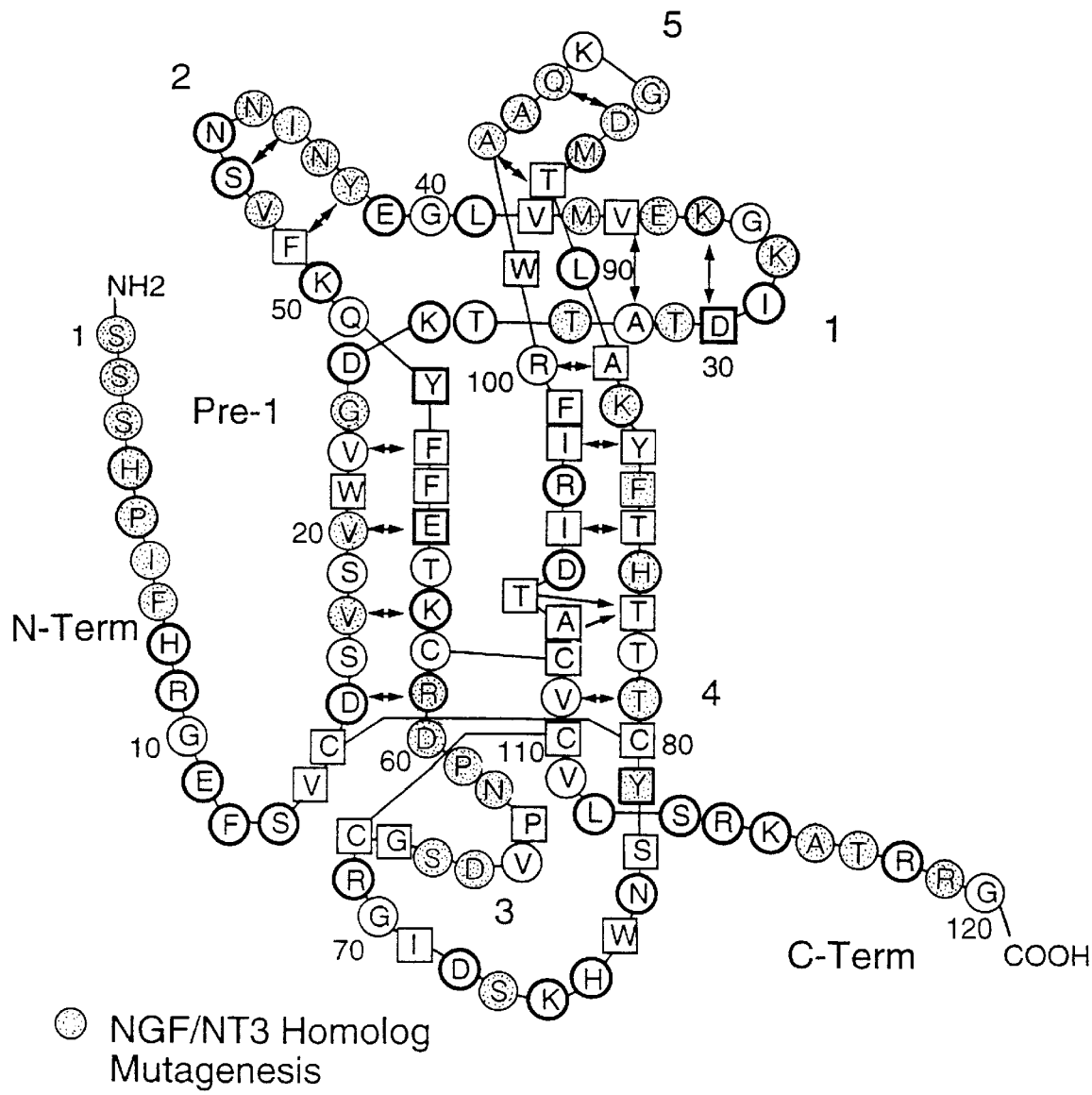

FIG. 17 depicts a schematic drawing of a hNGF monomer, based on the x-ray crystal structure of murine NOF, which indicates the primary amino acid sequence (SEQ ID NO:3), the basic features of the secondary structure and residues modified by mutagenesis. The yellow shaded residues indicate those which differ between hNGF and hNT3, and were replaced by the corresponding hNT3 residues in hNGF as domain swaps. The large black numbers located near blocks of 5–8 yellow residues numerate the particular neurotrophin variable region. These variable regions also include the amino and carboxy termini. The red shaded residues indicate those mutated singly or in pairs, and represent amino acids mostly exposed to the solvent.

Figure 18A:
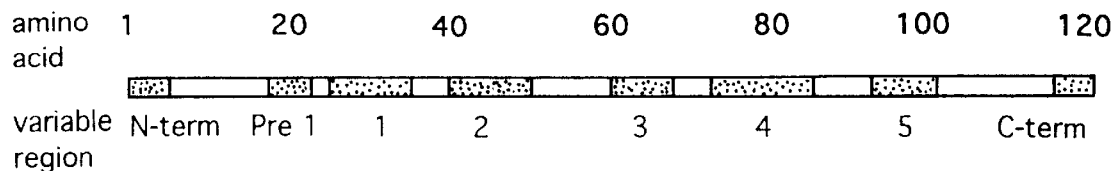
Figure 18B:
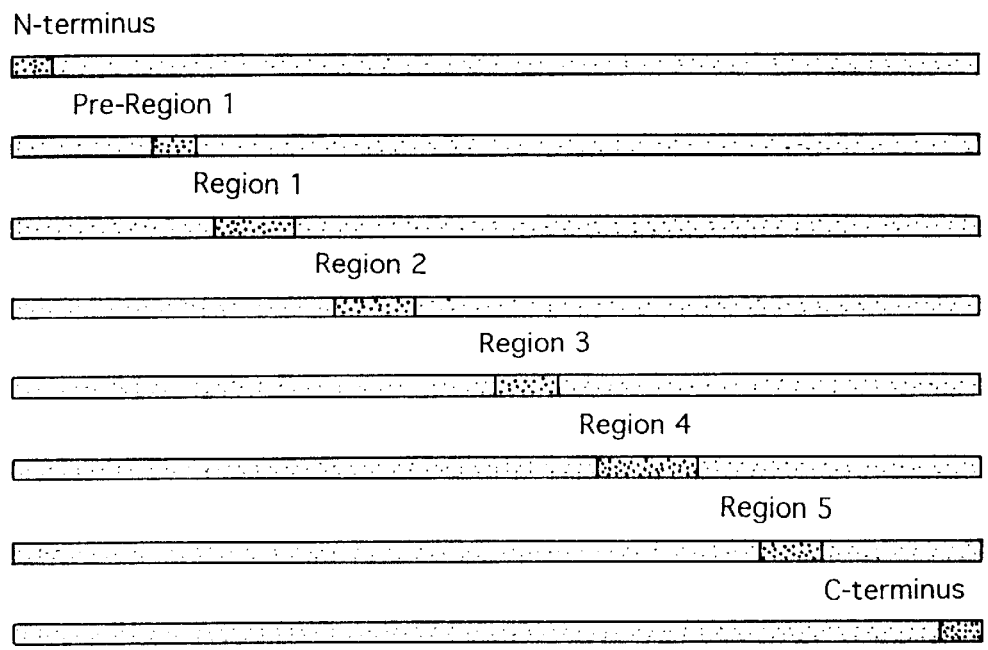
Figure 19A:
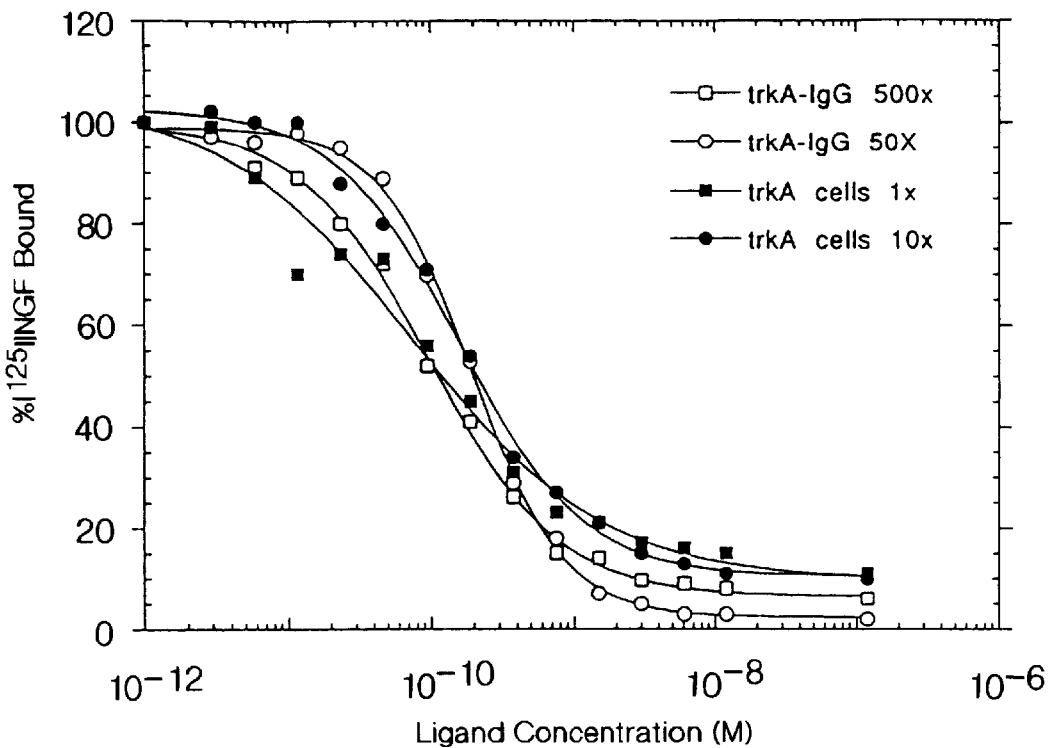
Figure 19B:
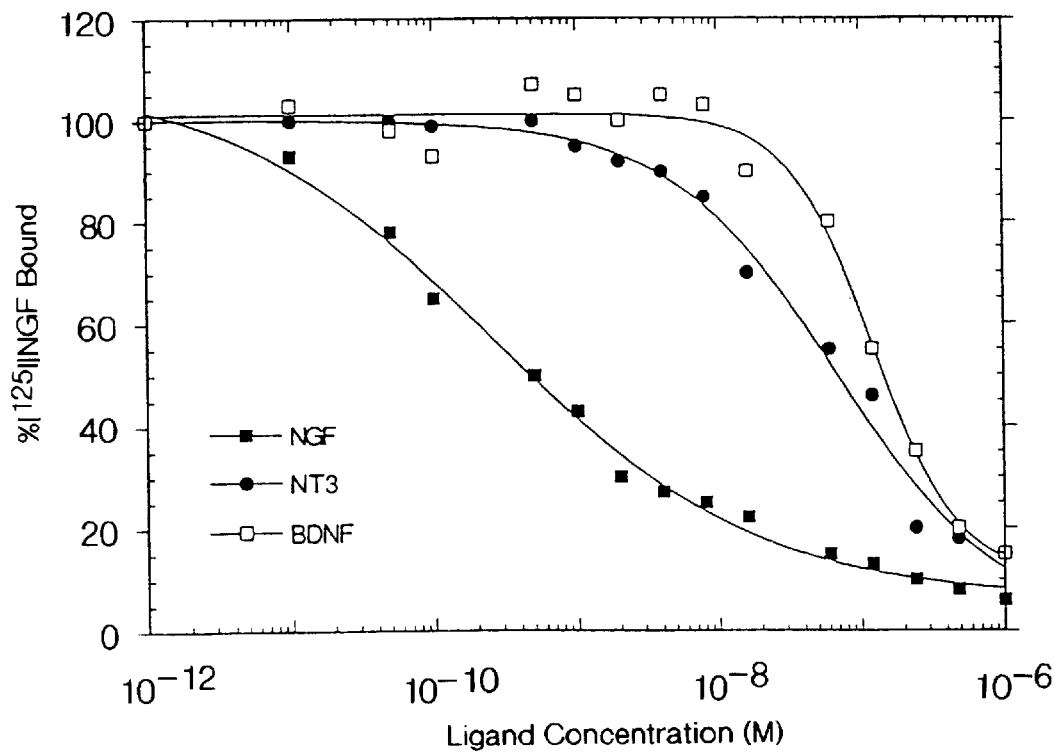

FIGS. 18A, 18B and 18C show the hNGF organization. FIG. 18A depicts the position of variable domains within the primary sequence of hNGF. FIG. 18B depicts the variable domain chimeric mutants of hNGF, containing a single variable domain of hNT3. The list, 18C, contains the specific residues of hNGF replaced by hNT3 within a given mutant FIGS. 19A and 19B depict the characterization of a new receptor binding procedure used to analyze structural variants of hNGF. A) A comparison of the binding properties of trkA-IgG immunoadhesion-based assays with those of holo-trkA receptors expressed in NIH3T3 cell lines. The trkA-IgG competition binding profiles are very similar to those of holo-trkA cell lines (19A) while trkA-IgG displays the same neurotrophin selectivity (19B; NGF>>NT3>BDNF). Bnding data now presented utilizes individual trk A, B, C or p75-IgG immunoadhesion assays. The receptor binding characteristics for several variants was verified in holo-trkA cell binding assays.

Figure 20A:
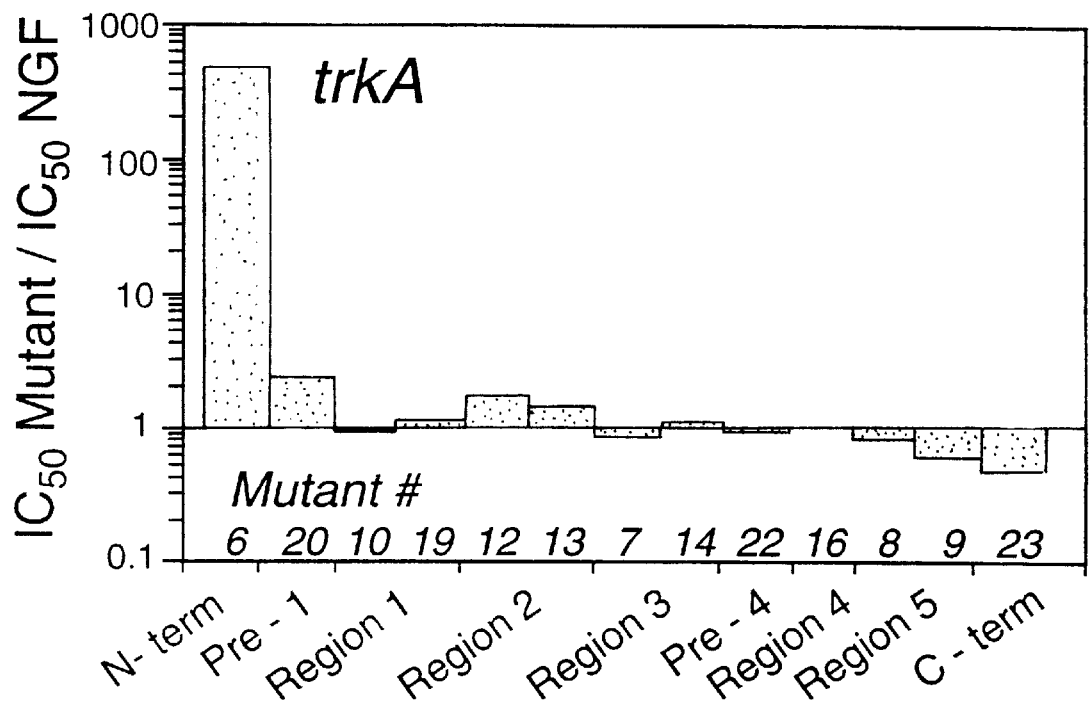
Figure 20B:
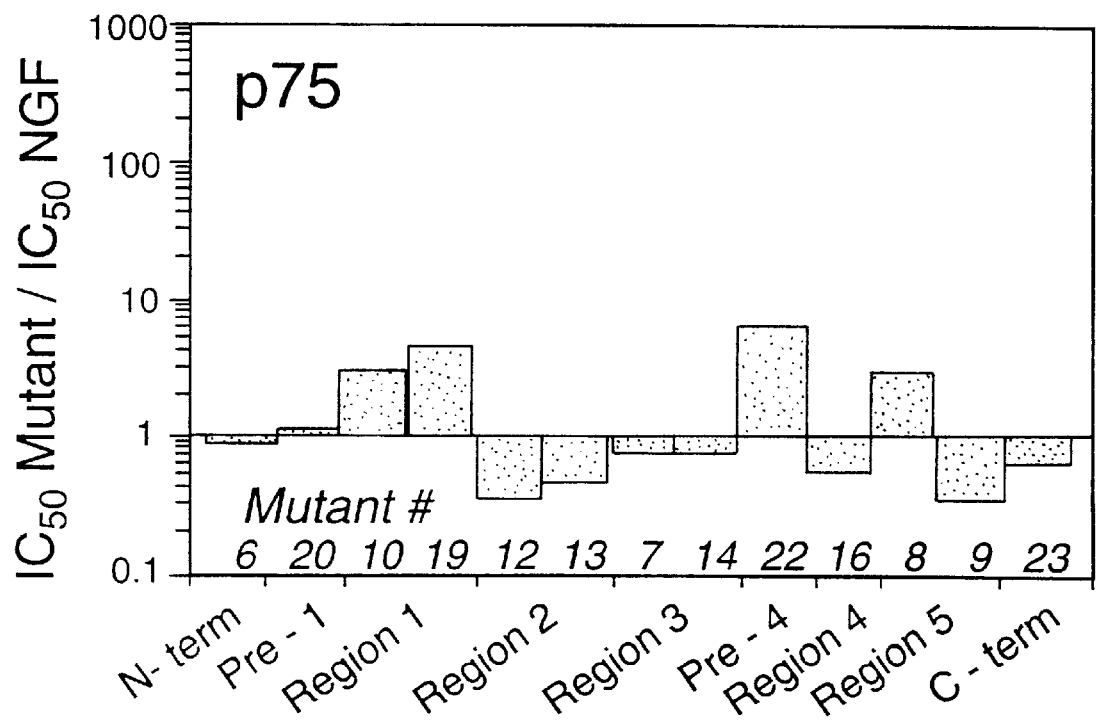

FIGS. 20A and 20B depict the binding of hNGF/hNT3 chimeric mutants to trkA-IgG and gp75 receptors. The relative affinities of the mutants are plotted as the ratio of the IC$_{50}$ of the mutant to that of hNGF taken from competition binding curves. The average ratio is presented from three independent binding experiments. The NGF/NT3 N-terminal domain swap mutant (mutant 6) results in a significant loss of trkA binding while gp75 binding is unaffected. These results are consistent with the data obtained from holo-trkA binding in cells at 4° C. (FIG. 18B,C). Chimeric mutants containing the first beta-turn of NT3 (mutants 10 and 19) have lost 4-fold potency in binding to gp75. Alanine replacement of basic residues in the first beta-turn (mutant 21) or in the C-terminus (mutant 24) results in significant loss of gp75 binding.

Figure 21A:
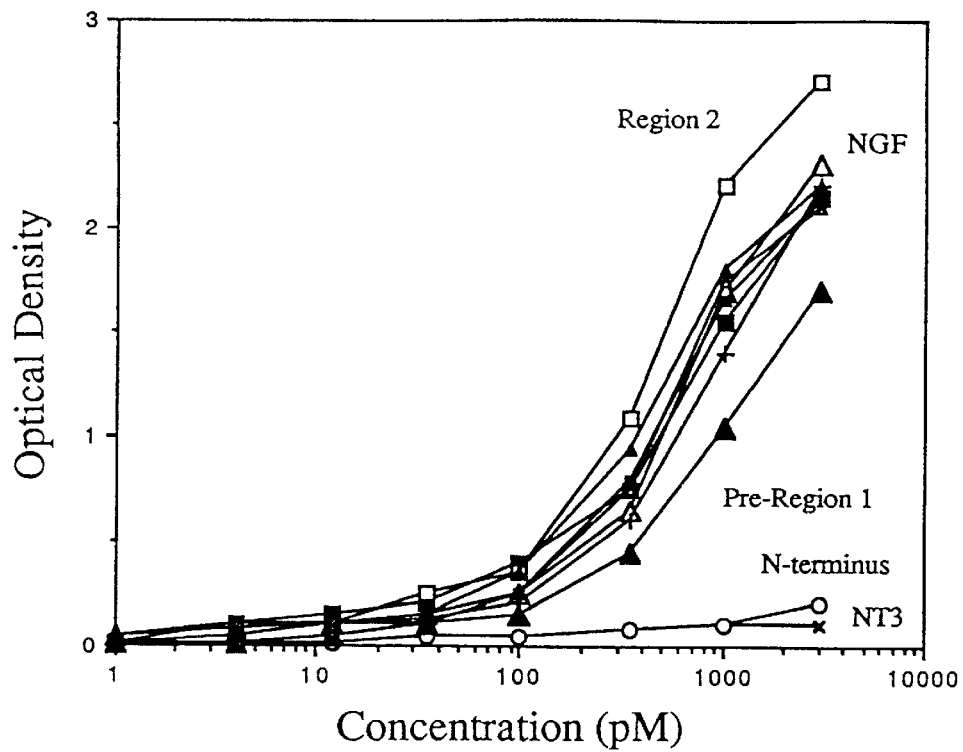
Figure 21B:
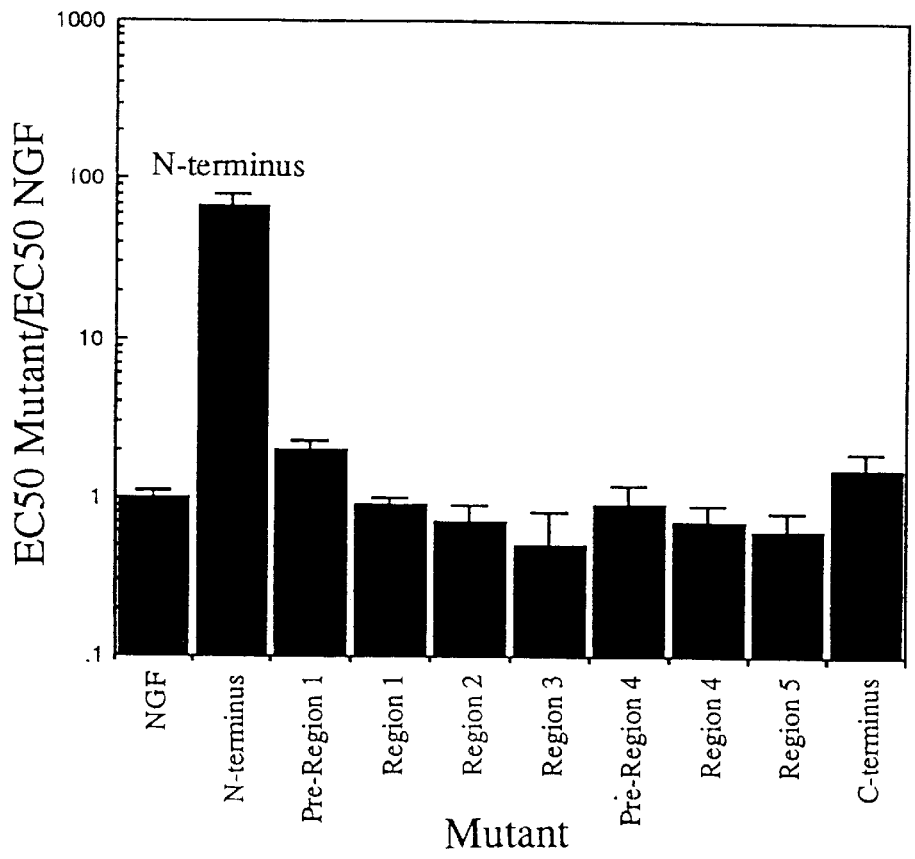

FIGS. 21A and 21B depict the ability of the hNGF/hNT3 chimeric mutants to elicit trkA tyrosine kinase autophosphorylation and PC12 cell neurite outgrowth, respectively. TrkA-expressing CHO cells were stimulated with hNGF, hNT3 or hNGF/hNT3 domain-swapped chimeric mutants and autophosphorylation was determined by a phosphotyrosine-ELISA assay ($OD_{450/650}$). Consistent with the trkA binding, little trkA autophosphorylation is stimulated by the N-terminal hNGF/hNT3 chimeric mutant. A 2–3- fold loss of activity results from the domain swap within the pre-beta turn 1 region (V18, V20, G23), indicating a possible role of these residues in determining NGF-trkA specificity. For PC12 cell differentiation, the $EC_{50}$ for neurite outgrowth was determined for all mutants and expressed as a ratio with the $EC_{50}$ for hNGF. Again, the greatest effect is observed with the N-terminal hNGF/hNT3 domain swap mutant, however, loss of bioactivity is also observed with the pre-beta turn 1 region, consistent with the trkA binding and autophosphorylation.

Figure 22A:
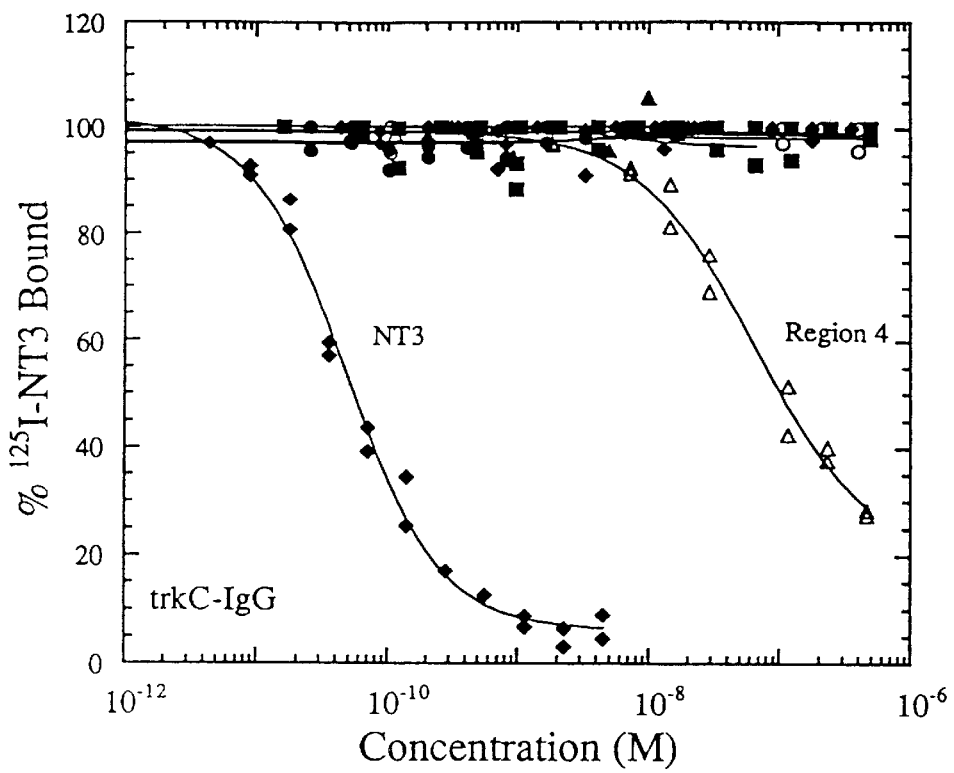
Figure 22B:
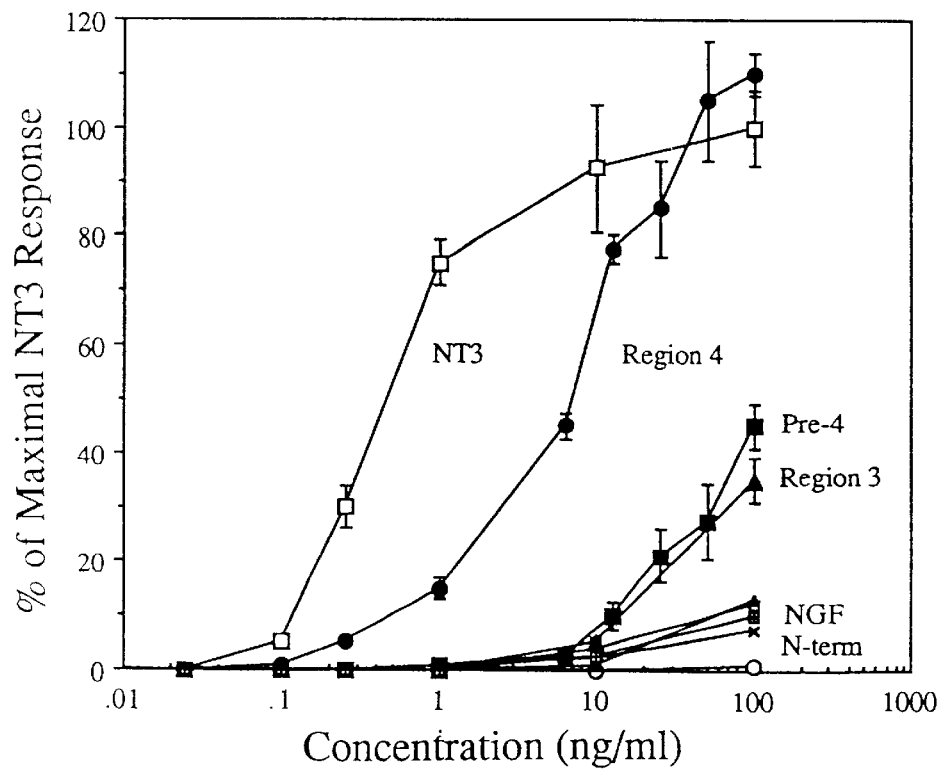

FIGS. 22A and 22B depict the pan-neurotrophic activity of hNGF/hNT3 domain-swap mutants. The activity is measured by trkC-IgG competition binding and neurite outgrowth in trkC-transfected PC12 cells. Competition displacement of [$^{125}$I]hNT3 is observed only for hNT3 ($IC_{50}$=45 pM) and the variable region 4 hNGF/hNT3 domain swap mutant (Mutant 16; $IC_{50}$=80 nM). Similarly, the hNGF/hNT3 domain swap in variable region 4 results in significant neurite outgrowth in trkC-transfected PC12 cells that do not respond to hNGF. Comparison of the trkA-dependent binding, autophosphorylation, and PC12 cell activities for mutant 16 (FIGS. 19, 20) reveals little loss of endogenous hNGF-like activity. The N-terminal domain-swap mutant (mutant 6), containing the N-terminus of NT3, does not interact with trkC.

Figure 23:
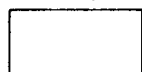
Figure 23:
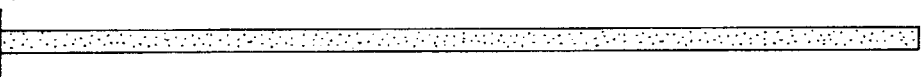
Figure 23:

FIG. 23 depicts the two N-terminal domain-swap mutants: hNT3-NH2/hNGF is mutant 6 and contains hNT3 residues 1–6 (YAEHKS-), replacing hNGF residues 1–7, on a remaining backbone of hNGF. hNGF-NH2/NT3 is P2 (S1) and contains hNGF residues 1–7 (SSSHPIF-), replacing hNT3 residues 1–6, on a remaining backbone of hNT3.

Figure 24A:
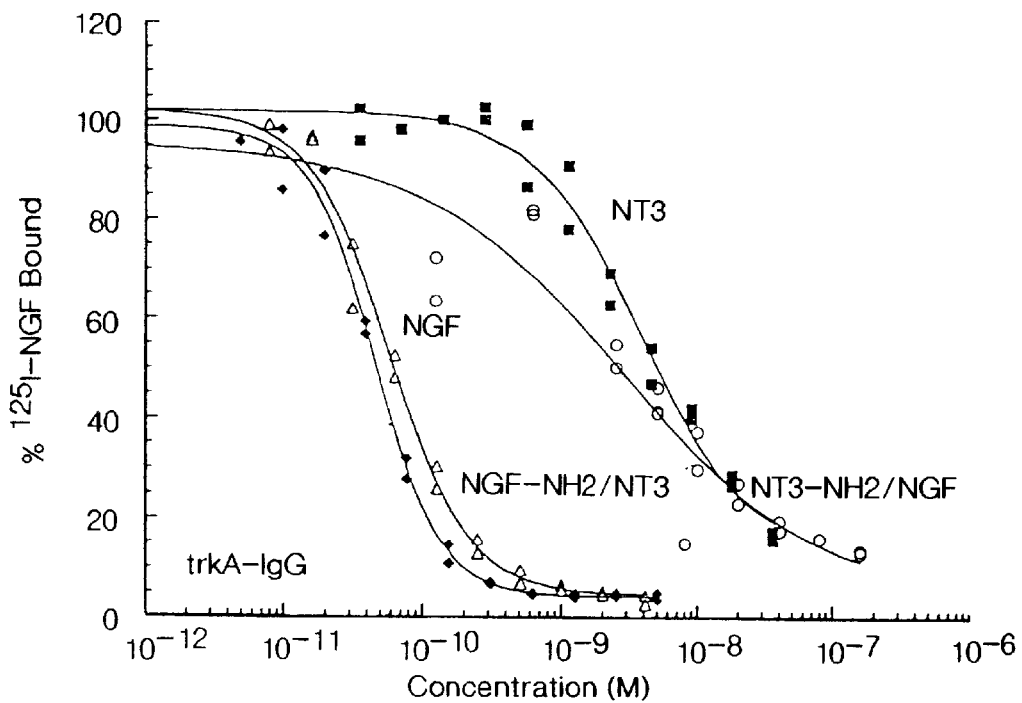
Figure 24B:
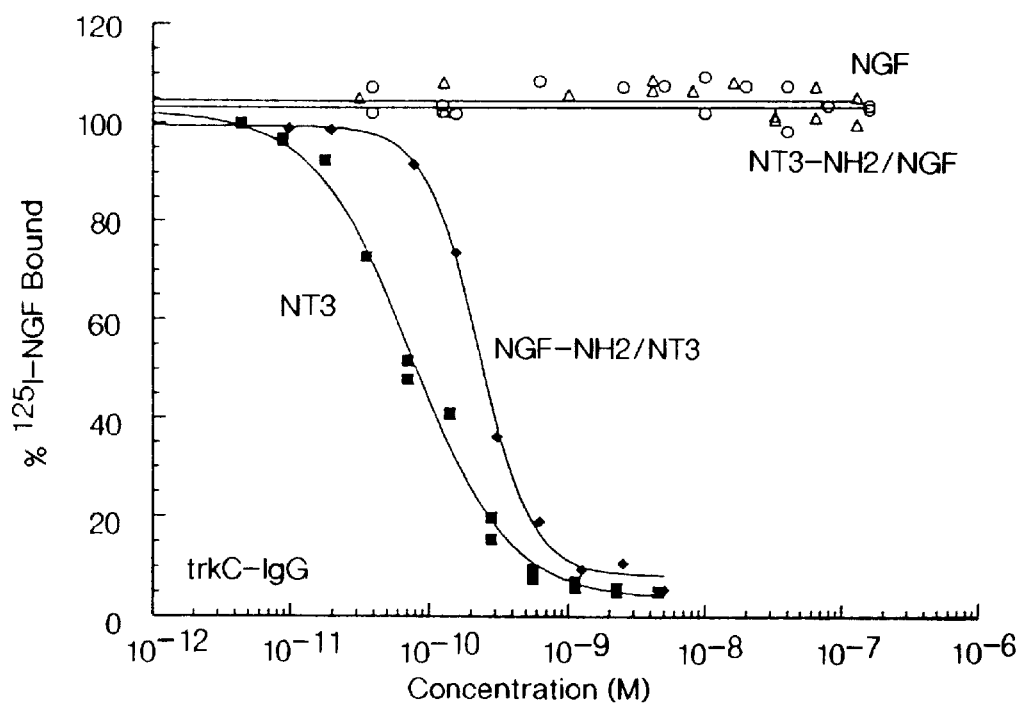
Figure 24C:
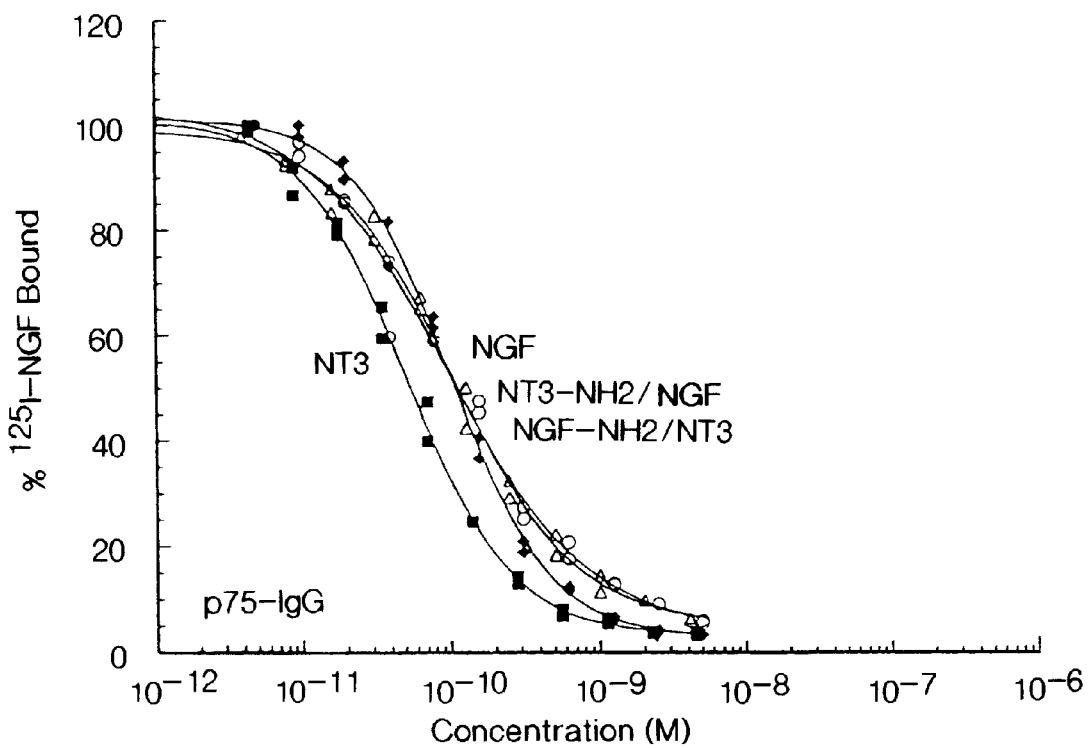

FIGS. 24A, 24B and 24C depict the pan-neurotrophin receptor binding activity of P2 (S1) with trkA, trkC, and gp75, respectively. Competition binding assays were performed by displacement of [$^{125}$I]hNGF or [$^{125}$I]hNT3 from the receptor-IgG immunoadhesions by the indicated factor. P2 (NGF-NH$_2$/NT3), the N-terminal domain-swap mutant of hNT3 containing the hNGF N-terminus, displays hNGF-like trkA binding activity while retaining trkC activity. NT3-NH$_2$/NGF (mutant 6), the converse N-terminal domain-swap mutant of hNGF containing the hNT3 N-terminus, displays reduced trkA binding and no binding to trkC.

Figure 25A:
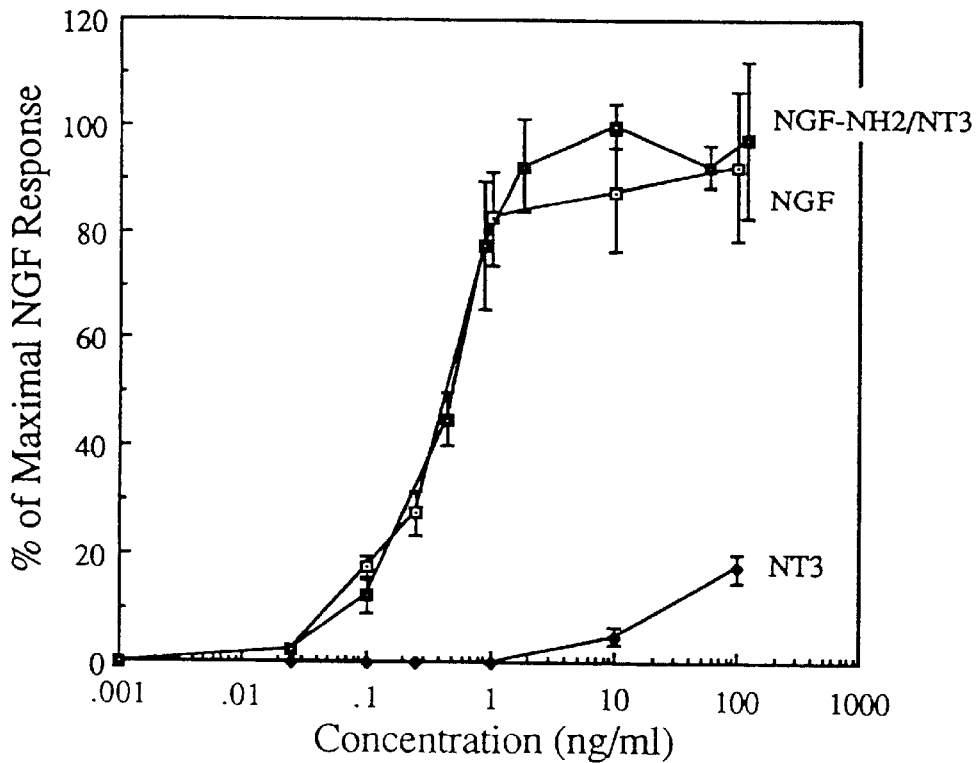
Figure 25B:
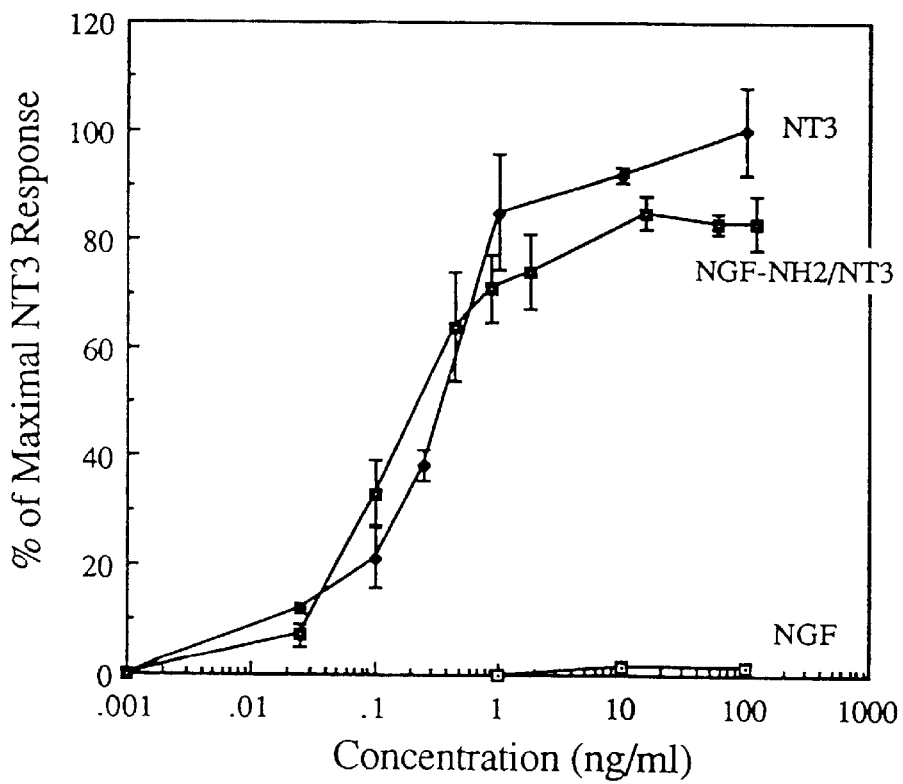

FIGS. 25A and 25B depict the pan-neurotrophin bioactivity of P2 (S1) in normal trkA expressing PC12 cells and trkC-transfected PC12 cells with reduced hNGF response, respectively. The percent of PC12 cells bearing neurites at a given concentration of neurotrophin or variant was normalized to the maximal response elicited by the natural neurotrophin. The $EC_{50}$ for P2 (NGF-NH$_2$/NT3) in the trkA PC12 cells is 0.4 ng/ml (15 pM) and 0.2 ng/ml (7 pM) in the trkC-transfected PC12 cells, similar to the $EC_{50}$ for hNGF and hNT3, respectively.

Figure 26A:
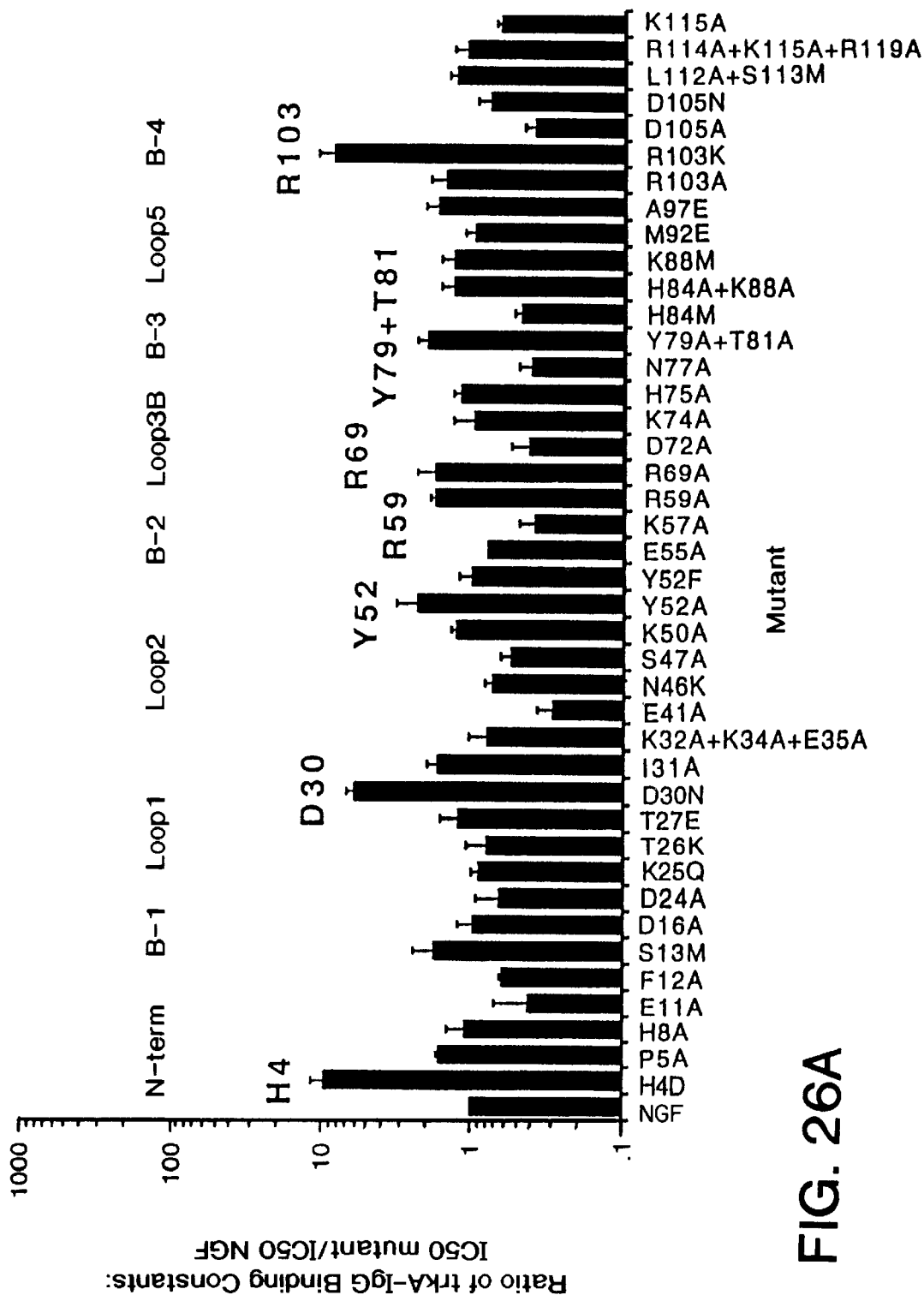

FIGS. 26A and 26B depict the binding of hNGF point mutants to trkA and gp75 receptors. The affinities of the mutants were determined by competition binding and are presented as the ratio of the mutant $IC_{50}$ to that of natural hNGF. The $IC_{50}$ was determined by competition binding curves performed at least twice from two independent transfections of each mutant hNGF. The SD of the $IC_{50}$ ratios for 4–6 independent measurements for each mutant is presented. The residues of hNGF tested for effects on binding were mostly surface-exposed, as predicted by the murine NGF crystal structure.

Figure 27:
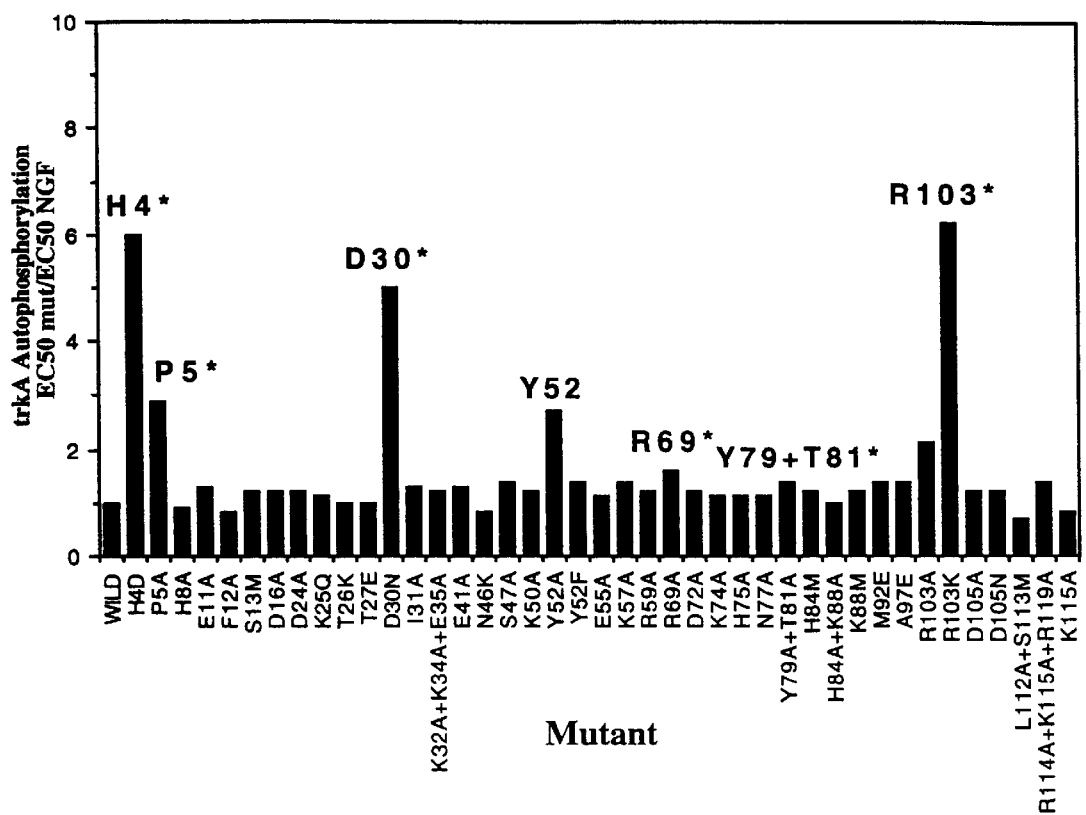

FIG. 27 depicts the biochemical activity of hNGF mutants measured by a trkA-autophosphorylation ELISA assay. The $EC_{50}$ for each mutant, relative to that of hNGF ($EC_{50}$=120 pM), is presented. Mutated residues having the greatest effects on potency are indicated by residue number. Mutated residues having additional effects on extent of autophosphorylation (efficacy) are indicated by residue number and asterisk (*).

Figure 28:
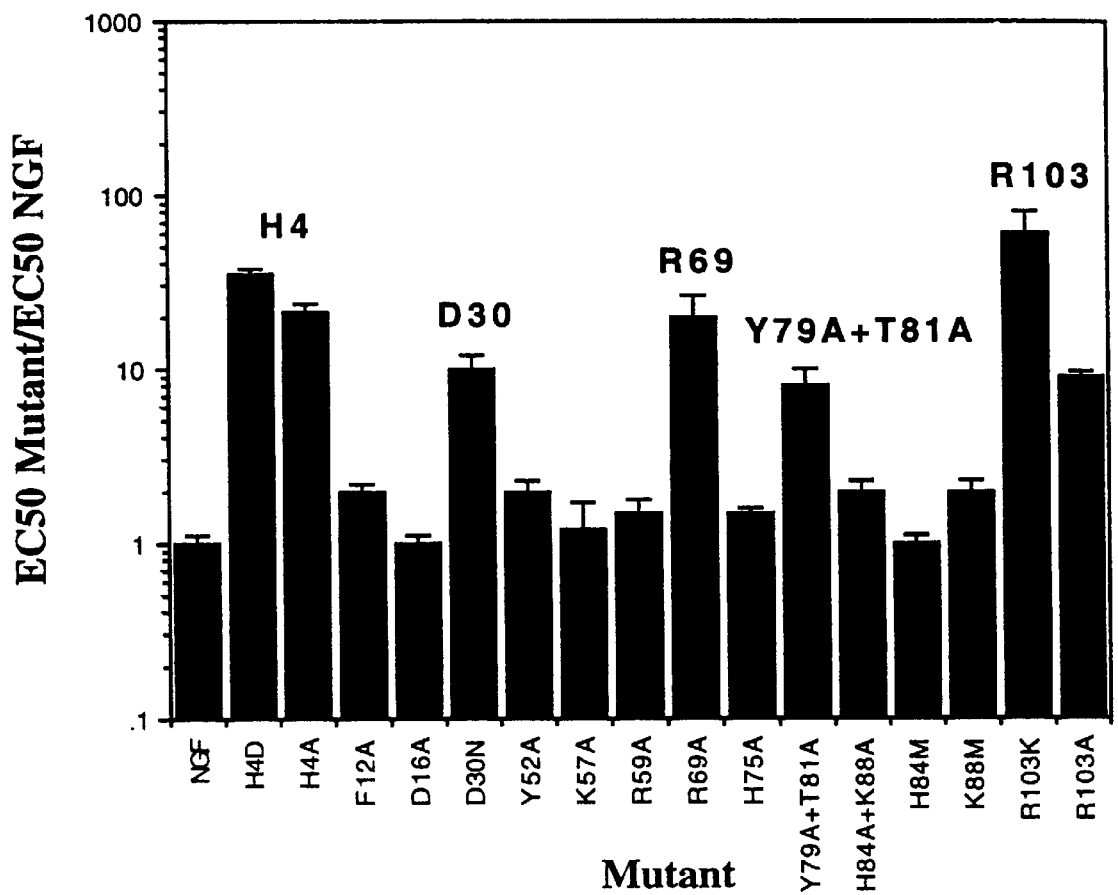

FIG. 28 depicts the bioactivity of selected hNGF mutants in the trkA-PC12 cell neurite outgrowth assay. The ratio of the $EC_{50}$ for neurite outgrowth of each mutant compared to the response of hNGF is plotted. Mutated residues with the greatest effects are indicated. All other mutants are presently being examined.

DETAILED DESCRIPTION OF THE INVENTION

Single letter codes for the amino acids are used herein, as is known in the art, according to the following table:

TABLE I

| Amino acid | three letter abbreviation | single letter abbreviation |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Serine | Ser | S |
| Threonine | Thr | T |
| Tryptophan | Trp | W |
| Tyrosine | Tyr | Y |
| Valine | Val | V |
| Proline | Pro | P |

Thus, the identification of an amino acid residue is the single letter amino acid code followed by the position number of the residue. It is to be understood that the position number corresponds to the particular neurotrophin backbone; thus, D15A NT3 means that the aspartic acid at position 15 of NT3 is changed to an alanine. This aspartic acid, found within a "constant region" as defined below, corresponds to position 16 of NGF, since NGF has an additional amino acid at its N-terminus, as shown in FIG. 8.

The present invention provides pantropic neurotrophins. Generally, a neurotrophin is a protein involved in the development, regulation and maintenance of the nervous system, and in particular of neurons. Currently, there are at least five known important neurotrophic factors: nerve growth factor(NGF), neurotrophin-3 (NT3), neurotrophin-4 (NT4, also sometimes called neurotrophin-5 (NT5) or NT4/5), brain-derived neurotrophic factor (BDNF), and ciliary neurotrophic factor (CNTF).

By the term "pantropic neurotrophins" or "pantropic neurotrophic factors", or grammatical equivalents, herein is meant a neurotrophin which, unlike naturally occurring neurotrophins, has multiple neurotrophin specificities. That is, it contains domains which confer different neurotrophin specificities. In one embodiment, this means that the pantropic neurotrophins of the present invention will bind to a variety of neurotrophic receptors. Thus, for example, naturally occurring NGF, which is the natural or native ligand for the trkA receptor, does not bind appreciably to either the trkB or trkC receptor with high affinity; for example, NGF binds to these receptors with a 500–1000 fold lower KD than BDNF or NT3, respectively. However, a pantropic NGF, i.e. a pantropic neurotrophin whose amino acid backbone is based on NGF, may bind to at least the trkA, trkB and p75 receptor. Alternatively, a pantropic NGF will bind to the trkA, trkC and p75 receptor. A preferred embodiment allows the binding of the trkA, trkB, trkC and p75 receptor. Similarly, naturally occurring BDNF and NT4/5, which are the natural ligands for the trkB receptor, do not bind appreciably to either the trkA or trkC receptor as above. Thus pantropic BDNF or NT4/S will bind to trkB and any combination of trkA, trkC and p75, as shown above for pantropic NGF.

In alternative embodiments, the naturally occurring neurotrophin will bind with poor affinity to several neurotrophin receptors. In this embodiment, the pantropic neurotrophin binds to these receptors with affinities higher than normally found, similar to the affinities seen for the natural ligand. For example, NT3 binds strongly to trkC, and weakly to trkA and trkB. Thus, a pantropic NT3 binds to trkC with its normal binding affinity, and will bind to either trkA with an affinity similar to the trkA natural ligand, NGF, or to trkB with an affinity similar to the trkB natural ligands BDNF or NT4/5, or both.

In the preferred embodiment, the binding affinity of the pantropic neurotrophin for neurotrophin receptors is at least about 50–60%, preferably about 75–80%, and most preferably about 90% of the binding affinity of the natural ligand. Thus, a pantropic NGF will bind to the trkB or trkC receptor with at least 50% of the binding of BDNF or NT4/5, or NT3, respectively. This affinity is measured by a variety of ways, as will appreciated by those skilled in the art. The preferred method is the use of competition assays, as shown in (84) and in Example 2. Generally, binding affinities are reported as $IC_{50}$, that is, the concentration of unlabeled competitor which inhibits 50% of the binding of labeled ligand to the receptor.

In alternative embodiments, the pantropicity of the neurotrophin is measured not by binding affinity to neurotrophin receptors, but rather by the neuronal survival or neurite outgrowth assays. Thus, all neurotrophins support the survival of embryonic neural crest-derived sensory neurons (77), (78), (7), (17). Survival of embryonic sympathetic neurons is only supported by NGF, while survival of placode-derived sensory neurons is supported by NT3 and BDNF (85). Survival of sensory neurons of the dorsal root ganglion is supported by both NGF and BDNF (13). NT3 elicits neurite outgrowth of sensory neurons from dorsal root ganglion, sympathetic chain ganglia, and nodose ganglion, as well as supports survival of nodose ganglia neurons and dorsal root ganglion neurons. Thus, neuronal survival assays or neurite outgrowth assays can be run to determine the pantropicity of the pantropic neurotrophins.

Thus, neurotrophin specificity is determined by the neurotrophin receptor binding, and the neuronal survival assays and/or neurite outgrowth assays. Thus, a pantropic neurotrophin with NGF specificity means a neurotrophin which exhibits at least the binding characteristics, neuronal survival assay specificity, or the neurite outgrowth assay specificity of NGF. Similarly, a pantropic neurotrophin with BDNF, NT3 or NT4/5 specificity exhibits at least the binding characteristics, neuron survival assay specificity, or neurite outgrowth assay specificity of BDNF, NT3 or NT4/5, respectively.

In an additional embodiment, pantropic neurotrophins are made by constructing covalent heterodimers. Normally, neurotrophins are homodimers, comprising two identical monomers which are noncovalently associated. In this embodiment, as outlined below, pantropicity is conferred by each monomer containing domains which confer different neurotrophic specificity. Alternatively, pantropicity may be created by covalently attaching two different neurotrophins with different specificities to create a covalent heterodimer. Thus, for example, a NGF monomer may be covalently attached to a NT3 monomer, resulting in a pantropic neurotrophin with both NGF and NT3 specificity. Similarly, covalent heterodimers may be made with any combination of NGF, NT3, NT4/5, BDNF or CNTF to create pantropic neurotrophins with at least two specificities. In addition, this procedure may be done with monomers which are themselves pantropic, resulting in covalent dimers of any combination of pantropic and single specificity monomers. Thus, a pantropic covalent dimer may be a homodimer of two pantropic monomers. However, to be included within the definition of the present invention, the pantropic covalent dimer must have at least two, and preferably three, neurotrophin specificities.

The covalent attachment is preferably done as a direct fusion of the nucleic acid, such that when the protein is expressed, the C-terminus of the first monomer is attached directly to the N-terminus of the second monomer, creating a single nucleic acid encoding the dimer. In alternative embodiments, a linker may be used, such as short repeats of clycine, or glycine and serine; for example, a linker such as gly-gly or gly-gly-ser-gly-gly (SEQ ID NO:8) may be used. This is done using techniques well known in the art. Other techniques for the covalent attachment of proteins are well known in the art.

Pantropic neurotrophins accomplish pantropic binding, or, as discussed above, pantropic neuronal survival, by containing domains which confer neurotrophin receptor specificity or binding. A domain may be defined in one of two ways. In the first embodiment, a domain is a portion of the neurotrophin which confers some neurotrophic specificity. In this embodiment, a single monomer of the pantropic neurotrophin contains one or several domains which confer different specificities. The domains can range in size from a single amino acid to about 10–15 amino acids. The domain may be comprised of a combination of amino acids from a different neurotrophin than the host neurotrophin, i.e. a domain from one neurotrophin may be substituted into a second neurotrophin, conferring pantropicity to the second neurotrophin. Alternatively, the domain may result from amino acid substitutions which are not based on homology to existing neurotrophins, as outlined below. In the preferred embodiment, the domain comprises a continuous sequence of amino acids; that is, a single stretch of amino acids is replaced. In other embodiments, the domain may be comprised of discontinuous amino acids; for example, several regions within the neurotrophin may confer specificity, and thus replacements at several positions within the neurotrophin are necessary for pantropicity.

In some embodiments, there is more than one domain within a neurotrophin which can confer neurotrophic specificity, which will depend on the particular neurotrophin. BDNF, for example, has a number of domains which appear to confer BDNF specificity. The present invention shows that a single amino acid change in NT3, from aspartic acid at position 15 to an alanine, confers BDNF specificity to NT3. This domain can also be imported into the NGF and NT4/5 sequences at the positions that correspond to position 15 in NT3; i.e. position 16 in NGF or position 18 in NT4/5. It should be understood that the corresponding amino acids are determined by an examination of the alignment of the sequences, as shown in FIG. 8. In addition to this domain, there are other domains within BDNF which confer BDNF specificity. For example, the substitution of the BDNF sequence from positions 78 to 88 (QCRTTQSYVR) (SEQ ID NO:9), S or from positions 93–99 (SKKRIG) (SEQ ID NO:10) may confer BDNF specificity (55).

Similarly, NT3 has a number of domains which may confer NT3 specificity when substituted into a different neurotrophin. A number of residues of NT3 have been shown to be important in NT3 trkC receptor binding as well as bioactivity assays. Specifically, mutations at positions R103, D105, K80, Q83, E54, R56, T22, Y51, V97, Y11, E7, R8, E10 and R68 all contribute to NT3 specificity, since mutations at these positions in NT3 cause decreases in NT3 activity. Of these, K80, Q83, T22, and V97 are within variable regions as shown in FIG. 8, and the rest are found within constant regions. In addition, residues in the vicinity of the residues may also give NT3 specificity. In some embodiments, changes in the constant regions may also give NT3 specificity. Alternatively, mutations at positions R31 and E92caused increases in NT3 binding; specifically, R31A and E92A NT3 showed increased trkC binding. These mutations can be directly imported into neurotrophins besides NT3, using the procedures described below. The amino acids at any of these positions may be changed, as outlined below.

NGF has a number of domains which may confer NGF specificity when substituted into a different neurotrophin. The N-terminal amino acids of NGF confer NGF specificity when substituted for the N-terminal residues of NT3. Specifically, the 7 N-terminal amino acids (SSSHPIF) (SEQ ID NO:11) of NGF may be substituted for the 6 N-terminal amino acids of NT3 (YAEHKS) (SEQ ID NO:12), resulting in a pantropic NT3 with NGF specificity. The exact number of NGF N-terminal residues is not crucial; as shown in the Examples, and particularly in Example 3, the histidine at amino acid position 4 appears to be quite important for NGF specificity; thus from about 4 to about 10 N-terminal residues may be exchanged although in some embodiments, a single amino acid change will be sufficient. Similarly, a number of other residues of NGF have been shown to be important in NGF trkA receptor binding as well as bioactivity assays. For example, there are a number of residues which, when mutated, lose NGF activity. This shows the importance of the residue for NGF specificity. These residues include, but are not limited to, H4, P5, V18, V20, G23, D30, Y52, R59, R69, H75, Y79, T81, and R103. Of these, D30, R59, Y79, and T81 are in "variable regions", i.e. regions which vary between the different neurotrophins, as shown in FIG. 8, with the remainder in constant regions. In some embodiments, the variable region residues are more likely to cause NGF specificity, since constant region residues may be important for general structure and characteristics, and may not confer specificity. However, as shown above for the D15A mutation, mutations in the constant regions can confer specificity as well. Furthermore, there are a number of amino acid substitutions in NGF which increase NGF binding and/or bioactivity. Accordingly, these substitutions may be imported into other neurotrophin backbones to confer NGF specificity. These residues include, but are not limited to, E11, F12, D24, E41, N46, S47, K57, D72, N77, H84, D105, and K115.

Once identified, the residues important in neurotrophin specificity can be replaced by any of the other amino acid residues using techniques described in the examples and well-known techniques for site-directed mutagenesis. Generally, the amino acids to be substituted are chosen on the basis of characteristics understood by those skilled in the art. For example, when small alterations in the characteristics are desired, substitutions are generally made in accordance with the following table:

TABLE 2

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Table 1. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., lutamyl or aspartyl; or (d) a residue having a bulky side chain, e.g., phenylalanine, is substituted for (or by) one not having a side chain, e.g., glycine. In a preferred embodiment, the residues are changed to alanine residues.

Other domains within each neurotrophin may be found using the techniques disclosed herein. Specifically, the modelling techniques of Example I allow the identification of putative specificity sites. In addition, homologue-scanning mutagenesis, random mutagenesis, cassette mutagenesis, may all be used to generate putative pantropic neurotrophins which may then be screened for receptor binding using the techniques described in the Examples and well-known in the art.

In the context of a covalent heterodimer, a domain may also refer to the entire neurotrophin monomer. Thus, a pantropic covalent heterodimer can be comprised of a domain which confers NT3 specificity, i.e. the NT3 monomer, covalently attached to a domain that confers BDNF specificity, i.e. the BDNF monomer. Similarly, an NT3 monomer may be paired with an NGF monomer, or an NGF monomer may be paired with a BDNF monomer. In addition, covalent heterodimers may be made with NT4/5 and CNTF monomers as well. In these embodiments, the domain is large, and generally comprises most or all of the wild-type neurotrophin amino acid sequence.

In the broadest embodiment, a pantropic neurotrophin binds to at least three different neurotrophin receptors. In the preferred embodiment, the pantropic neurotrophin binds to at least four different neurotrophin receptors.

By the term "neurotrophin receptor" or grammatical equivalents herein is meant a receptor which binds a neurotrophin ligand. In some embodiments, the neurotrophin receptor is a member of the tyrosine kinase family of receptors, generally referred to as the "trk" receptors, which are expressed on the surface of distinct neuronal populations. The trk family includes, but is not limited to, trkA (also known as $p140^{trk}$); trkB (also known as $p145^{trkB}$); and trkC (also known as $p_{145}^{trkC}$). In other embodiments, the neurotrophin receptor is $p75^{NGFR}$, also called p75 or low-affinity nerve growth factor receptor (LNGFR). It is to be understood that other as yet undiscovered neurotrophin receptors may also bind the pantropic neurotrophins of the present invention, as will be easily ascertainable by those skilled in the art.

In a preferred embodiment, the pantropic neurotrophin is a pantropic NT3. In this context, a pantropic NT3 is a pantropic neurotrophin which has an amino acid sequence homologous to the amino acid sequence of NT3, with domains which confer other neurotrophin specificities. In the preferred embodiment, the domains are substituted for NT3 residues; that is, some number of amino acids are deleted from the NT3 sequence, and an identical or similar number of amino acids are substituted, conferring an additional specificity. For example, the MNTS-1 (multiple neurotrophic specificities-1) pantropic NT3 comprises the first 7 amino acids of NGF replacing the 6 N-terminal residues of NT3, plus the D15A substitution. The MNTS-I pantropic NT3 has NT3, NGF, and BDNF specificities, and also binds to the p75 receptor. Other pantropic NT3s are made using minimal changes within the N-terminus. For example, since H4 and P5 are conserved among NGFs, and 2 hydrophobic residues in positions 6 and 7 are conserved, the following variants are made: 1) YASHPIF(SEQ ID NO:13)-hNT3; 2) YAHPIF(SEQ ID NO:14)-hNT3; 3) YASHPIS(SEQ ID NO:15)-hNT3; 4) YAEHPIF(SEQ ID NO:16)-hNT3; 5) YAQHPIF(SEQ ID NO:17)-hNT3. When the D15A substitution is added, the resulting neurotrophins exhibit NGF, NT3 and BDNF specificity. Alternatively, replacing the variable region 2 or 3 or 4, or combinations, of NT3 with the corresponding region from NGF gives a pantropic neurotrophin with both NT3 and NGF specificity.

In a preferred embodiment, the pantropic neurotrophin is pantropic NGF. In this context, a pantropic NGF is a pantropic neurotrophin which has an amino acid sequence homologous to the amino acid sequence of NGF, with domains which confer other neurotrophin specificities. In the preferred embodiment, the domains are substituted for NGF residues; that is, some number of amino acids are deleted from the NGF sequence, and an identical or similar number of amino acids are substituted, conferring an additional specificity. For example, a pantropic NGF is made with a D16A substitution, which confers BDNF specificity, plus substitutions in the pre-variable region 1 (V18E+V20L+G23T) and in variable region 4 (Y79Q+T8 1 K+H84Q+F86Y+K88R). Alternatively, the substitutions in the pre-variable region 1 can be made with only single amino acid substitutions in variable region 4; for example, V18E+V20L+G23T and one of Y79Q, T81K, H84Q, F86Y, or K88R may be made.

In one embodiment, the pantropic neurotrophin is a pantropic NT4/5. For example, NGF specificity may be conferred on NT4/5 by replacing the N-terminal 9 amino acids of NT4/5 with the N-terminal 7 amino acids of NGF.

In one embodiment, binding to the p75 receptor by the pantropic neurotrophin has been substantially diminished or eliminated. For example, as shown in FIG. 26, there are a variety of amino acid residues which contribute to p75 binding, in which mutations result in diminished p75 binding. In NT3, mutations at positions R68, Y11, K73. R1 14, K115, Y51, K73, R31 and H33 and in NGF, mutations at positions F12, I31, K32, K34, K50, Y52, R69, K74, K88, L112, S113, R114, and K115 all result in diminished p75 binding. Since F12, I31, K50, Y52, R69, and K74 are all within constant regions of the neurotrophins, as shown in FIG. 8, these changes are expected to alter p75 binding in the other neurotrophins as well. The other residues may be altered as well.

In addition to the amino acid changes outlined above, those skilled in the art understand that some variability of the amino acid sequence is tolerated without altering the specificity and characteristics of the neurotrophin. Thus, pantropic neurotrophins can have amino acid substitutions, insertions or deletions compared to the wild-type sequences which do not affect pantropicity but are merely variations of the sequence. In some embodiments, these mutations will be found within the same positions identified as important to specificity; i.e. in some cases, neutral mutations may be made without changing neurotrophin specificity.

The pantropic neurotrophins of the present invention can be made in a variety of ways, using recombinant technology. By the term "recombinant nucleic acid" herein is meant nucleic acid in a form not normally found in nature. That is, a recombinant nucleic acid is flanked by a nucleotide sequence not naturally flanking the nucleic acid or has a sequence not normally found in nature. Recombinant nucleic acids can be originally formed in vitro by the manipulation of nucleic acid by restriction endonucleases, or alternatively using such techniques as polymerase chain reaction. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e., through the expression of a recombinant nucleic acid as depicted above. A recombinant protein is distinguished from naturally occurring protein by at least one or more characteristics. For example, the protein may be isolated away from some or all of the proteins and compounds with which it is normally associated in its wild type host. The definition includes the production pantropic neurotrophins from one organism in the same or different organism or host cell. For example, the protein may be made in the same organism from which it is derived but at a significantly higher concentration than is normally seen, e.g., through the use of a inducible or high expression promoter, such that increased levels of the protein is made. Alternatively, the protein may be in a form not normally found in nature, as in the addition of an epitope tag or amino acid substitutions, insertions and deletions.

Using the nucleic acids of the invention which encode pantropic neurotrophins, a variety of expression vectors are made. The expression vectors may be either self-replicating extrachromosomal vectors or vectors which integrate into a host genome. Generally, expression vectors include transcriptional and translational regulatory nucleic acid operably linked to the nucleic acid encoding the pantropic neurotrophin. "Operably linked" in this context means that the transcriptional and translational regulatory DNA is positioned relative to the coding sequence of the pantropic neurotrophin in such a manner that transcription is initiated. Generally, this will mean that the promoter and transcriptional initiation or start sequences are positioned 5' to the pantropic neurotrophin coding region. The transcriptional and translational regulatory nucleic acid will generally be appropriate to the host cell used to express the pantropic neurotrophin; for example, transcriptional and translational regulatory nucleic acid sequences from mammalian cells will be used to express the pantropic neurotrophin in mammalian cells. Numerous types of appropriate expression vectors, and suitable regulatory sequences are known in the art for a variety of host cells.

In general, the transcriptional and translational regulatory sequences may include, but are not limited to, promoter sequences, signal sequences, ribosomal binding sites, transcriptional start and stop sequences, translational start and stop sequences, termination and poly A signal sequences, and enhancer or activator sequences. In a preferred embodiment, the regulatory sequences include a promoter and transcriptional start and stop sequences.

Promoter sequences encode either constitutive or inducible promoters. Hybrid promoters, which combine elements of more than one promoter, are also known in the art, and are useful in the invention.

In addition, the expression vector may comprise additional elements. For example, the expression vector may have two replication systems, thus allowing it to be maintained in two organisms, for example in mammalian cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

The pantropic neurotrophins of the invention are produced by culturing a host cell transformed with an expression vector containing nucleic acid encoding a pantropic neurotrophin, under the appropriate conditions to induce or cause expression of the pantropic neurotrophin. The conditions appropriate for pantropic neurotrophin expression will vary with the choice of the expression vector and the host cell, and will be easily ascertained by one skilled in the art. For example, the use of constitutive promoters in the expression vector will require optimizing the growth and proliferation of the host cell, while the use of an inducible or repressible promoter requires the appropriate growth conditions for induction or derepression.

In a preferred embodiment, the pantropic neurotrophin is purified or isolated after expression. The pantropic neurotrophins may be isolated or purified in a variety of ways known to those skilled in the art depending on what other components are in the sample. Standard purification methods include electrophoretic, molecular, immunological and chromatographic techniques, including ion exchange, hydrophobic, affinity, and reverse-phase HPLC chromatography, and chromatofocusing. Ultrafiltration and diafiltration techniques, in conjunction with protein concentration, are also useful. For general guidance in suitable purification techniques, see (57). The degree of purification necessary will vary depending on the use of the pantropic neurotrophin. In some instances no purification will be necessary.

Appropriate host cells include yeast, bacteria, archebacteria, fungi such as filamentous fungi, and plant and animal cells, including mammalian cells. Of particular interest are *Saccharomyces cerevisiae* and other yeasts, *E. coli, Bacillus subtilis, Pichia pastoris,* SF9 cells, C129 cells, 293 cells, Neurospora, and CHO, COS, HeLa cells, immortalized mammalian myeloid and lymphoid cell lines. A preferred host cell is a mammalian cell, and the most preferred host cells include CHO cells, COS-7 cells, and human fetal kidney cell line 293.

In a preferred embodiment, the pantropic neurotrophins of the invention are expressed in mammalian cells. Mammalian expression systems are also known in the art.

Some genes may be expressed more efficiently when introns are present. Several cDNAs, however, have been efficiently expressed from vectors that lack splicing signals. Thus, in some embodiments, the nucleic acid encoding the pantropic neurotrophin includes introns.

The methods of introducing exogenous nucleic acid into mammalian hosts, as well as other hosts, is well known in the art, and will vary with the host cell used, and include dextran-mediated transfection, calcium phosphate precipitation, polybrene mediated transfection, protoplast fusion, electroporation, encapsulation of the polynucleotide (s) in liposomes, and direct microinjection of the DNA into nuclei.

In one embodiment, pantropic neurotrophins are produced in yeast cells. Yeast expression systems are well known in the art and include expression vectors for *Saccharoniyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe,* and *Yarrowia lipolytica*. The methods of introducing exogenous nucleic acid into yeast hosts, as well as other hosts, is well known in the art, and will vary with the host cell used.

In a preferred embodiment, pantropic neurotrophins are expressed in bacterial systems. Expression vectors for bacteria are well known in the art, and include vectors for *Bacillus subtilis, E. coli, Streptococcus cremoris,* and *Streptococcus lividans,* among others. The bacterial expression vectors are transformed into bacterial host cells using techniques well known in the art, such as calcium chloride treatment, electroporation, and others.

In one embodiment, pantropic neurotrophins are produced in insect cells. Expression vectors for the transformation of insect cells, and in particular, baculovirus-based expression vectors, are well known in the art. Materials and methods for baculovirus/insect cell expression systems are commercially available in kit form; for example the "MaxBac" kit from Invitrogen in San Diego.

Recombinant baculovirus expression vectors have been developed for infection into several insect cells. For example, recombinant baculoviruses have been developed for *Aedes aegypti, Autographo californica, Bombyx mori, Drosophila melangaster, Spodoptera frugiperda,* and *Trichoplusia ni.*

Once expressed, pantropic neurotrophins are used as neurotrophic factors. These pantropic neurotrophins may be utilized in various diagnostic and therapeutic applications.

The pantropic neurotrophins of the present invention are useful in diagnostic methods of detecting neurotrophin receptors. For example, the pantropic neurotrophins of the present invention may be labelled. By a "labelled pantropic neurotrophin" herein is meant a pantropic neurotrophin that has at least one element, isotope or chemical compound attached to enable the detection of the pantropic neurotrophin or the pantropic neurotrophin bound to a neurotrophin receptor. In general, labels fall into three classes: a) isotopic labels, which may be radioactive or heavy isotopes; b) immune labels, which may be antibodies or antigens; and c) colored or fluorescent dyes. The labels may be incorporated into the pantropic neurotrophin at any position. Once labelled, the pantropic neurotrophins are used to detect neurotrophin receptors, either in vitro or in vivo. For example, the presence of neurotrophin receptors can be an indication of the presence of certain cell types, useful in diagnosis. That is, a subpopulation of certain cell types may be shown by the binding of the labelled pantropic neurotrophin to the cells via the receptors.

Additionally, the pantropic neurotrophins of the present invention are useful as standards in neurotrophin assays. For example, the activity of a pantropic neurotrophin in any particular assay may be determined using known neurotrophin standards, and then the pantropic neurotrophin may be used in the diagnosis and quantification of neurotrophins.

Furthermore, the pantropic neurotrophins of the present invention are useful as components of culture media for use in culturing nerve cells in vivo, since many nerve cell cultures require growth factors. As will be understood by those skilled in the art, the pantropic neurotrophins of the present invention can replace other neurotrophic factors which are frequently used as media components. The amount of the pantropic neurotrophins to be added can be easily determined using standard assays.

The pantropic neurotrophins of the present invention are also useful to generate antibodies, which can be used in the diagnosis, identification, and localization of neurotrophins or neurotrophin antibodies within an organism or patient. For example, the pantropic neurotrophins can be used to make polyclonal or monoclonal antibodies as is well known by those skilled in the art. The antibodies can then be labelled and used to detect the presence, or absence, of the neurotrophins. Thus, diagnosis of neural disorders associated with neurotrophins may be detected. Alternatively, the antibodies are detected indirectly, by using a second antibody. For example, primary antibodies may be made in mice or rabbits, and then labelled anti-mouse or anti-rabbit antibodies are used to detect the primary antibodies. Either of these methods, as well as similar methods well known in the art, allow the detection of neurotrophins in a variety of tissues.

In addition, the antibodies Generated to the pantropic neurotrophins of the present invention are also useful for the purification of neurotrophins and pantropic neurotrophins. Since generally the amino acid substitutions of the pantropic neurotrophins are small, many immune epitopes are shared by the neurotrophins and pantropic neurotrophins. Thus, antibodies generated to the pantropic neurotrophins will bind naturally occurring neurotrophins, and thus are useful in purification. For example, purification schemes based on affinity chromatography techniques can be used, as are well known in the art.

In the preferred embodiment, the pantropic neurotrophins of the present invention are administered to a patient to treat neural disorders. By "neural disorders" herein is meant disorders of the central and/or peripheral nervous system that are associated with neuron degeneration or damage. Specific examples of neural disorders include, but are not limited to, Alzheimer's disease, Parkinson's disease, Huntington's chorea, stroke, ALS, peripheral neuropathies, and other conditions characterized by necrosis or loss of neurons, whether central, peripheral, or motomeurons, in addition to treating damaged nerves due to trauma, burns, kidney disfunction or injury. For example, peripheral neuropathies associated with certain conditions, such as neuropathies associated with diabetes, AIDS, or chemotherapy may be treated using the pantropic neurotrophins of the present invention. Additionally, the administration of NT3 prevents the in vivo degeneration of adult central noradrenergic neurons of the locus coerulus in a model that resembles the pattern of cell loss found in Alzheimer's disease (86) In addition, the addition of NT3 has been shown to enhance sprouting of corticospinal tract during development, as well as after adult spinal cord lesions (58). In fact, when NT3 was administered with antibodies which inhibit myelin-associated growth inhibitory proteins, long-distance regeneration was seen. Thus, the pantropic neurotrophins of the present invention can be used in place of NT3 in this application.

In this embodiment, a therapeutically effective dose of a pantropic neurotrophin is administered to a patient. By "therapeutically effective dose" herein is meant a dose that produces the effects for which it is administered. The exact dose will depend on the disorder to be treated, and will be ascertainable by one skilled in the art using known techniques. In general, the pantropic neurotrophins of the present invention are administered at about 1 $\mu$g/kg to about 100 mg/kg per day. In addition, as is known in the art, adjustments for age as well as the body weight, general health, sex, diet, time of administration, drug, interaction and the severity of the disease may be necessary, and will be ascertainable with routine experimentation by those skilled in the art.

A "patient" for the purposes of the present invention includes both humans and other animals and organisms. Thus the methods are applicable to both human therapy and veterinary applications.

The administration of the pantropic neurotrophins of the present invention can be done in a variety of ways, including, but not limited to, orally, subcutaneously, intravenously, intracerebrally, intranasally, transdermally, intraperitoneally, intramuscularly, intrapulmonary, vaginally, rectally, or intraocularly. The pantropic neurotrophins may be administered continuously by infusion into the fluid reservoirs of the CNS, although bolus injection is acceptable, using techniques well known in the art, such as pumps or implantation. In some instances, for example, in the treatment of wounds, the pantropic neurotrophins may be directly applied as a solution or spray.

The pharmaceutical compositions of the present invention comprise a pantropic neurotrophin in a form suitable for administration to a patient. In the preferred embodiment, the pharmaceutical compositions are in a water soluble form, and may include such things as carriers, excipients, stabilizers, buffers, salts, antioxidants, hydrophilic polymers, amino acids, carbohydrates, ionic or nonionic surfactants, and polyethylene or propylene glycol. The pantropic neurotrophins may be in a time-release form for implantation, or may be entrapped in microcapsules using techniques well known in the art.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes.

EXAMPLES

Example 1

Molecular modeling of NT-3 and identification of targets for mutational analysis The coordinates for the three-dimensional structure of mouse NGF were obtained from N. Q. McDonald and T. L. Blundell. The molecular modeling for human NT-3 was performed on a Silicon Graphics Iris Workstation using the interactive program InsightII. The representations of NT-3 structures were produced using the program MidasPlus. (University of California at San Francisco).

When the three-dimensional structure of mouse NGF (mNGF) became available (59) a rational approach to the structural basis of neurotrophic function using protein engineering techniques became possible. The structure of mNGF consists of a tightly associated dimer of two identical amino acid polypeptide chains. The fold of each monomer is formed by extended segments of twisted anti-parallel β-sheets linked by turns. The molecule has an elongated shape and provides a flat hydrophobic surface that forms the interface of the associated monomers (59). A striking feature of the structure is the arrangement of the disulfide bonds, now known as the cysteine-knot motif (60). This motif is also found in the otherwise unrelated TGF-β (61); (6()) and PDGF-BB (87). Several regions of the mNGF structure, including the amino and carboxy termini and the loop between residues 43 and 48 were not well defined, indicating highly flexible structural elements.

Figure 1:
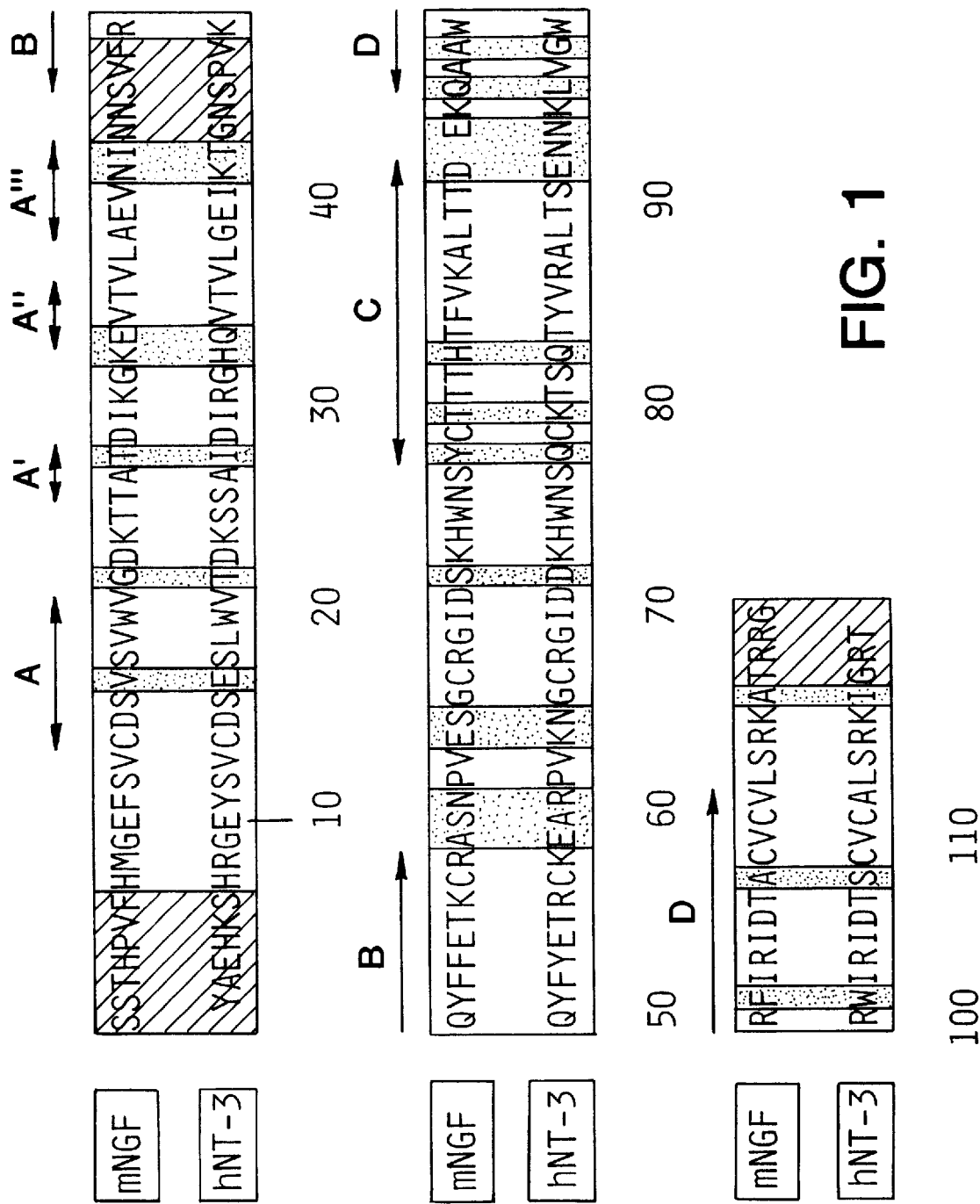
FIG. 1 depicts the high homology between mouse NGF (SEQ ID NO:1) and human NT-3 (SEQ ID NO:2) allows modeling of NT-3 on 3D-structure of NGF. Arrows indicate β-strands. Designations of β-strands as in McDonald et al. (1991) (59). Amino acids which differ between NGF and NT-3 are in gray boxes. Sections with disordered structure are hatched.
Figure 2A:
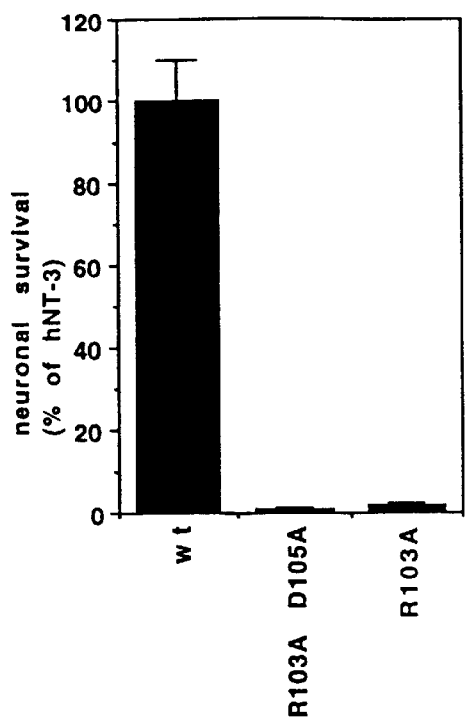
FIGS. 2A, 2B, 2C, 2D and 2E depicts the biological effects of selected mutants on survival of dorsal root ganglion neurons and neurite extension on PC12/trkC cells. E9 chick DRG neurons cultured for 72 hours in the presence of conditioned media of 293 cells containing NT-3 or mutant proteins. Response induced by mutants expressed as % of NT-3 response. A) 5 ng/ml of NT-3, R103A/D105A and R103A. B) 1 ng/ml NT-3, R103M, R103K, N1, Y51A. C) 0.2 ng/ml NT-3, Y11A, T22Q and K80A Q83A. The error is the SD of triplicate determinations.
Figure 2B:
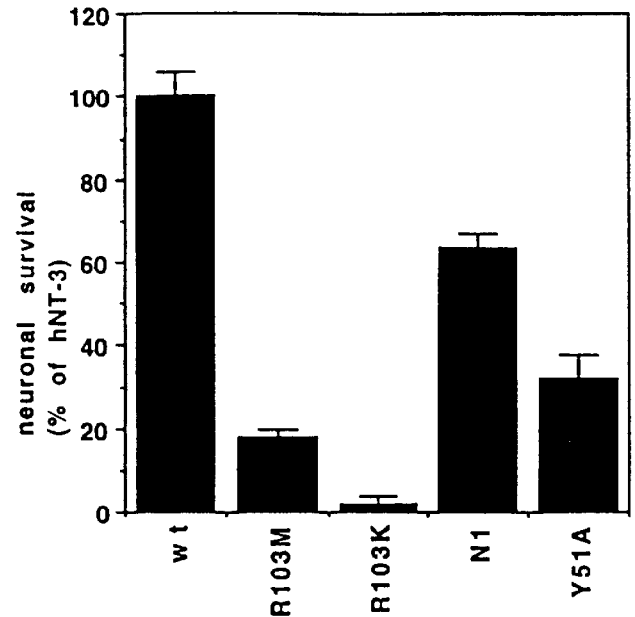
Figure 2C:
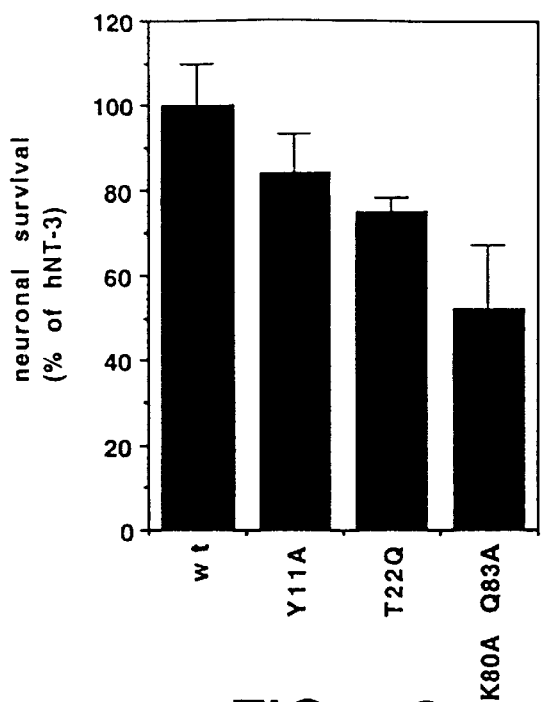
Figure 2D:
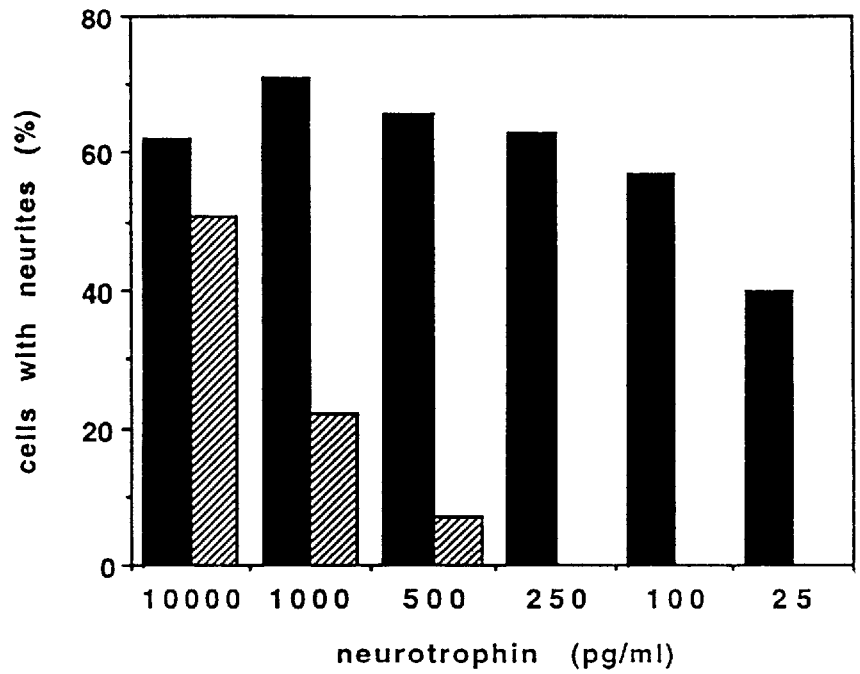
Figure 2E:
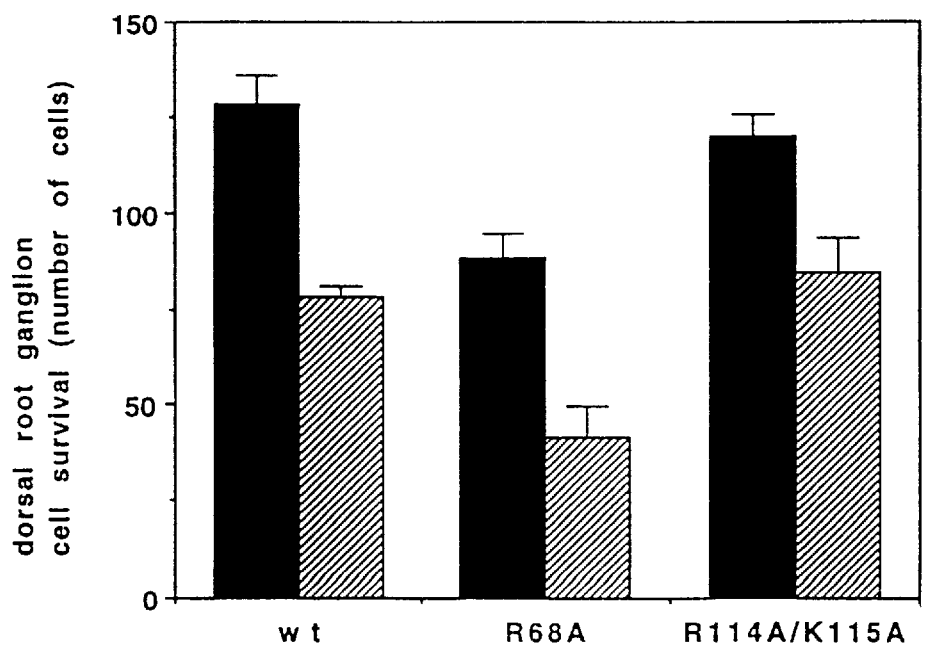

The sequence of human NT-3 (hNT-3) is 56% identical and 70% similar to mNGF (FIG. 1). Sequence differences are clustered in the structurally undefined N-terminus and in the loop region between residues 43 and 48. The relative position of the cysteine residues is conserved, as in all members of the neurotrophin family, suggesting the existence of a similar cysteine-knot motif in hNT-3. The sequence similarity of hNT-3 and mouse NGF suggests that both share the same basic three-dimensional fold and therefore, mNGF was used as scaffold for the hNT-3 model. In the second step of model building, side-chains which differed between mNGF and hNT-3 were replaced with the hNT-3 amino acids using the InsightII program (Biosym Technology, San Diego, Calif.). If possible, conformations of hNT-3 side-chains were kept similar to those of MNGF, otherwise they were based on rotamer libraries (62), packing and hydrogen bonding considerations. Finally, the insertion of Asn93 and the subsequent adjustment of the loop 93–95 were cleaned from a search of crystal structures in the Protein Data Bank (63). The final model consists of 104 amino acids and does not include the six N-terminal (Tyr1-Ser6), the four C-terminal (Ile116-Thr119) and five loop residues (G44-V48). This model allowed the identification of residues that are likely to be involved in important structural contexts, which led to their exclusion from mutational analysis. These residues were either involved in the interface (W20, F52, Y53, W99, W101), in structurally important hydrogen bonds or hydrophobic contacts (S12, I30, Q50, P62, S83, R100, T106, S107), in disulfide bonds (C15, C57, C67, C79, C108, C110) or were buried in the protein interior (V13, S16, S18, V21, D29, I30, V35, V37, I102, I104). However, in some cases, it will be desirable to alter these residues. In addition Glycine and Alanine residues were not altered except for Gly 44. In contrast to related studies on the mNGF/trkA interaction mainly single residues or pairs of amino acids were substituted rather than exchanging multiple residues (53) (56) (55) or deleting residues (49). Residues were mostly changed to Alanine (64). In some cases it was possible to model larger amino acids as replacements into the structure in order to potentially create steric hindrance for the receptor ligand interaction.

The first set of mutations probed both conserved and non-conserved residues, located mainly in β-strands, that are surface exposed and therefore potentially involved in binding to the trkC and gp75 receptors. The current hypothesis proposed for NGF function (55) is that divergent residues located in loops connecting β-strands and the termini are major determinants for receptor binding and specificity. A second set of hNT-3 mutants evaluated the importance of these residues to interaction of hNT-3 and its receptors. The total set of mutants covered essentially the entire surface of the NT-3 molecule.

Example 2

Generation of specific amino acid substitutions of NT3 and pantropic NT3s

Human NT-3 was previously cloned, sequenced and subcloned into a pRK-type vector which allows for production of double and single stranded DNA in *E. coli,* as well as expression of mature NT-3 in a mammalian system under control of the cytomegalo virus promoter (65). Mutagenesis on this vector was performed according to the method of Kunkel (66) (67). After transformation into the *E. coli* strain XL1-Blue, colonies were screened for the presence of the desired mutation by sequencing single-stranded DNA using the Sequenase version 2.0 kit (U. S. Biochemical Corp.). The entire sequence coding for the mature NT-3 was verified for all positive clones. Double-stranded DNA was isolated from XL-I Blue with the QIAGEN DNA purification kit (Qiagen Inc., Chatsworth, Calif.). This DNA was subsequently used for transfection of the fetal human kidney cell line 293 (68). All other recombinant DNA manipulations were performed as described (69). Well known techniques are used to generate the primers for all the mutations. The primer for the D15A mutation was 5'-GGTCACCCACAAGCTTTCACTGGCACATACCGAG-3'(SEQ ID NO:6), and the primer for the S1 mutant (the N-terminal swap of the 6 N-terminal amino acids of NT3 for the 7 N-terminal amino acids of NGF) was 5'-GTACTCCCCTCGGTGGAAGATGGGATGGCTCGAGGACCGTTTCGTG-3'(SEQ ID NO:7).

Expression of wild-type and mutant neurotrophins

Plasmid DNA containing either the hNT-3 or mutant hNT-3 coding sequences was introduced into the human fetal kidney cell line 293 by calcium phosphate precipitation (70). The 75% confluent cells were transfected with 10 μg of plasmid DNA per 15 mm cell culture dish and incubated for 15 h. in serum containing medium. Then the medium was removed and exchanged by serum-free medium (PSO4) supplemented with 10 mg/l recombinant bovine insulin, 1 mg/l transferrin and trace elements. The supernatant was collected after 48 and 96 hours concentrated approximately 20-fold with centriprep-10 filtration units (Amicon, Beverly, Mass.) and sterile filtered.

Quantification of neurotrophin mutants

The specific hNT-3 ELISA was based on a Protein A purified polyclonal antiserum from guinea pig (Genentech). Each well of a 96-well plate (MaxiSorp; Nunc, Kamstrup, Denmark) was coated overnight at 4° C. with 100 μl of 4 μg/ml antiserum in 0.05M sodium carbonate buffer (pH 9.6). After a 1 h blocking step with blocking buffer (PBS+0.5% BSA+0.01% Thimerosal, pH 7.4), the wells were washed six times with ELISA buffer (PBS+0.5% BSA+0.05% Tween-20+0.01 % Thimerosal, pH 7.4). Purified recombinant hNT-3 or samples of hNT-3 mutants of unknown concentrations were diluted in ELISA buffer to a volume of 100 μl and added to the wells. The plates were incubated for 2h at room temperature with continous shaking. After a wash with ELISA buffer, the wells were incubated with 100 μl biotinylated anti-hNT-3 antibody (Genentech) for 2h and again washed with ELISA buffer. 100 μl of a 1:50000 dilution of streptavidin/horse radish peroxidase (Zymed, 43-4323) was added to the wells and incubated for 30 min., followed by a wash step with ELISA buffer. Finally, the color was developed for 15–20 min. using 100 μl of a PBS solution containing 0.012% $H_2O_2$ and 0.04% o-phenylenediamine. The reaction was stopped by addition of 50 μl of 4.5 N $H_2SO_4$. The absorption was read at 490 nm and at 405 nm on a Vmax kinetic microplate reader (Molecular Devices, Palo Alto, Calif.). The standard curve was determined using purified recombinant hNT-3 (Genentech) at concentrations of 50, 25, 12.5, 6.25, 3.13, 1.56 and 0.78 ng/ml. The samples with unknown NT-3 concentration were serially diluted 1:10, 1:30, 1:90, 1:270, 1:810, 1:2430, 1:7290 and 1:21870 in order to obtain multiple data-points per sample. The standard curve was determined using a four-parameter fit of the data points obtained from the assay of the standard protein.

The amounts of NT-3 mutants after concentration varied between 120 ng/ml and 36 μg/ml. The ELISA assay did not detect any NT-3 in supernatants from mock transfected cells nor did it crossreact with recombinant human NGF from supernatants of NGF transfected cells (data not shown). For each set of expressions of NT-3 mutants a native hNT-3 expression was performed and quantified by ELISA in parallel in order to obtain a comparative wt concentration for receptor binding studies. All mutants were expressed, quantified and assayed at least twice.

Iodination

Purified recombinant hNT-3, hBDNF and hNGF (Genentech) were labeled by lactoperoxidase treatment using a modification of the Enzymobead radioiodination reagent (Bio-Rad) procedure (71). Usually, 2 μg of the neurotrophins were iodinated to specific activities ranging from 3000–3500 cpm/fmol. The labeled material was stored at 4° C. and used within 2 weeks of preparation.

Binding assays

Cell based binding assays made use of preparations of membranes from stable cell lines expressing rat trkC (NIH3T3/trkC, (26)). Competitive displacement assays were performed as described previously (26). Mutants were assayed for binding affinity to the trkC receptor twice for each of the multiple expressions with a duplicate set of data points. This procedure allowed estimation of the error of affinity determination for each of the mutants. Unpurified recombinant NT-3 from transiently expressing cells was compared with purified NT-3 for its ability to displace 125-I labeled NT-3 from trkC receptors expressed on NIH/3T3 cells. Both displaced labeled NT-3 with similar IC-50: 7 pM and 9 pM for unpurified NT-3 and pure NT-3. This indicated that unpurified NT-3 from supernatants of expressing 293 cells could be quantified precisely and subsequently used for receptor binding studies. The specificity of the binding assays was demonstrated by the inability of NGF, BDNF and supernatant of mock transfected cells to displace bound labeled NT-3 from trkC (data not shown).

Receptor immunoadhesin proteins were constructed using human trkA, trkB, trkC and gp75 extracellular domains fused to immunoglobulin constant domains (Genentech, unpublished results). A 96-well plate (Coming, ELISA wells strips) was coated with 100 pi of 5 μg/ml goat F(ab')$_2$ anti-human Fc IgG (Organon Technika, West Chester, Pa.) in coating buffer for 15h at 4–8° C. The wells were aspirated, washed 3 times with PBS and incubated for 2 h with 100 μl of a 40 ng/ml solution of the receptor immunoadhesin protein in binding buffer (Leibovitz's L- 15 medium supplemented with 5 mg/ml BSA (Intergen, Purchase, Pa.), 0.1 mg/ml horse heart cylochrome C (Sigma) and 20 mM HEPES, pH7.2). After a wash step with PBS, 50 μl of binding buffer was immediately added to the wells in order to prevent drying. Each of the native and mutant protein stock solutions was serially diluted, using binding buffer, to give a concentration range of 4096–2 pM. 25 μl of serial dilution was added per well, followed by 25 μl of labeled neurotrophins. The final concentration of labeled neurotrophins in each well was approximately 50 pM for trkA, trkB and trkC assays and 100 pM for gp75 binding assays. After 3 h of incubation at room temperature, the wells were washed with PBS+0.5% Tween-20 and the bound radioactivity was counted. All displacement experiments were analyzed by applying a four-parameter fit procedure on the data set with the Kaleidagraph software package. All binding results in bar graphs are expressed as IC-50 mut/IC-50 wt.

Stimulation of autophosphorylation of trk receptors on PC12 cell lines by neurotrophic factors Approximately $1 \times 10^7$ cells were treated at 37° C. for 5 min with 25 ng/ml neurotrophin. NP-40 plate lysis and immunoprecipitation with antiserum 443 (pan-trk) or 656 (trkC specific) was done as previously described (26). The phosphotyrosine content was analyzed by Western transfer using monoclonal antibody 4G10 as previously described (23). 4G10 was detected as previously described (26).

Differentiation assays on PC12 and PC12 cells expressing trkB and trkC.

Approximately $10^3$ PC12 cells expressing the different trk family members (trkC; (26) trkB; Soppet, unpublished observations), were plated into 35 mm collagen-coated tissue culture dishes containing a total of 2 ml of medium. PC12 cells expressing trkC were assayed at three different concentrations (10 ng/ml, 1 ng/ml, 100 pg/ml) and the parental PC12 cells expressing only trkA or PC12 cells expressing trkB were treated with 10 ng/ml of NT-3 mutant supernatants. For each treatment, at least 200 cells were counted. The proportion of neurite-bearing cells was determined by counting the number of cells containing processes at least twice the length of the cell body after 3–4 days.

Dissection of embryonic tissues and neuronal cultures.

Chick embryos at different stages of development were obtained by incubating white Leghorn chick egos (SPAFAS, Reinholds, Pa.) at 38° C. in an egg incubator for the required time. Dorsal root ganglia, nodose ganglia from embryonic day 8 (E8), and sympathetic ganglia from embryonic day 11 (E11), were dissected in Leibowitz-15 (L-15) media containing 1× penicillin/streptomycin using watch-maker's forceps and electrolytically sharpened tungsten needles. Embryonic chicken ganglia were trypsinized at 37° C. for 20 min and then washed in culture medium (F14 with 10% heat-inactivated horse serum and 5% heat-inactivated fetal calf serum) and were gently triturated with a fire-polished pipette to give a single-cell suspension. Chick embryo cells were plated onto 35-mm dishes that had been coated with polyornithine (0.5 mg/ml in 0.15 M borate buffer at pH 8.6, overnight) and laminin (20 ml/ml for 4–6 hr at 37° C.) in 2 ml of culture medium in presence of 2 ng/ml of neurotrophin, or at the concentrations noted in the text. All cells with a neuronal morphology within a 5×5-mm grid in the center of each dish were counted 72 hr later.

The results are shown in Tables 3 and 4.

TABLE 3

| Mutation | Expression (% of wt) | trkC-binding (IC50 mut/IC50 wt) NIH3T3 | trkC-binding (IC50 mut/IC50 wt) IA | gp75-binding (IC50 mut/IC50 wt) IA | Neurite extension PC12 trkC | Neurite extension PC12 trkB | Neurite extension PC12 trkA | Phosphorylation PC12 trkC |
|---|---|---|---|---|---|---|---|---|
| human NT-3 | 100 | 1.00 ± 0.06 | 1.00 ± 0.09 | 1.00 ± 0.1 | + | – | – | ++ |
| b-strands | | | | | | | | |
| D15A | 26 | 0.63 ± 0.20 | 0.69 ± 0.07 | 1.00 ± 0.02 | + | + | – | ++ |
| E17A/L19A | 5 | 0.95 ± 0.10 | | | + | – | – | ++ |
| T22Q | 42 | 3.28 ± 0.73 | 3.55 ± 0.45 | 0.87 ± 0.04 | + | – | – | + |
| D23A | 66 | 0.66 ± 0.21 | | | + | – | – | ++ |
| K24A | 3 | 1.44 ± 0.14 | 1.23 ± 0.15 | | + | – | – | + |
| S25Q | 114 | 0.86 ± 0.13 | | | + | – | – | ++ |
| S26K | 116 | 0.77 ± 0.27 | | | + | – | – | ++ |
| S25K/S26Y | 97 | 0.63 ± 0.06 | | | + | – | – | ++ |
| I28Q | 36 | 1.17 ± 0.13 | | | + | – | – | N.D. |
| T36E | 269 | 0.97 ± 0.26 | | | + | – | – | ++ |
| L38E | 41 | N.D. | 1.25 ± 0.23 | | N.D | N.D | N.D | N.D. |
| E40A | 251 | 0.44 ± 0.08 | | | + | – | – | ++ |
| Y51A | 4 | >15.00 | 21.52 ± 2.32 | 18.00 ± 1.10 | – | – | – | + |
| Y51F | 59 | 1.25 ± 0.22 | | | + | – | – | ++ |
| E54A | 3 | 2.99 ± 1.62 | | 1.40 ± 0.05 | + | – | – | N.D. |
| R56A | 11 | 2.32 ± 0.89 | | 1.80 ± 0.29 | + | – | – | ++ |
| V63A | 380 | 1.12 ± 0.13 | | 0.72 ± 0.01 | + | – | – | ++ |
| R68A | 67 | 1.46 ± 0.28 | 1.55 ± 0.56 | 118.20 ± ± 46.40 | +/– | – | – | ++ |
| K80A/Q883A | 12 | 2.32 ± 0.51 | 2.72 ± 0.17 | 1.81 ± 0.06 | + | – | – | + |
| R87M | 27 | 0.93 ± 0.20 | | | + | – | – | ++ |
| L89E | 1 | N.D. | 1.18 ± 0.40 | N.D. | N.D. | N.D. | N.D. | |
| S91M | 49 | 1.15 ± 0.25 | | | + | – | – | ++ |
| S91E | 85 | 1.54 ± 0.12 | | | + | – | – | ++ |
| S91A/E92A | 35 | 0.55 ± 0.17 | | | + | – | – | N.D. |
| V97E | 39 | 1.82 ± 0.35 | 1.53 ± 0.13 | 1.34 ± 0.17 | + | – | – | ++ |
| R103A/D105A | 74 | >100.00 | 130.00 ± 37.0 | 1.22 ± 0.12 | – | – | – | – |
| R103A | 426 | >100.00 | 82.00 ± 36.00 | 2.19 ± 0.35 | – | – | – | – |
| R103M | 100 | 1.95 ± 0.23 | 1.89 ± 0.33 | 1.60 ± 0.10 | + | – | – | + |
| R103K | 102 | >100.00 | 117.00 ± 19.00 | 0.90 ± ± 0.12 | – | – | – | – |
| D105A | 75 | 0.67 ± 21 | | | + | – | – | ++ |
| Amino and carboxyl termini | | | | | | | | |
| H4A/H7A/R8A/E10A (N1) | 461 | 4.15 ± 0.61 | 3.70 ± 0.07 | 1.80 ± 0.30 | + | – | – | ++ |
| NGF-swap (S1)(SEQ I.D. NO:12) (YAEHKS > SSSHPIF) | 18 | N.D. | 1.00 ± 0.33 | 0.82 ± 0.15 | + | N.D. | + | ++ |
| E3A | 251 | 0.68 ± 0.18 | | | + | – | – | ++ |
| H4D | 348 | N.D. | 1.35 ± 0.13 | N.D | N.D | N.D | N.D. | |
| E3A/K5A/S6A (N2) | 200 | 1.65 ± 0.68 | | | + | – | – | ++ |
| Y11A | 101 | 3.34 ± 0.23 | 4.17 ± 1.27 | 57.94 ± 23.91 | + | – | – | ++ |
| R114A/K115A | 146 | 1.05 ± 0.12 | 1.38 ± 0.16 | 182.66 ± ± 37.37 | + | – | – | ++ |
| loops and turns | | | | | | | | |
| R31A/H33A/Q34A | 0 | N.D. | | | N.D. | N.D. | N.D. | N.D. |
| R31A | 74 | 0.38 ± 0.12 | | 8.45 ± 2.18 | + | – | – | N.D. |
| H33A | 81 | N.D. | 1.17 ± 0.02 | 2.01 ± 0.73 | N.D | N.D | N.D. | N.D. |
| Q34A | 176 | 1.05 ± 0.05 | | | + | – | – | N.D. |
| Q34E | 166 | 1.04 ± 0.34 | | | + | – | – | N.D. |
| R42A/T43A | 86 | 1.28 ± 0.26 | | | + | – | – | ++ |
| N45A/S46A/K49A/Y51A | 0 | N.D. | | | N.D. | N.D. | N.D. | N.D. |
| G44A | 88 | 1.17 ± 0.13 | | | + | – | – | ++ |
| N45A | 240 | 0.88 ± 0.12 | | | + | – | – | ++ |
| S46A | 265 | 0.95 ± 0.22 | | | + | – | – | ++ |
| P47A | 109 | 0.64 ± 0.21 | | | + | – | – | ++ |

TABLE 3-continued

| Mutation | Expression (% of wt) | trkC-binding (IC50 mut/IC50 wt) NIH3T3 | IA | gp75-binding (IC50 mut/IC50 wt) IA | Neurite extension PC12 trkC | trkB | trkA | Phosphorylation PC12 trkC |
|---|---|---|---|---|---|---|---|---|
| V48A | 30 | 0.62 ± 0.06 | | | + | – | – | ++ |
| K49A | 31 | 1.06 ± 0.21 | | | + | – | – | ++ |
| E59A R61A | 104 | 1.21 ± 0.09 | | | + | – | – | ++ |
| K58A/E59A/R61A | 110 | 1.68 ± 0.77 | 1.5 ± 0.39 | 1.31 ± 0.01 | + | – | – | ++ |
| K64A/N65A/D72A | 52 | 1.13 ± 0.26 | | | + | – | – | ++ |
| D71A/H74A/N76A | 5 | 0.65 ± 0.20 | | 0.60 ± 0.06 | + | – | – | ++ |
| D71A/K73A/H74A | 43 | 0.98 ± 0.37 | | 5.54 ± 1.85 | + | – | – | ++ |
| Q78A | 80 | 1.24 ± 0.26 | | | + | – | – | ++ |
| N93A/N94A/L96A | 55 | 1.01 ± 0.17 | | | + | – | – | ++ |
| K95A | 122 | 1.13 ± 0.34 | | 1.13 ± 0.13 | + | – | – | ++ |
| NGFswap (S2) (ENNKLVG (SEQ ID NO:19 > DGKQAA (SEQ ID NO:20)) | 87 | 0.96 ± 0.09 | | | + | – | – | ++ |

TABLE 4

| Neurotrophin | DRG (% of NT-3 + BDNF + NGF) | NG (% of NT-3 + BDNF) | SYMP (% of NGF) |
|---|---|---|---|
| NT-3 | 12.9 ± 1.9 | 41.8 ± 11.6 | 1.1 ± 0.5 |
| BDNF | 35.4 ± 1.6 | 65.4 ± 19.7 | N.D. |
| NGF | 53.7 ± 2.8 | N.D. | 100.0 ± 3.7 |
| NT-3 + BDNF | 53.7 ± 2.2 | 100.0 ± 1.8 | N.D. |
| NT-3 + NGF | 66.5 ± 0.6 | N.D. | N.D. |
| NT-3 + BDNF + NGF | 100.0 ± 0.8 | N.D. | N.D. |
| D15A | 11.4 ± 0.4 | 46.6 ± 10.0 | 1.4 ± 0.6 |
| S1 | 69.3 ± 4.5 | 46.0 ± 12.4 | 91.9 ± 5.7 |
| MNTS-1 | 93.0 ± 5.6 | 86.4 ± 12.4 | 100.3 ± 6.7 |

Example 3

Generation, purification, and characterization of N-terminal NGF variants

Several charged and uncharged residues are conserved among NGF proteins from other species. In particular, His4, Pro5, and His8 are conserved in 7 of 8 known NGF sequences; Arg9 exists only in human and chicken NGF while Met predominates at this position of NGF of other species. Ten mutants were generated by oligonucleotide-directed mutagenesis that either: 1) replaced some of the charged residues of the N-terminus of hNGF with alanine individually or together, 2) replaced His4 with negatively charged aspartic acid which resides in position 3 of the N-terminal hBDNF sequence (65), or 3) generated chimeric hNGF molecules which contained the first 5 or 6 residues of hBDNF or hNT3, respectively, or other variable regions of hNT3. The resulting mutant constructs were generated in vectors containing a human CMV promoter (70) and were expressed transiently in human 293 cells as described below.

Purified recombinant (1–118), (6–118), and (10–118) were purified from transfected CHO cell line conditioned media utilizing reversed-phase HPLC and high performance ion-exchange chromatography as described by Burton et al. (1992) (48) and Kahle et al. (1992) (49), and characterized by N-terminal sequence analysis, SDS-PAGE and amino acid analysis (data not shown). These processed variants result from in situ proteolysis during conditioning of the CHO cell media by as of yet uncharacterized proteolytic enzymes or processing pathways. The purity of each form was 99% based on SDS-PAGE and the concentration was determined by quantitative amino acid analysis. Purification and analysis of the H4D mutant 2(20 μg from 300 ml media) and the N-terminal hNT3/hNGF mutant 6 (5 pg from 300 ml media) was performed from serum-free media conditioned by transfected 293 cells (see below) as just described for the N-terminal truncated variants.

Mutagenesis was performed by the oligonucleotide-directed method (72) with modifications as indicated in the BioRad Muta-Gene kit (66); BioRad, Richmond, Calif.). The mutations were verified by DNA sequencing of single stranded phagemid clones by the chain termination method (73). The hNGF mutants were expressed in conditioned media following transient transfection of human 293 cells (68) (70). The media used for collection was 50:50 F12/DMEM serum-free media containing the N2 supplement and was collected following 48 hours in the serum-free media. The conditioned media was concentrated 10-fold using Amicon concentrators. The concentration of hNGF mutants was determined by an enzyme-linked immunoassay (ELISA) utilizing purified rabbit anti-hNGF polyclonal antibodies. The concentration of each mutant varied from 3–8 μg/ml. Each mutant was expressed at least three times and the concentration determined by ELISA 2–3 independent times.

Mutants were also analyzed by metabolic labelling of transfected 293 cells (60 mm plates, 1.2 ml media) by the addition of 200 μCi each of $^{35}$S-methionine and cysteine (Amersham). After 18 hrs, media is collected and reacted with either rabbit anti-hNGF polyclonal antibody or mouse monoclonal antibody for 3–4 hrs at 4° C., collected by precipitation with Protein-A beads (Pharmacia), and applied to 15% acrylamide SDS-PAGE gels (Novex). Following electrophoresis the gels were dried and placed next to X-ray film. Non-radiolabelled mutants were produced as described above and 0.1 μg aliquots were lyophilized, redissolved in SDS-PAGE sample buffer, electrophoresed on same gels, and transported onto nitrocellulose according to standard protocols (BioRad). The blot was treated with rabbit anti-hNGF polyclonal or mouse anti-hNGF monoclonal antibody overnight at 4° C., washed, and mutants detected with alkaline phosphatase-coupled goat anti-rabbit or anti-mouse IgG antibodies.

Receptor Binding, trkA Autophosphorylation, and PC12 Neurite Outgrowth Assays

[$^{125}$I]hNGF was produced using the Enzymobead method (BioRad), according to the method of Escandon (71). The specific radioactivity, determined by TCA precipitation of aliquots of the starting reaction mixture and gel filtrationchromatographed [$^{125}$I]hNGF, averaged 60–90 μCi/μg. Receptor binding assays were performed overnight at 4° C. on NIH3T3 cells recombinantly expressing rat trkA cells (Kindly supplied by Dr. Luis Parada), p75-expressing A875 human melanoma cells (ATCC), and rat PC12 cells (Kindly supplied by Dr. Louis Reichardt) as described for trkB-expressin NIH3T3 cells (23). The concentration of NIH3T3-trkA and A875-p75 cells used was 1×10$^6$ cells per ml; 5×10$^5$ cells per ml for PC12 cells. The final concentration of [$^{125}$I]hNGF was 50 pM in a volume of 0.2 ml. The non-specific binding, defined as the [$^{125}$I]hNGF bound in the presence of 1×10$^6$ M unlabelled hNGF, varied between 15–25% in most cases for the NIH3T3 trkA cells, 20–35% for the p75-A875 melanoma cells, and 20–30% for the trkA+p75 PC12 cells using the filter binding assay. The data was fitted to a displacement isotherm and an IC$_{50}$ was calculated utilizing a 4-parameter equation within the Kaleidagraph program. In some instances receptor binding was performed with cells at 25° C. for 90 min, and bound [$^{125}$I]hNGF was separated from free by sucrose cushion-centrifugation.

Autophosphorylation of trkA was performed at 37° C. for 5 min and the extent of phosphorylation was determined by a variation of the method described by Kaplan (19). Triton X-100 lysed trk A cells were immunoprecipitated with agarose bead-immobilized antiphosphotyrosine monoclonal antibody 4G10 (UBI), electrophoresed on SDS-PAGE (8% acrylamide-Novex), immunoblotted, and probed with rabbit anti-trkA polyclonal antibody (Kindly provided by Dr. David Kaplan). Detection of trkA was by alkaline phosphatase (AP)-coupled goat anti-rabbit IgG antibody (TAGO). PC12 cells were grown to 20–30% confluency on Primaria polycationic 24-well plates, the media changed to serum-free DMEM high glucose supplemented with N2 containing wild type or mutant variants of hNGF. After 48 hours, the number of cells projecting neurites longer than two cell bodies were counted in a representative visual field and expressed as a percentage of the total cells within the field, usually 100–140 cells. The activity of each mutant and NGF control was determined at least twice in separate experiments. The percent of responsive cells at maximal concentrations of hNGF varied from 55–75% between experiments with the mean of 63% calculated from 13 determinations. To account for the variation in the maximal response between experiments, this mean value was used to normalize all the data.

Inhibition of [$^{125}$I]hNGF Binding to trkA and p75 Cells by a Monoclonal Antibody to hNGF Under the same conditions as the filter binding assay described above, increasing concentrations of an anti-hNGF monoclonal antibody were added to 25 pM [$^{125}$I]hNGF and incubated for 30 min at 25° C. Then 1×10$^6$ cells per ml of either NIH3T3-trkA or A875-p75 cells were added (0.2 ml final volume) and incubated for 4° C. overnight with vigorous mixing. The samples were then diluted and filtered on Whatman GF/C filters and counted.

Results

The results are shown in Tables 5 and 6.

TABLE 5

Summary of relative receptor binding affinities of hNGF structural variants

| | | Receptor Binding | | | | | |
|---|---|---|---|---|---|---|---|
| | | trk | | p75 | | trk + p75 | |
| Structural variant | Residues changed | IC$_{50}$$^a$ | mut/NGF$^b$ | IC$_{50}$ | mut/NGF | IC$_{50}$ | mut/NGF |
| hNGF(1-118) | None | 0.8 | 1.0 | 3.0 | 1.0 | 0.5 | 1.0 |
| hNGF(6-118) | Deletion S1-P5 | 7.2 | 9.0 | 3.0 | 1.0 | 1.3 | 2.6 |
| hNGF(10-118) | Deletion S1-R9 | 210.0 | 265.0 | 32.0 | 10.7 | 41.0 | 82.0 |
| mNGF(1-118) | S3T,I6V,R9M,M37T,G40A, K502,D60A,P61S,D65E, M92T,G94E,V117T,A120G | 1.8 | 2.2 | 4.1 | 1.4 | 0.6 | 1.2 |
| hNGFwt | None | 1.2 | 1.0 | 2.0 | 1.0 | 0.5 | 1.0 |
| Mut 1 | H4A | none | >40$^c$ | 1.4 | 0.7 | 1.8 | 3.6 |
| Mut 2 | H4D | >1000$^c$ | ≧1000$^c$ | 1.1 | 0.6 | 4.3 | 8.6 |
| Mut 3 | R9A | 2.0 | 1.5 | 1.9 | 1.0 | 1.8 | 3.6 |
| Mut 4 | H4A,H8A,R9A | none | >40$^c$ | 3.1 | 1.6 | 3.9 | 7.8 |
| Mut 5 | S1H,S3D,H4P,P5A,I6(-) H8R | none | >40$^c$ | 2.1 | 1.0 | 1.7 | 3.6 |
| Mut 6 | S1Y,S2A,S3E,P5K,I6S,F7S | >1000$^c$ | >1000$^c$ | 3.5 | 1.8 | 1.0 | 2.0 |
| Mut 7 | R59K,D60E,P61A,N62R, D65K,S66N | 0.5 | 0.4 | 1.6 | 0.8 | 0.2 | 0.4 |
| Mut 8 | M92D,D93E,G94N,+N94/95, Q96L,A97V,A98G | 1.8 | 1.3 | 8.1 | 4.1 | 1.4 | 2.5 |

TABLE 6

Summary of biochemical and biological activities supported by NGF structural variants

| | trkA autophosphorylation$^a$ | | |
|---|---|---|---|
| | Maximal level at 1 × 10$^{-8}$M | PC12 neurite outgrowth$^b$ | |
| Structural variant | mutant/hNGF | EC$_{50}$ ng/ml | mutant/hNGF |
| hNGF(1-118) | 1.0 | 0.14 | 1.0 |
| hNGF(6-118) | 1.38 | 0.22 | 1.6 |
| hNGF(10-118) | 0.38 | 4.2 | 30.0 |
| mNGF(1-118) | 1.08 | — | — |
| hNGF wt | 1.0 | 0.20 | 1.5 |
| Mut 1 | 0.47 | 3.1 | 21.4 |
| Mut 2 | 0.14 | 5.0 | 35.7 |
| Mut 3 | 0.92 | 0.30 | 2.1 |
| Mut 4 | 0.23 | 12.0 | 85.7 |
| Mut 5 | 0.07 | 16.0 | 114.3 |
| Mut 6 | 0.07 | 12.0 | 85.7 |

TABLE 6-continued

Summary of biochemical and biological activities supported by
NGF structural variants

|  | trkA autophosphorylation[a] | | PC12 neurite outgrowth[b] |
|---|---|---|---|
|  | Maximal level at $1 \times 10^{-8}$ M | | |
| Structural variant | mutant/hNGF | $EC_{50}$ ng/ml | mutant/hNGF |
| Mut 7 | 0.88 | 0.24 | 1.7 |
| Mut 8 | 1.29 | 0.12 | 0.9 |

[a]TrkA autophosphorylation was performed at $1 \times 10^{-10}$, $1 \times 10^{-9}$, and $1 \times 10^{-8}$ M as described in the Experimental Procedures and the legends for FIGS. 2 and 5. The values represent the ratio of densitometric area of the immmunoblotted autophosphorylated $p140^{trkA}$ band following stimulation of NIH3T3-trkA cells by hNGF structural variants versus (1-118)hNGF (truncated hNGF) or wild type hNGF (mutants).
[b]PC12 cell differentiation was determined by neurite outgrowth described in the Experimental Procedures and the legend to FIG. 6. The $EC_{50}$ values and ratios are taken from the data in FIG. 6 and represent the average from two separate experiments for each mutant.

To initiate characterization of the N-terminal amino acid residues necessary for full hNGF activity, the (6–118) truncated form of hNGF was isolated from conditioned media of CHO cells recombinantly-expressing hNGF. The nine amino acid truncated form (10–118)hNGF was generated by limited proteolysis as described (48). The (6–118) and (10–118) hNGF were purified by high-performance ion-exchange chromatography (HPIEC) and characterized by reverse-phase HPLC, N-terminal sequence analysis, SDS-PAGE, and amino acid analysis (Data not shown).

The relative potency of purified (6–118)hNGF to displace [$^{125}$I]hNGF from cell lines expressing trkA, p75, and trkA+p75 were then compared to those of (10–118)hNGF, (1–118) or(1–120)hNGF, and (1–118)mNGF(FIG. 9). As suggested by their equivalence in bioactivity (74), initial experiments indicated no difference in binding properties of (1–118) versus (1–120)hNGF (not shown). The relative $IC_{50}$'s for hNGF and trkA (80–100 pM), p75 (2–300 pM), and PC12 cells (50 pM) are within a factor of 2–3 to the $IC_{50}$ and Kd values reported by others (49) (75) (76) (20, 21). Consistent with Vroegop et al., we observe a slightly higher affinity of hNGF to p75 than commonly reported ($IC_{50}$=0.3 nM vs 1–2 nM).

Deletion of the first five amino acids results in a 9-fold loss of binding to NIH3T3 cells recombinantly expressing rat trkA while little difference in binding occurs with p75-expressing A875 human melanoma cells (no change) or with PC12 cells expressing trkA+p75 (3-fold). In contrast, a 265- and 82-fold loss of binding to trkA and PC12 cells, respectively, were observed for (10–118)hNGF compared to (1–118)hNGF while a 10-fold loss in binding to p75 occurs. The intermediate potency of displacement by (10–118) hNGF observed with BC12 cells, relative to the trkA and p75 cells, suggests contributions by both receptors to the profile of the displacement isotherm (FIG. 9C). Recombinantly expressed rat trkA cells and radioiodinated human NGF were utilized in the present study whereas a prior study of (10–1 18)hNGF by Kahleet al. (1992) used human trkA-expressing cells and radioiodinated mouse NGF. Thus, similar differences between (1–118)hNGF and (10–118) hNGF binding are observed regardless whether human or rodent trkA or radiolabelled NGF are utilized during the analysis. Furthermore, (1–1 18)hNGF has 2–3 fold greater affinity to either human or rat trkA than does (1–188)mNGF whether radioiodinated mouse or human NGF represents the displaceable tracer. Autophosphorylation of trkA (FIG. 10), and PC 12 cell differentiation activities (Table 6) of (6–118) hNGF were similar to those elicited by (1–118)hNGF. However, (10–118)hNGF is at least 10-fold less potent as (1–118)hNGF in trkA autophosphorylation and is 80-fold less potent in stimulating PC12 cell neurite outgrowth (FIG. 10; Table 6), consistent with previous results (48) (49). Taken together, these results suggest that the first five amino acids of the N-terminus are important for full hNGF-trkA binding activity but potent receptor activation and bioactivity are mostly retained. The additional loss of the next four residues appears to be more deleterious to trkA binding and activation, as well as having some effect on the binding to p75.

The mutant forms of HNGF can be detected by metabolic labelling followed by immunoprecipitation, or immunoblot analysis of non-labelled conditioned media, and are represented as fully-processed polypeptides of 14 kD (FIG. 11). The concentration of each of the mutants was determined by an ELISA utilizing a polyclonal anti-hNGF antibody. Similar levels of expression, together with the predominant presence of a single processed species recognized by a polyclonal antibody in three different types of immunoreactivity, suggests that the mutants share structural stability similar to that of wild-type hNGF.

The replacement of all three charmed amino acids to alanine (Mut 4:H4A+H8A+R9A) resulted in the loss of detectable competitive displacement of [$^{125}$I]hNGF from trkA at 4° C. over a concentration range of wild-type hNGF that completely displace the tracer ($IC_{50}$=$1\times10^{-10}$ M; maximum displacement =$1\times10^{-9}$ M, FIG. 12, top, Table 5). The loss of receptor binding also correlates with the at least 10-fold loss of potency and 4–5-fold apparent reduction in efficacy of maximal trkA autophosphorylation. Mutant 4 has a 85-fold lower $EC_{50}$ of PC 12 differentiation relative to (1–118)hNGF (FIG. 14), consistent with the PC12 receptor binding profile which appears to reflect displacement largely from p75 and a non-displaceable component which may reflect lower affinity binding of the mutant to trkA (FIG. 12, bottom).

His4 and Arg9 variants were then analyzed individually. The N-terminal region of both hNT3 and hBDNF contains a histidine which suggests the possibility of a conserved functional role. Replacement of His4 of hNGF by either alanine (mutant 1) or aspartic acid (mutant 2) result in dramatic loss of trkA binding, autophosphorylation, and PC12 cell differentiation (FIGS. 12, 13, 14). As suggested by the variation in sequence between hNGF and other NGF species at position 9, the mutation R9A did not have large effects on trkA or p75 activities. However, a slightly lower potency was observed for trkA phosphorylation and PC12 cell differentiation (FIG. 12, top, middle, FIGS. 13 and 14). At 25° C., the PSA and H8A variants displayed a 3-fold and 1.5-fold loss of trkA binding relative to hNGF, respectively, whereas H4D lost approximately 40-fold binding potency; no change in binding to p75 was observed. All of the above mutants displayed less than 2-fold loss of binding to p75 whether at 4° C. or 25° C., suggesting that global structural effects resulting from the mutagenesis are minimal.

To test whether the specific N-terminal sequence of hNGF is required for neurotrophin interaction with trkA, chimeric mutants (mutants 5 and 6) were generated by replacing the N-terminus of hNGF (SSSHPIF) (SEQ ID NO:11) with that of hBDNF (HSDPA) (SEQ ID NO:18) or hNT3 (YAEHKS) (SEQ ID NO:12). These mutants would therefore retain the dibasic His8, Arg9 residues of hNGF. Even at 10-fold higher concentrations of (1–118)hNGF which result in complete receptor displacement at 4° C., the resulting chimeric neurotrophins were unable to displace [$^{125}$I]hNGF from trkA (FIG. 12A) and are less potent than mutants 1 and 2 in eliciting trkA autophosphorylation activity (FIG. 13). Binding interactions of these mutants with p75 are indistinguishable from those of (1–118)hNGF while the PC12 receptor displacement may be mostly a p75 interaction (FIG. 12, bottom). Similar to the triple alanine mutant 4, the N-terminal chimeric mutants were the weakest inducers of PC12 cell differentiation when compared to all structural variants of hNGF; the $IC_{50}$ shifted nearly 100-fold. These results indicate a requirement for the specific N-terminal sequence of hNGF for high affinity binding and agonist activity involving trkA but not for binding to p75.

To verify that the N-terminal sequence variants are capable of restricting hNGF from high affinity trkA interactions while retaining overall structure, the H4D mutant 2 and the hNT3/hNGF mutant 6, were expressed in large amounts and purified. At the highest concentration possible, 2000-fold greater ($2 \times 10^{-7}$ M) than the $IC_{50}$ for (1–118) hNGF ($IC_{50}=1 \times 10^{-10}$ M), only 30% and 10% displacement of [$^{125}$I]NGF occurred from trkA at 4° C. for mutant 2 and 6, respectively, while binding profiles of p75 were similar (FIG. 15). Consistent with the results shown in FIG. 13, the purified mutants were significantly less potent than (1–118) hNGF in the ability to activate trkA autophosphorylation. These results suggest that overall structural stability is maintained following either of these amino acid replacements and confirms that the loss of high affinity trkA binding and autophosphorylation are due to these specific modifications.

Chimeric mutants were also generated to initially compare the role of two other variable regions of hNGF as possible determinants of trkA receptor specificity. Six residues within beta-turn variable region 3 (Arg59-Ser66) and seven residues within beta turn variable region 5 (Met92-Ala98) were exchanged with the corresponding hNT3 residues in mutants 7 and 8, respectively. Mutant 7 was slightly more potent in displacing [$^{125}$I]NGF than hNGF from trkA while mutant 8 bound less well to p75 (3–5 fold). Otherwise these mutants displayed little difference from hNGF in their trkA and p75 binding profiles, ability to support trkA autophosphorylation or PC12 neurite outgrowth (FIGS. 12, 13, 14). These results suggest that regions 3 and 5 contribute less to the trkA binding interaction than does the N-terminus. The lower affinity of mutant 8 to p75 may represent structural changes around the conserved residue Lys95, shown to interact with p75 (54).

To determine the relative levels of expression of the $M_r=14,000$ fully processed form of the structural variants of hNGF, monoclonal and polyclonal antibodies to hNGF were tested for their ability to recognize mutants by immunoblotting (FIGS. 11 and 12). When equal quantities of the N-terminal mutants expressed in conditioned media were immunoblotted, several lost the ability to be recognized by the monoclonal antibody whereas all were recognized by the affinity purified polyclonal antibody. The H4D mutant, and the hBDNF or hNT3 N-terminal chimeric mutants displayed no immunoblot signal whereas the H4A+H8A+H9A mutant was less deleterious (FIG. 16A). H4A or R9A mutations did not affect antibody binding. The monoclonal antibody was then tested for the ability to compete with the binding of [$^{125}$I]NGF to trkA or p75. Increasing concentrations of antibody were inhibitory to the binding of [$^{125}$I]NGF to either receptor; an $IC_{50}=1 \times 10^{-9}$ M vs $4 \times 10^{-8}$ M indicates that it is 40-fold more effective in blocking binding of hNGF to trkA than to p75. These results suggest that the N-terminus forms at least part of the epitope of the hNGF monoclonal antibody, and the binding of the antibody to HNGF blocks its interaction with trkA with relatively high affinity. The weaker inhibition of the binding to p75 suggests that either a lower affinity epitope outside of the N-terminus may contribute to hNGF-p75 binding contacts, or that steric inhibition of the antibody may partially interfere with p75 binding. Preliminary studies suggest that a weaker binding epitope for this antibody does indeed exist in the beta turn 3 region represented by the hNT3/hNGF chimeric mutant 7. The role of this region in the binding of hNGF to p75 and trkA is presently being investigated. Although it could be argued that the loss of trkA binding in the presence of the antibody is due to the binding to a secondary epitope or is due to steric inhibition, the data are consistent with the preferential loss of trkA versus p75 binding observed for several of the N-terminal variants presented above.

Example 4

Generation and characterization of hNGF amino acid variants: hNGF and hNT3 pan-neurotrophins Identification of target residues for mutational analysis NGF and its neurotrophin family members NT3, BDNF and NT4/5 share approximately 56% sequence identity. The receptor binding specificity may be determined in part by the amino sequence differences among the neurotrophin family members. These residues may bind directly to the trk receptor, or function as inhibitory constraints on the trk interactions of other variable, or conserved residues. Domain-swap mutants of hNGF were generated between hNGF and hNT3 to test the role of the divergent residues in determining trk receptor specificity. A comparison of neurotrophin primary sequences reveals that there are 7 regions of 7–10 amino acids each which contain most (80%) of the sequence differences (FIGS. 8, 18A and 18B). Between hNGF and hNT3, 52 of 120 amino acids differ. Forty-one of these 52 differences (79%) occur within the 7 divergent regions. Among 9 NGF species including man, birds, snakes and frogs, 24 of the 52 residues are conserved suggesting a contribution to the trkA binding specificity. An examination of the x-ray crystal structure of murine NGF reveals that four of the variable regions/domains are structurally characterized as beta-turns, one variable region is a beta-sheet, and the last two are the amino and carboxy termini. Each of the divergent regions contains several charged and polar side chains accessible to the solvent and capable of interacting with receptors. Thirteen chimeric, or domain-swap, mutants were generated by replacing several residues, or all, of the individual seven variable regions of hNGF with the corresponding domain of hNT3. Two additional regions of less divergence were also replaced: pre-variable region I and 4. Thus a total of 90% of the divergent amino acid residues were evaluated for their role in determining trkA and trkC specificity. The chimeric mutants were generated by oligonucleotide-directed mutagenesis and mammalian cell expression as described in example 3.

The selection of individual residues of hNGF for mutagenesis was determined primarily by their position within the x-ray crystal structure of murine NGF. It was assumed that minimal structural chance results from the sequence differences between human and mouse NGF since the replaced residues are mostly functionally conserved (10/12). Computer- generated modelling of murine NGF, based on the x-ray crystal structure coordinates and described in example 1, reveals amino acids which project side chains into the solvent and could interact with trkA and gp75 receptors. Some of these include variable residues which were significantly modified by the domain-swap mutations, however, many represent residues conserved between hNGF and hNT3 within variable and conserved regions. Residues predicted to have minimal side-chain exposure, such as those implicated in forming the dimeric interface (F12, V14, W21, F49, Y52, F54, W76, T85, F86, W99, F101, T106, A107, V109, V111), hydrophobic interior (V36, V38, F53, I71, A89, I102, and I104), and structurally-dependent and buried hydrogen bonding (Q51, S78, T91, R100), were minimally modified. Of the disulfide bond-forming cysteine residues and glycines and alanines, only A97 was modified. Exceptions were made in the following cases: residues I30 and Y52 which have surface side chains although they appear at the dimer interface, residues L39, L90, M92 and A97 which also form a hydrophobic surface patch, and D16, K25, D30, E55, K57, R59, R69, D72, H75 which exhibit some side-chain solvent exposure although hydrogen bonded. Most residues were changed to alanine (64); in some instances other replacements were made to maintain structure while testing the role of a specific functionality in receptor interactions.

Production and receptor binding characterization of hNGF variants

Mutagenesis, expression, and protein characterization of hNGF variants was performed as described in example 3. Following oligonucleotide-directed mutagenesis, all mutants were verified by dideoxynucleotide sequencing. The hNGF mutants were expressed in human 293 cells (FIG. 11A, B) and following Amicon concentration (10×) and ELISA quantification, most hNGF variants were observed to have been expressed at levels similar to normal hNGF controls (5–25 $\mu$g/ml), with the exception of mutants which replaced variable regions 2 or 3 (0.6–1 $\mu$g/ml). Both of these chimeric molecules result in insertion or deletions of proline residues, plus other significant changes in side chain functionality, and thus the low recoveries may reflect structural instability. Nevertheless, available quantities permitted the determination of binding affinities of the hNGF variants to trkA and gp75 receptors. The binding affinity of each hNGF variant was determined by competition binding utilizing immunoadhesion constructs of the trk and gp75 receptors (88), and radioiodinated neurotrophins as described in example 2. Each hNGF variant was expressed in 293 cells at least twice and binding experiments performed 2–3 times for each transfection. The relative affinity compared to normal hNGF is expressed as the ratio of the mean $IC_{50}$ for all determinations of a variant to the $IC_{50}$ of hNGF.

TrkA autophosphorylation activity and PC12 cell differentiation bioassay

Biochemical activation of trkA kinase by hNGF variants was determined by assessing trkA autophosphorylation as described in example 3. A quantitative assay was developed (89) which permits dose-dependent determinations of the $EC_{50}$ for trkA autophosphorylation. A trkA receptor variant, containing a peptide epitope tag derived from a Herpes simplex surface protein, was stably expressed in CHO cells in 96 well plates (88). The affinity of the epitope-tagged trkA for hNGF is identical to that of the normal receptor (88). The cells (duplicate wells for each concentration) are stimulated with 8 increasing concentrations of hNGF variant (10 pM–10 nM) for 10 minutes at 37° C. The cells are lysed with Triton X-100 lysis buffer as described in example 3, and transferred to a plate coated with a monoclonal antibody directed to the epitope tag. After binding, the captured trkA is then reacted with a HRP-conjugated antiphosphotyrosine monoclonal antibody, and the color reaction developed. The absorbance is then read and plotted versus concentration. The $EC_{50}$ for hNGF is 100–120 pM. Differentiation of PC12 cells was performed as described in example 3, however, cells were first grown or primed in NGF for 7–10 days. Cells bearing neurites were then harvested and plated in 24 well dishes in normal growth media, and either in the presence or absence of hNGF variant. The percentage of cells bearing neurites after 72 hours were quantifyied as described in example 2. hNGF/hNT3 pan-neurotrophic variants were evaluated for hNT3-like trkC bioactivity in trkC-transfected PC12 cells which did not respond to hNGF (Kindly provided by Drs. Pantelis Tsolfous and Luis Parada, NCI).

Results

Mutagenic analysis of variable residues by hNGF/hNT3 chimera

Thirteen chimeric mutants were generated by replacing several residues, or all, of each of the 7 variable regions of hNGF, with the corresponding region of hNT3 (See FIGS. 8, 18A,B). Two less variable regions, one within beta sheet A and the other within a conserved beta-turn connecting beta sheets B and C, were also replaced. Competition binding experiments were performed with the hNGF variants displacing [$^{125}$I]hNGF from trkA or gp75 immunoadhesion fusion proteins. These receptors contain the extracellular domain of trkA or gp75, and the Fc portion of human IgG. These immunoadhesions bind hNGF with affinities similar to the holo-trkA and p75 receptors, and display a similar rank order of affinities for the neurotrophins (FIG. 19A,B). The $IC_{50}$ for each hNGF variant was averaged and expressed as a ratio of the $IC_{50}$ determined for normal hNGF ($IC_{50}$ HNGF=100 pM; FIG. 23A). The most significant effect on the trkA binding, as previously described (FIGS. 12, 15), is a nearly 300-fold loss of binding affinity due to the N-terminal domain swap with hNT3. A 2–3 fold loss of binding is observed for the three residue chance within pre-variable region 1 (beta sheet A: V18E+V20L+G23T). Less than 2-fold loss of trkA binding is observed for other hNGF variants whereas increased binding is observed for the variable region 3 chimeric mutant (beta-turn 3) and the C-terminus (FIG. 20A). Consistent with the loss of trkA binding affinities, dose-response curves for trkA autophosphorylation and PC12 cell differentiation (neurite outgrowth) indicate losses of activity by the N-terminal and pre-variable region 1 variants (FIG. 21A,B). The binding to gp75 is reduced by 5 and 7-fold by the exchange of variable region 1 and pre-variable region 4 of hNT3. respectively (FIG. 20B). A 2–3 fold loss of gp75 binding is also observed for the variable region 5 mutant. The loss of gp75 binding exhibited by the VI exchange is likely due to exchange of K32 to R, K34 to H, and E35 to Q since alanine replacements of these residues result in loss of gp75 binding (FIG. 8; (54)). These results indicate that binding interactions of hNGF to trkA and gp75 involve some of the variable neurotrophin residues.

The loss of trkA binding and receptor activation suggests that the variable residues within the N-terminus and pre-variable region 1 contribute to trk receptor specificity. This possibility was tested by determining receptor binding to trkC-IgG immunoadhesion and neurite outgrowth in trkC-transfected PC12 cells which do not respond to NGF. Surprisingly, trkC interactions were not conferred by the N-terminus of hNT3 (Mutant 6, FIG. 22A,B), however, the four amino acid swap in variable region 4 of hNGF (T81K, H84Q, F86Y, K88R) resulted in a significant trkC interaction (FIG. 22A,B). The lower trkC affinity and potency of neurite outgrowth of this variant indicates that other regions likely contribute to efficient trkC interactions. Pre-variable region 1 mutant is now being evaluated for trkC interactions, as are the contributions of the individual residues within variable region 4. However, overlapping mutations within variable region 4 suggest that multiple residues of V4 may be necessary for the trk specificity. For example, the beta-turn 3/4 variant, exchanging three variable residues which overlaps at T81K (S73, Y79Q, T81K), activates neurite outgrowth in trkC-PC12 cells only 5–10% as well as the variable region 4 mutant (FIG. 22B). Nevertheless, trk function is affected by the alanine mutant Y79A+T81A, further implicating the variable residues of this region in trk receptor interactions. The retention of trkA activities by the variable region 4 mutant suggests that the 4 hNT3 residues are compatible with trkA binding, however, the equivalent hNGF residues may pose an inhibitory constraint on the interaction of hNGF with trkC.

Although the N-terminal domain of the neurotrophins appears not to be a general trk specificity domain, this region of hNGF appears to be a major determinant of trkA interaction. The replacement of the first six residues of NT3 with the first seven residues of hNGF results in a pantropic variant which binds and activates both trkA and trkC with high affinity and potency (FIGS. 24, 25 and 26). Furthermore, it retains high affinity binding with gp75. Thus it may possible to generate an effective trkA/trkC pantropic neurotrophin starting with hNT3 and including variable regions of hNGF such as the N-terminus, V2, V3, V4, and V5. Conversely, hNGF may be modified to contain similar trkA/trkC pantropic properties by exchanging variable residues within hNT3 beta sheet 1 (C1) and V4. Although the hNGF/hNT3 chimera replacing variable region 2 did not result in gain of trkC activity, as did result in small loss of trkA binding (1.5 fold). The reciprocal domain swap, replacing variable region 2 of hNT3 with the corresponding hNGF domain, is now being tested for gain of trkA activity and is a candidate trkA/trkC pantrophin.

Mutagenic anaylsis of individual variable and consented hNGF residues: Structural model of hNGF residues which interact with trkA and gp75.

Using the crystal structure of murine NGF as described above, we evaluated by point mutagenesis 45 residues of hNGF, many of which have side chain functionalities exposed to the solvent and are capable of trkA or gp75 interactions. Competition binding analysis reveals that H4, P5A, S13, D30, I31, Y52, R59, R69, Y79, T81, and R103 mutations affect trkA binding 1.8–10 fold, while mutations of residues E41, K57, D72, N77 increase binding 1.5–2 fold (FIG. 27). These results indicate that these residues are involved in trkA interactions and suggests that variants could be generated from both the variable residues (H4, P5, I31, R59, Y79, T81) and conserved residues (S13, D30, Y52, R69, R103) that could effect the trk specificity. Mutations in residues F12, I31, K32+K34+E35, K50, Y52, R69, K74, H75, K88, L112, S113, R114, and K115 results in 3–>50-fold losses in gp75 binding (FIG. 30). In particular, no displacement was observed in the presence of 10 nM mutants representing changes in residues F12, K32+K34+E35, Y52, R69, K88, and R114+K115, suggesting that these residues are critical determinants of gp75 binding.

Autophosphorylation analysis using epitope-tagged trkA indicated decreases in the potency of activation by 1.5–6 fold by mutations in residues H4, P5, D30, Y52, R69, Y79+T81, and R103 (FIG. 28). Significant (20–60%) decreases in the efficacy of trkA autophosphorylation are observed for all of these mutations except for residue F12. These results are consistent with the potency of PC12 cell differentiation; 2–50 fold decreases in the $EC_{50}$ of neurite outgrowth are observed for mutations in residues H4, F12, D30, Y52, R69, Y79+T81, and R103. Other hNGF variants are presently being evaluated, including mutations of P5. Interestingly, residues in which 5 mutations minimally affect both the trkA binding and the potency of trkA autophosphorylation can reduce the efficacy of trkA autophosphorylation. The decrease of trkA autophosphorylation may explain the decreased potency of PC12 cell differentiation elicited by mutations of R69 and Y79+T81. Alternatively, mutations in R69 greatly reduce p75 binding; the role of p75 in hNGF signal transduction is presently unclear loss of p75 interaction could contribute to a reduced biological effect. This possibility is being investigated with other hNGF variants which decrease hNGF binding to gp75.

Residues interacting with the trkA and gp75 receptors were modelled by computer-generated on the structure of murine NGF. Two major trkA interacting regions were found by this analysis: 1) The N-terminus (H4, P5), with unknown crystal structure, and 2) A surface formed by Y79, T81, H84 and R103 of beta sheets C and D. Residues V18, V20, G23, Y52, R59 and R69 of beta sheets A and B make some contributions to an extended surface which would wrap around the beta sheet strands. Near the area of Y52 and the beta sheet A residues are D30 and I31 of the second protomer. These two residues project relatively little surface area into the solvent, however, it is possible that they contribute to a continuous binding surface formed with the beta-sheet residues.

Two major p75 interacting regions were found: 1) Variable region 1 of one protomer and beta-sheet B and C of the other protomer, 2) Conserved residues within the C-terminus and beta-turn 3, also from different protomers. In contrast to the trkA-interesting residues within a cleft formed by the pairs of beta sheets, the p75 interacting residues appear to be well exposed. As shown by (54) K32 and K34 project from the variable region of beta-hairpin turn 1. We find the adjacent residues K50 and Y52 from the other protomer contribute to p75 binding. K88, which contributes significantly to the p75 binding, is in this region but is not highly exposed. The other binding surface is composed of K74 (beta-turn 3), R114 and K115 (C-terminus) of one terminus, and F12, R69 from the other protomer.

Other potential pantropic molecules are now being constructed and evaluated base on the mutagenesis analysis presented above. A pan trkA/trkC molecule can be generated by the following changes in hNGF: 1)pre-variable region 1 (V18E+V20L+G23T) plus variable region 4 (Y79Q+T81K+H84Q+F86Y+K88R); 2) pre-variable region 1 plus minimal residues replacements of variable region 4. A pan trkA/trkC molecule can be generated by replacing minimal changes within the first seven residues of the N-terminus of hNGF and replacing the first 6 residues of hNT3. Since H4 and P5 are conserved among NGFs and 2 hydrophobic residues in positions 6 and 7 are conserved, the following variants have been made: 1) YASHPIF(SEQ ID NO:13)-hNT3; 2) YAHPIF(SEQ ID NO:14)-hNT3; 3) YASHPIS(SEQ ID NO:15)-hNT3; 4) YAEHPIF(SEQ ID NO:16)-hNT3; 5) YAQHPIF(SEQ ID NO:17)-hNT3. A trkA/trkC pantrophin can be generated by replacing variable regions 2 or 4 or 5, or combinations of these elements, of hNT3 with the corresponding regions of hNGF. A trkA/trkB pantrophin can be generated by replacing the first 9 amino acid residues of hNT4/5 with the first 7 residues of hNGF, or in combination with replacement of residues within variable region 4 or pre-variable region 1.

References (1): Snider, W. D. & Johnson, E. M. (1989) Ann. Neurol.., 26, 489–506
(2): Barde, Y.-A. (1989) Neuron, 2, 1525–1534
(3): Davies et al., J. Neuroscience, 6, 1897 (1986)
(4): Davies A. M., Trends in Genetics 139–143 (1988)
(5): Maisonpierre, P. C., Belluscio, L., Squinto, S., Ip, N. Y., Furth, M. E., Lindsay, R. M. and Yancopoulos, G. D. (1990) Science 247, 1446–1451
(6): Rosenthal A, Goeddel, D. V., Ngyuen, T., Lewis, M., Shih, A., Laramee, G. R., Nikolics, K., and Winslow, W. (1990) Neuron 4, 767–773
(7): Hohn, A., Leibrock, i., Bailey, K., and Barde, Y.-A., Nature, 344, 339–341,1990
(8): Kaisho Y, Yoshimura, K. and Nakahama, K. (1990) FEBS Lett. 266, 187–191
(9): Ernfors, P., Ibanez, C. F., Ebendal, T., Olson, L., and Persson, H. (1990) Proc. Natl. Acad. Sci. USA 87, 5454–5458
(10): Jones, K. R. and Reichhardt, L. F. (1990) Proc. Natl. Acad. Sci. USA, 87, 8060–8064
(11): Levi-Montalcini, R. and Angeletti, P. U. (1968) Physiol. Rev., 48, 534–569
(12): Thoenen H., Bandtlow, C. and Heumann, R. (1987), Rev. Physiol. Biochem. Pharmacol., 109, 145–178
(13): Barde, Y.-A., Edgar, D. and Thoenen, H. (1982) EMBO J., 1, 549–553
(14): Leibrock, J., Lottspeich, F., Hohn, A., Hofer, M., Hengerer, B., Masiakowski, P., Thoenen, H., and Barde, Y.-A. (1989) Nature, 341, 149–152
(15): Holbook, F. et al., (1991) Neuron, 6, 845–858
(16): Berkemeier, L. R., Winslow, J. W., Kaplan, D. R., Nikolics, K., Goeddel, D. V. and Rosenthal, A (1991) Neuron, 7, 857–866
(17): Ip, N. Y., Ibanez, C. F., Nye, S. H., McClain, J., Jones, P. F., Gies, D. R., Belluscio, L., LeBeau, M. M., Espinsosa, R., III, Squinto, S. P., Persson, H. and Yancopoulos, G. D. (1992) Proc. Natl. Acad. Sci., 89, 3060–3064
(18): Martin-Zanca, D., Oskam, R., Mitra, G., Copeland, T. and Barbacid, M. (1989), Mol.Cell. Biol., 9, 24–33
(19): Kaplan, D. R., Martin-Zanca, D., and Parada, L. F. (1991) Nature, 350, 158–160
(20): Klein, R., Jing, S., Nanduri, V., O'Rourke, E., and Barbacid, M. (1991a) Cell 65, 189–197
(21): Kaplan, D. R., Hempstead, B., Martin-Zanca, D., Chao, M., and Parada, L. F. (1991) Science 252, 554–558
(22): Klein, R., Nanduri, V., Jing, S., Lamballe, F., Tapley, P., Bryant, S., Cordon-Cardo, C., Jones, K. R., Reichardt, L. F., and Barbacid, M. (1991b) Cell 66, 395–403
(23): Soppet, D., Escandon, E., Maragos, J., Middlemas, D. S., Reid, S. W., Blair, J., Burton. L. E., Stanton, B. R., Kaplan, D. R., Hunter, T., Nikolics, K. and Parada, L. F. (1991) Cell, 65, 895–903
(24): Squinto, S. P., Stitt, T. N., Aldrich, T. H., Davis, S., Bianco, S. M., Radziejewski, C., Glass, D. J., Masiakowski, P., Furth, M. E., Valenzuela, D. M., DiStefano, P. S. and Yancopoulos, G. D. (1991) Cell, 65, 885–893
(25): Lamballe, F., Klein, R. and Barbacid (1991), Cell, 66, 967–979
(26): Tsoulfas, P., Soppet, D., Escandon, E., Tessarollo, L., Mendoza-Ramirez, J.-L., Rosenthal, A., Nikolics, K. and Parada, L. F. (1993) Neuron, 10, 975–990
(27): Cordon-Cardo, C., Tapley, P., Jing, S., Nanduri, V., O'Rourke, E., Lamballe, F., Kovary, K., Klein, R., Jones, K. R., Reichhardt, L. F. and Barbacid, M. (1991), Cell, 66, 173–183
(28): Klein, R., Lamballe, F., Bryant, S., and Barbacid, M. (1992) Neuron 8, 947–956
(28a): Klein, R., Parada, L. F., Coulier, F. and Barbacid, M. (1989), EMBO J., 8, 3701–3709
(29): Ip, N. Y, Stitt, T. N., Tapley, P., Klein, R., Glass, D. J., Fandl, J., Greene, L. A., Barbacid, M. and Yancopoulos, G. D. (1993) Neuron, 10, 137–149
(30): Johnson, D., Lanahan, A., Buck, C. R., Sehgal, A., Morgan, C., Mercer, E., Bothwell, M. and Chao, M. (1986) Cell, 47, 545–554
(31): Radeke, M. J., Misko, T. P., Hsu, C., Herzenberg, L. A. and Shooter (1987) Nature, 325, 593–597
(32): Loetscher, H., Pan, Y.-C. E., Lahm, H.-W., Gentz, R., Brockhaus, M., Tabuchi, H., and Lesslauer, W. (1990) Cell 61, 351–359
(33): Smith, C. A., Davis. T., Anderson, D., Solam, L., Beckmann, M. P., Jerzy, R., Dower, S. K., Cosman, D., and Goodwin, R. G. (1990) Science 248, 1019–1023
(34): Schall, T. J., Lewis, M., Koller, K. J., Lee, A., Rice, G. R., Wono, G. H. W., Gatanga. T., Granger, G. A., Lentz, R., Raab. H., Kohr, W. J., and Goeddel, D. V. (1990) Cell 61, 361–370
(35): Mallet, S., Fossum, S., and Barclay, A. N. (1990) EMBO J. 9, 1063–1068
(36): Camerini, D., Walz, G., Loenen, W. A. M., Borst, J., and Seed, B. (1991) J. Immunol., 147, 3165–3169
(37): Stamenkovic, I., Clarke, E. A., and Seed, B. (1989) EMBO I. 8, 1403–1410
(38): Bothwell, M. (1991) Cell, 65, 915–918
(39): Chao, M. V. (1992) Neuron, 9, 583–593
(40): Connolly et al., J. Cell. Biol. 90:176–180 (1981)
(41): Skaper and Varon, Brain Res. 197: 379–389 (1980)
(42): Yu, et al., J. Biol. Chem. 255:10481–10492 (1980)
(43): Haleqoua, et al., Cell 22:571–581 (1980)
(44): Tiercy et al., J. Cell. Biol. 103:2367–2378 (1986)
(45): Hefti, J. Neurosci. 6:2155 (1986)
(46): Korsching, TINS pp. 570–573 (November/December 1986)
(47): Taylor et al. 1991
(48): Burton, L. E., Schmelzer. C. H., Szonyi, E., Yedinak, C., and Gorrell, A. (1992) J. Neurochem. 59, 1937–1945
(49): Kahle, P., Burton, L. E., Schmelzer, C. H. and Hertel, C. (1992) J. Biol. Chem., 267, 22707–22710
(50): Maisonpierre, P. C., Belluscio, L., Friedman, B., Alderson, R. F., Wiegand, S. J., Furth, M. E., Lindsay, R. M. and Yancopoulos, G. D. (1990b), Neuron, 5, 501–509
(51): Kalcheim, C., Carmeli, C. and Rosenthal, A. (1992) Proc. Natl. Acad. Sci. USA, 89, 1661–1665
(52): Hory-Lee, F., Russell, M., Lindsay and Frank, E. (1993) Proc. Natl. Acad. Sci. USA. 90, 2613–2617
(53): Ibanez, C., Ebendal, T., and Persson, H. (1991) EMBO J. 10, 2105–2110
(54): Ibanez, C. F., Ebendal, T., Barbany, G., Murray-Rust, J., Blundell, T. L., and Persson, H. (1992) Cell 69, 329–341
(55): Ibanez, C. F., Ilag, L. L., Murray-Rust, J., and Persson, H. (1993) EMBO J. 12, 2281–2293
(56): Suter, U., Angst, C., Tien, C.-L., Drinkwater, C. C., Lindsay, R. M. and Shooter, E. M. (1992) J. Neurosci., 12, 306–318
(57): Scopes, R., Protein Purification, Springer-Verlag, NY (1982)
(58): Schnell, L., Schneider, R., Kolbeck, R., Barde, Y.-A. and Schwab, M. E. (1994), Nature, 367, 170–173
(59): McDonald, N. Q., Lapatto. R., Murray-Rust, J., Gunning, J., Wlodawer, A. and Blundell, T. L. (1991) Nature, 354, 411–414

(60): Schlunegger, M. P. and Gratter, M. G. (1992), Nature, 358, 430–434
(61): McDonald, N. Q. and Hendrikson, W. A. (1993), Cell, 73, 421–424
(62): Ponder, J. W. and Richards, F. M. (1987) J. Mol. Biol., 193, 775–791
(63): Bernstein, F. C, Koetzle, T. F., Williams, G. J. B., Meyer, Jr., E. F., Brice, M. D., Rodgers, J. R., Kennard, O., Shimanouchi, T. and Tasumi, M. (1977) J. Mol. Biol., 112, 535–542
(64): Cunningham, B. C. and Wells, i. A. (1989) Science, 244, 1081–1085
(65): Rosenthal, A., Goeddel, D. V., Nguyen, T., Martin, E., Burton, L. E., Shih, A., Laramee, G. R., Wurm, F., Mason, A., Nikolics, K., and Winslow, J. W. (1991) Endocrinol. 129, 1289–1294
(66): Kunkel, T. A. (1985) Proc. Natl. Acad. Sci. USA, 82, 488–10
(67): Kunkel et al. 1987
(68): Graham, F. L., Smiley, J., Russell, W. C., and Nairn, R. (1977) J. Gen Virol. 36, 59–77
(69): Sambrook et al. 1989
(70): Gorman, C. M., Gies, D. R. and McCray, G. (1990) DNA Protein Eng. Tech., 2, 3–18
(71): Escandon, E., Burton, L. E., Szonyi, E., and Nikolics, K. (1993) J. Neurosci. Res. 34, 601–613
(72): Zoller, M. J. and Smith, M. (1983) Methods in Enzymol. 100, 468–500
(73): Messing, J., Crea, R., Seeburg. P. (1981) Nucleic Acids Res. 9, 309
(74): Schmelzer, C. H., Burton, L. E., Chan, W. P., Martin, E., Gorman, C., Canova-Davis, E., Ling, V. T., Sliwkowskl, M. B., McCray, G., Briggs, I. A., Nguyen, T. H., and Polastri, G. (1992) J. Neurochem. 59, 1675–1683
(75): Vroegop, S., Decker, D., Hinzmann, I., Poorman, R., and Buxser, S. (1992) I. Protein Chem. 11, 71–82
(76): Sutter, A., Riopelle, R. I., Hartis-Wattick, R. M., and Shooter, E. M. (1979) I. Biol. Chem. 254, 5972–5982
(77): Thoenen, H. and Barde, Y. A. (1980) Physiol. Rev., 60, 1284–1325
(78): Lindsay, R. M., Thoenen, H. and Barde, Y.-A. (1985) Dev. Biol., 112, 319–328.
(79): Barres et al 1994, manuscript submitted for publication
(80): Davies et al., (1993), J. Neuroscience 13:4215–4223 (1993)
(81): Shelton et al., (December 1984), Proc. Natl. Acad. Sci. USA 81:7951–7955
(82): Shelton et al., (April 1986) Proc. Natl. Acad. Sci. USA 83:2714–2718
(83) Rosenthal et al., (1990), Neuron, 4:767–773
(84): Hulme, E. C. and Birdsall, M. J. M., Strategy and Tactics in Receptor Binding Studies, p63–212 in Receptor-Ligand Interactions, Ed. E. C. Hulme
(85): Grotz et al., Eur. J. Biochem. 204:745–749 (1992)
(86): Arenas et al., Nature 367:368–371 (1994)
(87): Oefner et al., EMBO J., 11:3921–3926 (1992)
(88): Shelton et al., (1994), manuscript submitted for publication
(89): Sadick et al., (1994), manuscript submitted for publication

We claim:

1. A polypeptide, comprising NT-3 having an amino acid substitution of an aspartic acid corresponding to position 15 in mature NT-3, wherein the substitution confers trkB-binding activity so that the polypeptide binds to neurotrphin receptors trkB and trkC.

2. The polypeptide according to claim 1, wherein the substitution is alanine.

3. A composition comprising the polypeptide of claim 1 and a pharmaceutically acceptable carrier.

4. A covalent homodimer, comprising two D15A NT3 monomers, wherein the homodimer binds neurotrophin receptors trkB and trkC.

* * * * *

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
        (A) LENGTH: 120 amino acids
        (B) TYPE: Amino Acid
        (D) TOPOLOGY: Linear (xi) SEQUENCE DESCRIPTION: SEQ ID NO:1:

```
Ser Ser Thr His Pro Val Phe His Met Gly Glu Phe Ser Val Cys
 1               5                  10                  15

Asp Ser Val Ser Val Trp Val Gly Asp Lys Thr Thr Ala Thr Asp
                20                  25                  30

Ile Lys Gly Lys Glu Val Thr Val Leu Ala Glu Val Asn Ile Asn
                35                  40                  45

Asn Ser Val Phe Arg Gln Tyr Phe Phe Glu Thr Lys Cys Arg Ala
                50                  55                  60

Ser Asn Pro Val Glu Ser Gly Cys Arg Gly Ile Asp Ser Lys His
                65                  70                  75

Trp Asn Ser Tyr Cys Thr Thr Thr His Thr Phe Val Lys Ala Leu
                80                  85                  90

Thr Thr Asp Glu Lys Gln Ala Ala Trp Arg Phe Ile Arg Ile Asp
                95                 100                 105

Thr Ala Cys Val Cys Val Leu Ser Arg Lys Ala Thr Arg Arg Gly
               110                 115                 120
```

5,981,480

-continued (2) INFORMATION FOR SEQ ID NO:2:

(i) SEQUENCE CHARACTERISTICS:
        (A) LENGTH: 119 amino acids
        (B) TYPE: Amino Acid
        (D) TOPOLOGY: Linear (xi) SEQUENCE DESCRIPTION: SEQ ID NO:2:

```
Tyr Ala Glu His Lys Ser His Arg Gly Glu Tyr Ser Val Cys Asp
 1               5                  10                  15

Ser Glu Ser Leu Trp Val Thr Asp Lys Ser Ser Ala Ile Asp Ile
                20                  25                  30

Arg Gly His Gln Val Thr Val Leu Gly Glu Ile Lys Thr Gly Asn
                35                  40                  45

Ser Pro Val Lys Gln Tyr Phe Tyr Glu Thr Arg Cys Lys Glu Ala
                50                  55                  60

Arg Pro Val Lys Asn Gly Cys Arg Gly Ile Asp Asp Lys His Trp
                65                  70                  75

Asn Ser Gln Cys Lys Thr Ser Gln Thr Tyr Val Arg Ala Leu Thr
                80                  85                  90

Ser Glu Asn Asn Lys Leu Val Gly Trp Arg Trp Ile Arg Ile Asp
                95                  100                 105

Thr Ser Cys Val Cys Ala Leu Ser Arg Lys Ile Gly Arg Thr
                110                 115             119
```

(2) INFORMATION FOR SEQ ID NO:3:

(i) SEQUENCE CHARACTERISTICS:
        (A) LENGTH: 120 amino acids
        (B) TYPE: Amino Acid
        (D) TOPOLOGY: Linear (xi) SEQUENCE DESCRIPTION: SEQ ID NO:3:

```
Ser Ser Ser His Pro Ile Phe His Arg Gly Glu Phe Ser Val Cys
 1               5                  10                  15

Asp Ser Val Ser Val Trp Val Gly Asp Lys Thr Thr Ala Thr Asp
                20                  25                  30

Ile Lys Gly Lys Glu Val Met Val Leu Gly Glu Val Asn Ile Asn
                35                  40                  45

Asn Ser Val Phe Lys Gln Tyr Phe Phe Glu Thr Lys Cys Arg Asp
                50                  55                  60

Pro Asn Pro Val Asp Ser Gly Cys Arg Gly Ile Asp Ser Lys His
                65                  70                  75

Trp Asn Ser Tyr Cys Thr Thr Thr His Thr Phe Val Lys Ala Leu
                80                  85                  90

Thr Met Asp Gly Lys Gln Ala Ala Trp Arg Phe Ile Arg Ile Asp
                95                  100                 105

Thr Ala Cys Val Cys Val Leu Ser Arg Lys Ala Val Arg Arg Ala
                110                 115                 120
```

(2) INFORMATION FOR SEQ ID NO:4:

(i) SEQUENCE CHARACTERISTICS:
        (A) LENGTH: 119 amino acids
        (B) TYPE: Amino Acid
        (D) TOPOLOGY: Linear (xi) SEQUENCE DESCRIPTION: SEQ ID NO:4:

```
His Ser Asp Pro Ala Arg Arg Gly Glu Leu Ser Val Cys Asp Ser
 1               5                  10                  15
```

```
Ile Ser Glu Trp Val Thr Ala Ala Asp Lys Lys Thr Ala Val Asp
             20                  25                  30

Met Ser Gly Gly Thr Val Thr Val Leu Glu Lys Val Pro Val Ser
         35                  40                  45

Lys Gly Gln Leu Lys Gln Tyr Phe Tyr Glu Thr Lys Cys Asn Pro
     50                  55                  60

Met Gly Tyr Thr Lys Glu Gly Cys Arg Gly Ile Asp Lys Arg His
 65                  70                  75

Trp Asn Ser Gln Cys Arg Thr Thr Gln Ser Tyr Val Arg Ala Leu
             80                  85                  90

Thr Met Asp Ser Lys Lys Arg Ile Gly Trp Arg Phe Ile Arg Ile
         95                 100                 105

Asp Thr Ser Cys Val Cys Thr Leu Thr Ile Lys Arg Gly Arg
    110                 115                 119
```

(2) INFORMATION FOR SEQ ID NO:5:

(i) SEQUENCE CHARACTERISTICS:
        (A) LENGTH: 130 amino acids
        (B) TYPE: Amino Acid
        (D) TOPOLOGY: Linear (xi) SEQUENCE DESCRIPTION: SEQ ID NO:5:

```
Gly Val Ser Glu Thr Ala Pro Ala Ser Arg Arg Gly Glu Leu Ala
 1               5                  10                  15

Val Cys Asp Ala Val Ser Gly Trp Val Thr Asp Arg Arg Thr Ala
             20                  25                  30

Val Asp Leu Arg Gly Arg Glu Val Glu Val Leu Gly Glu Val Pro
         35                  40                  45

Ala Ala Gly Gly Ser Pro Leu Arg Gln Tyr Phe Phe Glu Thr Arg
     50                  55                  60

Cys Lys Ala Asp Asn Ala Glu Glu Gly Gly Pro Gly Ala Gly Gly
 65                  70                  75

Gly Gly Cys Arg Gly Val Asp Arg Arg His Trp Val Ser Glu Cys
             80                  85                  90

Lys Ala Lys Gln Ser Tyr Val Arg Ala Leu Thr Ala Asp Ala Gln
         95                 100                 105

Gly Arg Val Gly Trp Arg Trp Ile Arg Ile Asp Thr Ala Cys Val
    110                 115                 120

Cys Thr Leu Leu Ser Arg Thr Gly Arg Ala
    125                 130
```

(2) INFORMATION FOR SEQ ID NO:6:

(i) SEQUENCE CHARACTERISTICS:
        (A) LENGTH: 34 base pairs
        (B) TYPE: Nucleic Acid
        (C) STRANDEDNESS: Single
        (D) TOPOLOGY: Linear (xi) SEQUENCE DESCRIPTION: SEQ ID NO:6:

GGTCACCCAC AAGCTTTCAC TGGCACATAC CGAG            34

(2) INFORMATION FOR SEQ ID NO:7:

(i) SEQUENCE CHARACTERISTICS:
        (A) LENGTH: 50 base pairs
        (B) TYPE: Nucleic Acid
        (C) STRANDEDNESS: Single
        (D) TOPOLOGY: Linear (xi) SEQUENCE DESCRIPTION: SEQ ID NO:7:

GTACTCCCCT CGGTGGAAGA TGGGATGGCT CGAGGACCGT TTCCGCCGTG          50

(2) INFORMATION FOR SEQ ID NO:8:

(i) SEQUENCE CHARACTERISTICS:
        (A) LENGTH: 5 amino acids
        (B) TYPE: Amino Acid
        (D) TOPOLOGY: Linear (xi) SEQUENCE DESCRIPTION: SEQ ID NO:8:

Gly Gly Ser Gly Gly
 1          5

(2) INFORMATION FOR SEQ ID NO:9:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO:9:

Gln Cys Arg Thr Thr Gln Ser Tyr Val Arg
 1          5               10

(2) INFORMATION FOR SEQ ID NO:10:

(i) SEQUENCE CHARACTERISTICS:
        (A) LENGTH: 6 amino acids
        (B) TYPE: Amino Acid
        (D) TOPOLOGY: Linear (xi) SEQUENCE DESCRIPTION: SEQ ID NO:10:

Ser Lys Lys Arg Ile Gly
 1          5   6

(2) INFORMATION FOR SEQ ID NO:11:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO:11:

Ser Ser Ser His Pro Ile Phe
 1          5      7

(2) INFORMATION FOR SEQ ID NO:12:

(i) SEQUENCE CHARACTERISTICS:
        (A) LENGTH: 6 amino acids
        (B) TYPE: Amino Acid
        (D) TOPOLOGY: Linear (xi) SEQUENCE DESCRIPTION: SEQ ID NO:12:

Tyr Ala Glu His Lys Ser
 1          5   6

(2) INFORMATION FOR SEQ ID NO:13:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO:13:

Tyr Ala Ser His Pro Ile Phe

```
                  1               5        7

(2) INFORMATION FOR SEQ ID NO:14:

(i) SEQUENCE CHARACTERISTICS:
          (A) LENGTH: 6 amino acids
          (B) TYPE: Amino Acid
          (D) TOPOLOGY: Linear (xi) SEQUENCE DESCRIPTION: SEQ ID NO:14:

Tyr Ala His Pro Ile Phe
  1               5   6

(2) INFORMATION FOR SEQ ID NO:15:

(i) SEQUENCE CHARACTERISTICS:
          (A) LENGTH: 7 amino acids
          (B) TYPE: Amino Acid
          (D) TOPOLOGY: Linear (xi) SEQUENCE DESCRIPTION: SEQ ID NO:15:

Tyr Ala Ser His Pro Ile Ser
  1               5        7

(2) INFORMATION FOR SEQ ID NO:16:

(i) SEQUENCE CHARACTERISTICS:
          (A) LENGTH: 7 amino acids
          (B) TYPE: Amino Acid
          (D) TOPOLOGY: Linear (xi) SEQUENCE DESCRIPTION: SEQ ID NO:16:

Tyr Ala Glu His Pro Ile Phe
  1               5        7

(2) INFORMATION FOR SEQ ID NO:17:

(i) SEQUENCE CHARACTERISTICS:
          (A) LENGTH: 7 amino acids
          (B) TYPE: Amino Acid
          (D) TOPOLOGY: Linear (xi) SEQUENCE DESCRIPTION: SEQ ID NO:17:

Tyr Ala Gln His Pro Ile Phe
  1               5        7

(2) INFORMATION FOR SEQ ID NO:18:

(i) SEQUENCE CHARACTERISTICS:
          (A) LENGTH: 5 amino acids
          (B) TYPE: Amino Acid
          (D) TOPOLOGY: Linear (xi) SEQUENCE DESCRIPTION: SEQ ID NO:18:

His Ser Asp Pro Ala
  1               5

(2) INFORMATION FOR SEQ ID NO:19:

(i) SEQUENCE CHARACTERISTICS:
          (A) LENGTH: 7 amino acids
          (B) TYPE: Amino Acid
          (D) TOPOLOGY: Linear (xi) SEQUENCE DESCRIPTION: SEQ ID NO:19:

Glu Asn Asn Lys Leu Val Gly
  1               5        7
```

(2) INFORMATION FOR SEQ ID NO:20:

(i) SEQUENCE CHARACTERISTICS:
        (A) LENGTH: 6 amino acids
        (B) TYPE: Amino Acid
        (D) TOPOLOGY: Linear (xi) SEQUENCE DESCRIPTION: SEQ ID NO:20:

Asp Gly Lys Gln Ala Ala
 1            5   6